United States Patent
Chen et al.

(10) Patent No.: US 11,439,324 B2
(45) Date of Patent: Sep. 13, 2022

(54) WORKOUT MONITOR INTERFACE

(71) Applicant: Apple Inc., Cupertino, CA (US)

(72) Inventors: Kevin Will Chen, Sunnyvale, CA (US);
Jay Blahnik, San Francisco, CA (US);
Gary Ian Butcher, San Jose, CA (US);
Jules K. Fennis, Menlo Park, CA (US);
David Chance Graham, Campbell, CA (US);
Lawrence Y. Yang, Bellevue, WA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 16/987,275

(22) Filed: Aug. 6, 2020

(65) Prior Publication Data

US 2021/0113116 A1    Apr. 22, 2021

Related U.S. Application Data

(63) Continuation of application No. 15/600,243, filed on May 19, 2017, now Pat. No. 10,736,543.

(Continued)

(51) Int. Cl.
*G06F 17/00* (2019.01)
*A61B 5/11* (2006.01)
(Continued)

(52) U.S. Cl.
CPC ......... *A61B 5/1118* (2013.01); *A61B 5/6801* (2013.01); *A61B 5/7435* (2013.01); *A63B 24/0062* (2013.01); *G16H 20/30* (2018.01); *A61B 5/1123* (2013.01); *A61B 2503/10* (2013.01); *A63B 2225/50* (2013.01)

(58) Field of Classification Search
CPC ............ A63B 2225/50; A63B 24/0062; A61B 2503/10; A61B 5/1123; A61B 5/7435; A61B 5/6801; A61B 5/1118; G16H 20/30
See application file for complete search history.

(56) References Cited

U.S. PATENT DOCUMENTS 4,205,628 A    6/1980    Null
4,842,266 A    6/1989    Sweeney et al.
(Continued)

FOREIGN PATENT DOCUMENTS

CA    2815518 A1    5/2012
CN    1337638 A    2/2002
(Continued)

OTHER PUBLICATIONS

Applicant-Initiated Interview Summary received for U.S. Appl. No. 16/888,629, dated Aug. 4, 2021, 5 pages.
(Continued)

*Primary Examiner* — Mohammed H Zuberi
(74) *Attorney, Agent, or Firm* — Dentons US LLP

(57) ABSTRACT

The present disclosure relates to systems and processes for monitoring a workout and for generating improved interfaces for the same. An electronic device displays a first user interface in response to initiating a workout session. In addition, the electronic device receives an input while displaying the first user interface, and in response to the input, ceases to display the first user interface and displays a second user interface associated with a music application of the electronic device.

30 Claims, 28 Drawing Sheets

Related U.S. Application Data

(60) Provisional application No. 62/398,440, filed on Sep. 22, 2016.

(51) Int. Cl.
  *A61B 5/00* (2006.01)
  *A63B 24/00* (2006.01)
  *G16H 20/30* (2018.01)

(56) References Cited

U.S. PATENT DOCUMENTS

| | | |
|---|---|---|
| 5,423,863 A | 6/1995 | Felblinger et al. |
| 5,458,548 A | 10/1995 | Crossing et al. |
| 5,474,077 A | 12/1995 | Suga |
| 5,642,731 A | 7/1997 | Kehr |
| 5,685,723 A | 11/1997 | Ladin et al. |
| 5,788,655 A | 8/1998 | Yoshimura et al. |
| 6,013,008 A | 1/2000 | Fukushima |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,244,988 B1 | 6/2001 | Delman |
| 6,302,789 B2 | 10/2001 | Harada et al. |
| 6,416,471 B1 | 7/2002 | Kumar et al. |
| 6,603,477 B1 | 8/2003 | Tittle |
| 6,639,584 B1 | 10/2003 | Li |
| 6,705,972 B1 | 3/2004 | Takano et al. |
| 6,837,827 B1 | 1/2005 | Lee et al. |
| 6,866,613 B1 | 3/2005 | Brown et al. |
| 7,020,514 B1 | 3/2006 | Wiesel |
| 7,128,693 B2 | 10/2006 | Brown et al. |
| 7,251,454 B2 | 7/2007 | White |
| 7,302,272 B2 | 11/2007 | Ackley |
| 7,662,065 B1 | 2/2010 | Kahn et al. |
| 7,695,406 B2 | 4/2010 | Waters |
| 7,739,148 B2 | 6/2010 | Suzuki et al. |
| 8,060,229 B2 | 11/2011 | Gupta et al. |
| 8,105,208 B2 | 1/2012 | Oleson et al. |
| 8,321,006 B1 | 11/2012 | Snyder et al. |
| 8,341,557 B2 * | 12/2012 | Pisula ............... G06F 3/04886 715/833 |
| 8,475,339 B2 | 7/2013 | Hwang et al. |
| 8,496,563 B2 | 7/2013 | Komatsu et al. |
| 8,676,170 B2 | 3/2014 | Porrati et al. |
| 8,768,648 B2 | 7/2014 | Panther et al. |
| 8,784,115 B1 | 7/2014 | Chuang |
| 8,784,271 B2 * | 7/2014 | Brumback ............ G06F 1/3265 482/8 |
| 8,825,445 B2 | 9/2014 | Hoffman et al. |
| 8,934,963 B1 | 1/2015 | Farazi |
| 8,990,006 B1 | 3/2015 | Wallace et al. |
| 9,011,292 B2 | 4/2015 | Weast et al. |
| 9,020,538 B1 | 4/2015 | White et al. |
| 9,224,291 B2 | 12/2015 | Moll-Carrillo et al. |
| 9,230,076 B2 | 1/2016 | King et al. |
| 9,449,365 B2 | 9/2016 | Roberts |
| 9,532,734 B2 | 1/2017 | Hoffman et al. |
| 9,557,881 B1 | 1/2017 | Jain et al. |
| 9,589,445 B2 | 3/2017 | White et al. |
| 9,712,629 B2 | 7/2017 | Molettiere et al. |
| 9,734,477 B2 | 8/2017 | Weast et al. |
| 9,813,642 B1 | 11/2017 | Chen et al. |
| 9,817,481 B2 * | 11/2017 | Pantelopoulos ........ G06F 3/017 |
| 9,854,653 B1 | 12/2017 | Ackmann et al. |
| 9,880,805 B1 | 1/2018 | Guralnick |
| 9,910,571 B2 * | 3/2018 | Chen ................... G06F 3/0482 |
| 9,940,682 B2 | 4/2018 | Hoffman et al. |
| 10,056,006 B1 | 8/2018 | Hsu-Hoffman et al. |
| 10,220,258 B2 | 3/2019 | Gu et al. |
| 10,226,195 B2 | 3/2019 | Briante et al. |
| 10,300,334 B1 | 5/2019 | Chuang |
| 10,304,347 B2 | 5/2019 | Wilson et al. |
| 10,339,830 B2 | 7/2019 | Han et al. |
| 10,398,381 B1 | 9/2019 | Heneghan et al. |
| 10,489,508 B2 | 11/2019 | Zhai et al. |
| 10,500,441 B2 | 12/2019 | Lagree |
| 10,736,543 B2 | 8/2020 | Chen et al. |
| 10,777,314 B1 | 9/2020 | Williams et al. |
| 10,978,195 B2 | 4/2021 | Blahnik et al. |
| 11,103,161 B2 | 8/2021 | Williams et al. |
| 11,107,569 B1 | 8/2021 | Devoto |
| 11,152,100 B2 | 10/2021 | Crowley et al. |
| 11,202,598 B2 | 12/2021 | Soli et al. |
| 11,209,957 B2 | 12/2021 | Dryer et al. |
| 11,317,833 B2 | 5/2022 | Williams et al. |
| 2001/0049470 A1 | 12/2001 | Mault et al. |
| 2002/0045960 A1 | 4/2002 | Phillips et al. |
| 2002/0086774 A1 | 7/2002 | Warner |
| 2002/0118121 A1 | 8/2002 | Lehrman et al. |
| 2003/0023178 A1 | 1/2003 | Bischoff et al. |
| 2003/0064860 A1 | 4/2003 | Yamashita et al. |
| 2003/0134714 A1 | 7/2003 | Oishi et al. |
| 2003/0179229 A1 | 9/2003 | Van et al. |
| 2003/0181291 A1 | 9/2003 | Ogawa |
| 2003/0182628 A1 | 9/2003 | Lira |
| 2003/0216971 A1 | 11/2003 | Sick et al. |
| 2003/0226695 A1 | 12/2003 | Mault |
| 2004/0014567 A1 | 1/2004 | Mendel |
| 2004/0077462 A1 | 4/2004 | Brown et al. |
| 2004/0128286 A1 | 7/2004 | Yasushi et al. |
| 2004/0236189 A1 | 11/2004 | Hawthorne et al. |
| 2005/0075214 A1 | 4/2005 | Brown et al. |
| 2005/0079905 A1 | 4/2005 | Martens |
| 2005/0113650 A1 | 5/2005 | Pacione et al. |
| 2005/0124324 A1 | 6/2005 | Thomas et al. |
| 2005/0139852 A1 | 6/2005 | Chen et al. |
| 2005/0165627 A1 | 7/2005 | Fotsch et al. |
| 2005/0172311 A1 | 8/2005 | Hjelt et al. |
| 2005/0197063 A1 | 9/2005 | White et al. |
| 2005/0216867 A1 | 9/2005 | Marvit et al. |
| 2005/0228735 A1 | 10/2005 | Duquette |
| 2005/0272564 A1 | 12/2005 | Pyles et al. |
| 2006/0020174 A1 | 1/2006 | Matsumura et al. |
| 2006/0052727 A1 | 3/2006 | Palestrant |
| 2006/0098109 A1 | 5/2006 | Ooki |
| 2006/0106741 A1 | 5/2006 | Janarthanan |
| 2006/0184800 A1 | 8/2006 | Rosenberg |
| 2006/0240959 A1 | 10/2006 | Huang |
| 2006/0250524 A1 | 11/2006 | Roche |
| 2007/0021269 A1 | 1/2007 | Shum |
| 2007/0032733 A1 | 2/2007 | Burton |
| 2007/0033069 A1 | 2/2007 | Rao et al. |
| 2007/0056727 A1 | 3/2007 | Newman |
| 2007/0071256 A1 | 3/2007 | Ito |
| 2007/0113726 A1 | 5/2007 | Oliver et al. |
| 2007/0136093 A1 | 6/2007 | Rankin et al. |
| 2007/0143433 A1 | 6/2007 | Daigle |
| 2007/0169614 A1 | 7/2007 | Sasaki et al. |
| 2007/0249949 A1 | 10/2007 | Hadley |
| 2007/0271065 A1 | 11/2007 | Gupta et al. |
| 2008/0020803 A1 | 1/2008 | Rios et al. |
| 2008/0027673 A1 | 1/2008 | Trumm |
| 2008/0051919 A1 | 2/2008 | Sakai et al. |
| 2008/0052945 A1 | 3/2008 | Matas et al. |
| 2008/0058626 A1 | 3/2008 | Miyata et al. |
| 2008/0076637 A1 | 3/2008 | Gilley et al. |
| 2008/0082145 A1 | 4/2008 | Skwarek et al. |
| 2008/0086318 A1 | 4/2008 | Gilley et al. |
| 2008/0096726 A1 | 4/2008 | Riley et al. |
| 2008/0141135 A1 | 6/2008 | Mason et al. |
| 2008/0150731 A1 | 6/2008 | Laukkanen et al. |
| 2008/0161161 A1 | 7/2008 | Pipinich et al. |
| 2008/0161707 A1 | 7/2008 | Farringdon et al. |
| 2008/0200312 A1 | 8/2008 | Tagliabue |
| 2008/0229226 A1 | 9/2008 | Rowbottom et al. |
| 2008/0254767 A1 | 10/2008 | Jin |
| 2008/0262946 A1 | 10/2008 | Wren |
| 2008/0300110 A1 | 12/2008 | Smith et al. |
| 2009/0007017 A1 * | 1/2009 | Anzures ............... G06F 3/0482 715/835 |
| 2009/0012988 A1 | 1/2009 | Brown |
| 2009/0047645 A1 | 2/2009 | Dibenedetto et al. |

(56) References Cited

U.S. PATENT DOCUMENTS

| | | |
|---|---|---|
| 2009/0118100 A1 | 5/2009 | Oliver et al. |
| 2009/0149299 A1 | 6/2009 | Tchao et al. |
| 2009/0164567 A1 | 6/2009 | Hara |
| 2009/0170532 A1 | 7/2009 | Lee et al. |
| 2009/0192823 A1 | 7/2009 | Hawkins et al. |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0233771 A1 | 9/2009 | Quatrochi et al. |
| 2009/0259134 A1 | 10/2009 | Levine |
| 2009/0262088 A1 | 10/2009 | Moll-Carrillo et al. |
| 2009/0268949 A1 | 10/2009 | Ueshima et al. |
| 2009/0287103 A1 | 11/2009 | Pillai |
| 2009/0319243 A1 | 12/2009 | Suarez-Rivera et al. |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0060586 A1* | 3/2010 | Pisula ............... G06F 3/04886 345/169 |
| 2010/0062818 A1 | 3/2010 | Haughay et al. |
| 2010/0062905 A1 | 3/2010 | Rottler et al. |
| 2010/0064255 A1 | 3/2010 | Rottler et al. |
| 2010/0076331 A1 | 3/2010 | Chan et al. |
| 2010/0079291 A1 | 4/2010 | Kroll et al. |
| 2010/0121700 A1 | 5/2010 | Wigder et al. |
| 2010/0137106 A1 | 6/2010 | Oshima et al. |
| 2010/0145209 A1 | 6/2010 | Lee et al. |
| 2010/0179832 A1 | 7/2010 | Van et al. |
| 2010/0194692 A1 | 8/2010 | Orr et al. |
| 2010/0198453 A1 | 8/2010 | Dorogusker et al. |
| 2010/0281374 A1 | 11/2010 | Schulz et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0309149 A1 | 12/2010 | Blumenberg et al. |
| 2010/0331145 A1 | 12/2010 | Lakovic et al. |
| 2011/0003665 A1 | 1/2011 | Burton et al. |
| 2011/0016120 A1 | 1/2011 | Haughay et al. |
| 2011/0032105 A1 | 2/2011 | Hoffman et al. |
| 2011/0066051 A1 | 3/2011 | Moon et al. |
| 2011/0071869 A1 | 3/2011 | Obrien et al. |
| 2011/0074699 A1 | 3/2011 | Marr et al. |
| 2011/0098928 A1 | 4/2011 | Hoffman et al. |
| 2011/0106553 A1 | 5/2011 | Tanaka et al. |
| 2011/0112418 A1 | 5/2011 | Feild et al. |
| 2011/0125041 A1 | 5/2011 | Fischell et al. |
| 2011/0137678 A1 | 6/2011 | Williams |
| 2011/0137836 A1 | 6/2011 | Kuriyama et al. |
| 2011/0159469 A1 | 6/2011 | Hwang et al. |
| 2011/0167369 A1 | 7/2011 | Van Os |
| 2011/0201911 A1 | 8/2011 | Johnson et al. |
| 2011/0213276 A1 | 9/2011 | Sarussi et al. |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0246509 A1 | 10/2011 | Migita et al. |
| 2011/0261079 A1 | 10/2011 | Ingrassia et al. |
| 2011/0275940 A1 | 11/2011 | Nims et al. |
| 2011/0306389 A1 | 12/2011 | Nagayama |
| 2011/0307821 A1 | 12/2011 | Martens |
| 2012/0015778 A1 | 1/2012 | Lee et al. |
| 2012/0015779 A1 | 1/2012 | Powch et al. |
| 2012/0030623 A1 | 2/2012 | Hoellwarth |
| 2012/0034897 A1 | 2/2012 | Kreitzer et al. |
| 2012/0041767 A1 | 2/2012 | Hoffman et al. |
| 2012/0042039 A1 | 2/2012 | Mark |
| 2012/0059664 A1 | 3/2012 | Georgiev et al. |
| 2012/0071770 A1 | 3/2012 | Grey et al. |
| 2012/0092383 A1 | 4/2012 | Hysek et al. |
| 2012/0105225 A1 | 5/2012 | Valtonen |
| 2012/0116550 A1 | 5/2012 | Hoffman et al. |
| 2012/0150759 A1 | 6/2012 | Tarjan |
| 2012/0159380 A1* | 6/2012 | Kocienda ............ G06F 3/04842 715/783 |
| 2012/0179319 A1 | 7/2012 | Gilman et al. |
| 2012/0232414 A1 | 9/2012 | Mollicone et al. |
| 2012/0253485 A1 | 10/2012 | Weast et al. |
| 2012/0274508 A1* | 11/2012 | Brown ................ G04G 17/04 342/357.57 |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0302843 A1 | 11/2012 | Otsubo et al. |
| 2012/0317167 A1 | 12/2012 | Rahman et al. |
| 2012/0326873 A1 | 12/2012 | Utter |
| 2013/0054150 A1 | 2/2013 | Sacks et al. |
| 2013/0054720 A1 | 2/2013 | Kang et al. |
| 2013/0067050 A1 | 3/2013 | Kotteri et al. |
| 2013/0081083 A1 | 3/2013 | Yu et al. |
| 2013/0093715 A1 | 4/2013 | Marsden et al. |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0115583 A1 | 5/2013 | Gordon et al. |
| 2013/0132028 A1 | 5/2013 | Crankson et al. |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0151285 A1 | 6/2013 | Mclaren et al. |
| 2013/0158367 A1 | 6/2013 | Pacione et al. |
| 2013/0184613 A1 | 7/2013 | Homsi et al. |
| 2013/0185097 A1 | 7/2013 | Saria et al. |
| 2013/0187923 A1 | 7/2013 | Yoshimoto et al. |
| 2013/0188322 A1 | 7/2013 | Lowe et al. |
| 2013/0197679 A1 | 8/2013 | Balakrishnan et al. |
| 2013/0198672 A1 | 8/2013 | Yoon et al. |
| 2013/0203475 A1 | 8/2013 | Shin et al. |
| 2013/0215119 A1 | 8/2013 | Vanhoecke |
| 2013/0217979 A1 | 8/2013 | Blackadar et al. |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0262155 A1 | 10/2013 | Hinkamp |
| 2013/0263719 A1 | 10/2013 | Watterson et al. |
| 2013/0324210 A1 | 12/2013 | Doig et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0330694 A1 | 12/2013 | Watterson |
| 2013/0332286 A1 | 12/2013 | Medelius et al. |
| 2013/0345978 A1 | 12/2013 | Lush et al. |
| 2014/0037107 A1 | 2/2014 | Marino et al. |
| 2014/0038781 A1 | 2/2014 | Foley et al. |
| 2014/0039840 A1 | 2/2014 | Yuen et al. |
| 2014/0067096 A1 | 3/2014 | Aibara |
| 2014/0081666 A1 | 3/2014 | Teller et al. |
| 2014/0089836 A1 | 3/2014 | Damani et al. |
| 2014/0108998 A1 | 4/2014 | Chaudhri et al. |
| 2014/0139637 A1 | 5/2014 | Mistry et al. |
| 2014/0176346 A1* | 6/2014 | Brumback ............ G06F 3/01 340/870.16 |
| 2014/0176475 A1 | 6/2014 | Myers et al. |
| 2014/0180786 A1 | 6/2014 | Sullivan |
| 2014/0189584 A1* | 7/2014 | Weng ................ G06F 1/163 715/833 |
| 2014/0200691 A1 | 7/2014 | Lee et al. |
| 2014/0218369 A1 | 8/2014 | Yuen et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0278229 A1 | 9/2014 | Hong et al. |
| 2014/0282153 A1 | 9/2014 | Christiansen et al. |
| 2014/0288680 A1 | 9/2014 | Hoffman et al. |
| 2014/0310598 A1 | 10/2014 | Sprague et al. |
| 2014/0310643 A1 | 10/2014 | Karmanenko et al. |
| 2014/0331314 A1 | 11/2014 | Fujioka |

(56) References Cited

U.S. PATENT DOCUMENTS

| | | |
|---|---|---|
| 2014/0336796 A1 | 11/2014 | Agnew |
| 2014/0337041 A1 | 11/2014 | Madden et al. |
| 2014/0337450 A1 | 11/2014 | Choudhary et al. |
| 2014/0337451 A1 | 11/2014 | Choudhary et al. |
| 2014/0344693 A1 | 11/2014 | Reese et al. |
| 2014/0344723 A1 | 11/2014 | Malik et al. |
| 2014/0344951 A1 | 11/2014 | Brewer |
| 2014/0358473 A1 | 12/2014 | Goel et al. |
| 2014/0358584 A1 | 12/2014 | Worden et al. |
| 2014/0371887 A1 | 12/2014 | Hoffman et al. |
| 2015/0004578 A1 | 1/2015 | Gilley et al. |
| 2015/0018632 A1 | 1/2015 | Khair |
| 2015/0046814 A1 | 2/2015 | Haughay et al. |
| 2015/0057942 A1 | 2/2015 | Self et al. |
| 2015/0057943 A1 | 2/2015 | Self et al. |
| 2015/0058263 A1 | 2/2015 | Landers |
| 2015/0065095 A1 | 3/2015 | Seo et al. |
| 2015/0065302 A1 | 3/2015 | Ou et al. |
| 2015/0067513 A1 | 3/2015 | Zambetti et al. |
| 2015/0067811 A1 | 3/2015 | Agnew et al. |
| 2015/0074571 A1* | 3/2015 | Marti .................. G06F 3/0482 715/765 |
| 2015/0081059 A1 | 3/2015 | Hwang et al. |
| 2015/0081060 A1 | 3/2015 | Hwang et al. |
| 2015/0081529 A1 | 3/2015 | Lee et al. |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0106025 A1 | 4/2015 | Keller et al. |
| 2015/0112700 A1 | 4/2015 | Sublett et al. |
| 2015/0113553 A1 | 4/2015 | Pan |
| 2015/0118657 A1 | 4/2015 | Shrake et al. |
| 2015/0124067 A1 | 5/2015 | Bala et al. |
| 2015/0130830 A1 | 5/2015 | Nagasaki et al. |
| 2015/0142689 A1 | 5/2015 | Squires |
| 2015/0153943 A1 | 6/2015 | Wang |
| 2015/0164349 A1 | 6/2015 | Gopalakrishnan et al. |
| 2015/0180746 A1 | 6/2015 | Day et al. |
| 2015/0181314 A1 | 6/2015 | Swanson |
| 2015/0185967 A1 | 7/2015 | Ly et al. |
| 2015/0193805 A1 | 7/2015 | Filipiak |
| 2015/0196804 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0217163 A1 | 8/2015 | Amis et al. |
| 2015/0220883 A1 | 8/2015 | Bfar et al. |
| 2015/0251053 A1 | 9/2015 | Hoffman et al. |
| 2015/0262497 A1 | 9/2015 | Landau et al. |
| 2015/0269848 A1 | 9/2015 | Yuen et al. |
| 2015/0293592 A1 | 10/2015 | Cheong et al. |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0343709 A1 | 12/2015 | Gerstle et al. |
| 2015/0347711 A1 | 12/2015 | Soli et al. |
| 2015/0350861 A1 | 12/2015 | Soli et al. |
| 2015/0351655 A1 | 12/2015 | Coleman |
| 2015/0374310 A1 | 12/2015 | Lee |
| 2016/0000379 A1 | 1/2016 | Pougatchev et al. |
| 2016/0004432 A1* | 1/2016 | Bernstein .............. G06F 3/0486 715/769 |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0048298 A1 | 2/2016 | Choi et al. |
| 2016/0058336 A1 | 3/2016 | Blahnik et al. |
| 2016/0058337 A1 | 3/2016 | Blahnik et al. |
| 2016/0062582 A1 | 3/2016 | Wilson et al. |
| 2016/0065505 A1 | 3/2016 | Iskander |
| 2016/0070275 A1 | 3/2016 | Anderson et al. |
| 2016/0072896 A1 | 3/2016 | Petersen et al. |
| 2016/0085937 A1 | 3/2016 | Dettinger et al. |
| 2016/0089569 A1 | 3/2016 | Blahnik |
| 2016/0107031 A1 | 4/2016 | Palatsi et al. |
| 2016/0135731 A1 | 5/2016 | Drennan |
| 2016/0140828 A1 | 5/2016 | Deforest |
| 2016/0156584 A1 | 6/2016 | Hum et al. |
| 2016/0196635 A1 | 7/2016 | Cho et al. |
| 2016/0210099 A1 | 7/2016 | Hampapuram et al. |
| 2016/0220225 A1 | 8/2016 | Wang et al. |
| 2016/0235374 A1 | 8/2016 | Miller et al. |
| 2016/0246880 A1 | 8/2016 | Battiah et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0301794 A1 | 10/2016 | Schlakman et al. |
| 2016/0302680 A1 | 10/2016 | Narusawa et al. |
| 2016/0302717 A1 | 10/2016 | Tawa et al. |
| 2016/0324457 A1 | 11/2016 | Dagum |
| 2016/0328736 A1 | 11/2016 | Wang et al. |
| 2016/0332025 A1 | 11/2016 | Repka |
| 2016/0346607 A1 | 12/2016 | Rapfogel |
| 2016/0371464 A1 | 12/2016 | Bricker |
| 2016/0375306 A1 | 12/2016 | Gu et al. |
| 2016/0379511 A1 | 12/2016 | Dawson et al. |
| 2017/0001073 A1 | 1/2017 | Krueger et al. |
| 2017/0011210 A1 | 1/2017 | Cheong et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0053542 A1 | 2/2017 | Wilson et al. |
| 2017/0065224 A1 | 3/2017 | Rahko et al. |
| 2017/0095695 A1 | 4/2017 | Mangusson et al. |
| 2017/0143262 A1 | 5/2017 | Kurunmäki et al. |
| 2017/0153606 A1 | 6/2017 | Pitis et al. |
| 2017/0153804 A1 | 6/2017 | Kim et al. |
| 2017/0161014 A1 | 6/2017 | Kikugawa et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0243508 A1 | 8/2017 | Cheng et al. |
| 2017/0266494 A1 | 9/2017 | Crankson et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0301039 A1 | 10/2017 | Dyer et al. |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0333752 A1 | 11/2017 | Korkala et al. |
| 2017/0337033 A1 | 11/2017 | Duyan et al. |
| 2017/0348562 A1 | 12/2017 | Jung et al. |
| 2017/0354845 A1 | 12/2017 | Williams et al. |
| 2017/0357520 A1 | 12/2017 | De Vries et al. |
| 2018/0000426 A1 | 1/2018 | Li |
| 2018/0001184 A1 | 1/2018 | Tran et al. |
| 2018/0032234 A1 | 2/2018 | Michalske |
| 2018/0053200 A1 | 2/2018 | Cronin et al. |
| 2018/0056132 A1 | 3/2018 | Foley et al. |
| 2018/0065025 A1 | 3/2018 | Toda et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0126248 A1 | 5/2018 | Dion et al. |
| 2018/0137937 A1 | 5/2018 | Gass et al. |
| 2018/0140903 A1 | 5/2018 | Poure et al. |
| 2018/0150709 A1 | 5/2018 | Ha |
| 2018/0189077 A1 | 7/2018 | Gupta et al. |
| 2018/0206766 A1 | 7/2018 | Blahnik et al. |
| 2018/0272190 A1 | 9/2018 | Miura et al. |
| 2018/0294053 A1 | 10/2018 | Runyon et al. |
| 2018/0318647 A1 | 11/2018 | Foley et al. |

(56) References Cited

U.S. PATENT DOCUMENTS

| | | | |
|---|---|---|---|
| 2018/0329584 | A1 | 11/2018 | Williams et al. |
| 2018/0339195 | A1 | 11/2018 | Bernotas |
| 2018/0345078 | A1 | 12/2018 | Blahnik et al. |
| 2019/0008467 | A1 | 1/2019 | Averina et al. |
| 2019/0025995 | A1 | 1/2019 | Williams |
| 2019/0034049 | A1 | 1/2019 | Williams et al. |
| 2019/0034050 | A1 | 1/2019 | Williams et al. |
| 2019/0089701 | A1 | 3/2019 | Mercury et al. |
| 2019/0104951 | A1 | 4/2019 | Valys et al. |
| 2019/0143194 | A1 | 5/2019 | Evancha et al. |
| 2019/0184234 | A1 | 6/2019 | Packles et al. |
| 2019/0209777 | A1 | 7/2019 | O'connell et al. |
| 2019/0232110 | A1 | 8/2019 | Williams et al. |
| 2019/0232111 | A1 | 8/2019 | Williams et al. |
| 2019/0274565 | A1 | 9/2019 | Soli et al. |
| 2019/0279520 | A1 | 9/2019 | Wilson et al. |
| 2019/0336044 | A1 | 11/2019 | Williams et al. |
| 2019/0336045 | A1 | 11/2019 | Williams et al. |
| 2019/0336827 | A1 | 11/2019 | Intonato et al. |
| 2019/0339849 | A1 | 11/2019 | Williams et al. |
| 2019/0342616 | A1 | 11/2019 | Domm et al. |
| 2019/0387982 | A1 | 12/2019 | Buller |
| 2020/0014967 | A1 | 1/2020 | Putnam |
| 2020/0054931 | A1 | 2/2020 | Martin et al. |
| 2020/0098278 | A1 | 3/2020 | Doti et al. |
| 2020/0101365 | A1 | 4/2020 | Wilson et al. |
| 2020/0110814 | A1 | 4/2020 | Abuelsaad et al. |
| 2020/0149921 | A1 | 5/2020 | Hoffman et al. |
| 2020/0160961 | A1 | 5/2020 | Wadhawan et al. |
| 2020/0297249 | A1 | 9/2020 | Williams et al. |
| 2020/0357522 | A1 | 11/2020 | Pahwa et al. |
| 2020/0381100 | A1 | 12/2020 | Williams et al. |
| 2020/0382613 | A1 | 12/2020 | Sundstrom et al. |
| 2021/0007632 | A1 | 1/2021 | Blahnik et al. |
| 2021/0007633 | A1 | 1/2021 | Blahnik et al. |
| 2021/0093919 | A1 | 4/2021 | Lyke et al. |
| 2021/0110908 | A1 | 4/2021 | Blahnik et al. |
| 2021/0113137 | A1 | 4/2021 | Soli et al. |
| 2021/0145321 | A1 | 5/2021 | Chen et al. |
| 2021/0191584 | A1 | 6/2021 | Williams et al. |
| 2021/0193293 | A1 | 6/2021 | Blahnik et al. |
| 2021/0252337 | A1 | 8/2021 | Devine et al. |
| 2021/0252341 | A1 | 8/2021 | Devine et al. |
| 2021/0252369 | A1 | 8/2021 | Devine et al. |
| 2021/0255747 | A1 | 8/2021 | Devine et al. |
| 2021/0255758 | A1 | 8/2021 | Devine et al. |
| 2021/0255826 | A1 | 8/2021 | Devine et al. |
| 2021/0350900 | A1 | 11/2021 | Blahnik et al. |
| 2021/0379447 | A1 | 12/2021 | Lee |
| 2022/0047918 | A1 | 2/2022 | Williams et al. |
| 2022/0062707 | A1 | 3/2022 | Bedekar et al. |
| 2022/0121299 | A1 | 4/2022 | De Vries et al. |
| 2022/0157184 | A1 | 5/2022 | Wilson et al. |
| 2022/0160258 | A1 | 5/2022 | Williams et al. |

FOREIGN PATENT DOCUMENTS

| | | | |
|---|---|---|---|
| CN | 1397904 | A | 2/2003 |
| CN | 1585943 | A | 2/2005 |
| CN | 101150810 | A | 3/2008 |
| CN | 101541387 | A | 9/2009 |
| CN | 101651870 | A | 2/2010 |
| CN | 101836894 | A | 9/2010 |
| CN | 101978374 | A | 2/2011 |
| CN | 102339201 | A | 2/2012 |
| CN | 102448555 | A | 5/2012 |
| CN | 102804238 | A | 11/2012 |
| CN | 102989159 | A | 3/2013 |
| CN | 103154954 | A | 6/2013 |
| CN | 103212197 | A | 7/2013 |
| CN | 103370924 | A | 10/2013 |
| CN | 103403627 | A | 11/2013 |
| CN | 104288983 | A | 1/2015 |
| CN | 104501043 | A | 4/2015 |
| CN | 104508426 | A | 4/2015 |
| CN | 104815428 | A | 8/2015 |
| CN | 106537397 | A | 3/2017 |
| CN | 106709235 | A | 5/2017 |
| CN | 106878550 | A | 6/2017 |
| EP | 1935339 | A1 | 6/2008 |
| EP | 2025368 | A2 | 2/2009 |
| EP | 3122038 | A1 | 1/2017 |
| JP | 6-187118 | A | 7/1994 |
| JP | 2001-76078 | A | 3/2001 |
| JP | 2002-190007 | A | 7/2002 |
| JP | 2003-102868 | A | 4/2003 |
| JP | 2003-337863 | A | 11/2003 |
| JP | 2004-102609 | A | 4/2004 |
| JP | 2004-113466 | A | 4/2004 |
| JP | 2005-79814 | A | 3/2005 |
| JP | 2006-230679 | A | 9/2006 |
| JP | 2007-260288 | A | 10/2007 |
| JP | 2007-330513 | A | 12/2007 |
| JP | 2008-104758 | A | 5/2008 |
| JP | 2008-183339 | A | 8/2008 |
| JP | 2009-78134 | A | 4/2009 |
| JP | 2009-112731 | A | 5/2009 |
| JP | 2010-12335 | A | 1/2010 |
| JP | 2010-517725 | A | 5/2010 |
| JP | 2010-122901 | A | 6/2010 |
| JP | 2010-162297 | A | 7/2010 |
| JP | 2010-181280 | A | 8/2010 |
| JP | 2011-125633 | A | 6/2011 |
| JP | 2011-183101 | A | 9/2011 |
| JP | 2011-192126 | A | 9/2011 |
| JP | 2011-198184 | A | 10/2011 |
| JP | 2011-206323 | A | 10/2011 |
| JP | 2011-259253 | A | 12/2011 |
| JP | 2012-020134 | A | 2/2012 |
| JP | 2012-35071 | A | 2/2012 |
| JP | 2012-59264 | A | 3/2012 |
| JP | 2012-524640 | A | 10/2012 |
| JP | 2012-230503 | A | 11/2012 |
| JP | 2013-103020 | A | 5/2013 |
| JP | 2013-117690 | A | 6/2013 |
| JP | 2013-544140 | A | 12/2013 |
| JP | 2014-500740 | A | 1/2014 |
| JP | 2016-502875 | A | 2/2016 |
| JP | 2016-52512 | A | 4/2016 |
| JP | 2016-517329 | A | 6/2016 |
| JP | 2016-528016 | A | 9/2016 |
| JP | 2016-177151 | A | 10/2016 |
| JP | 2016-202751 | A | 12/2016 |
| JP | 2017-134689 | A | 8/2017 |
| JP | 2017-211994 | A | 11/2017 |
| JP | 2017-532069 | A | 11/2017 |
| KR | 10-2006-0117570 | A | 11/2006 |
| KR | 10-2011-0017076 | A | 2/2011 |
| KR | 10-2012-0023657 | A | 3/2012 |
| KR | 10-2012-0076559 | A | 7/2012 |
| KR | 10-2013-0043698 | A | 5/2013 |
| KR | 10-2013-0111569 | A | 10/2013 |
| KR | 10-2013-0111570 | A | 10/2013 |
| KR | 10-2013-0135282 | A | 12/2013 |
| KR | 10-2015-0026635 | A | 3/2015 |
| KR | 10-2016-0027943 | A | 3/2016 |
| KR | 10-2016-01424118 | A | 12/2016 |
| KR | 10-2017-0003608 | A | 1/2017 |
| KR | 10-2017-0029014 | A | 3/2017 |
| KR | 10-2017-0032471 | A | 3/2017 |
| KR | 10-2019-0141702 | A | 12/2019 |
| WO | 1999/41682 | A2 | 8/1999 |
| WO | 2002/27530 | A2 | 4/2002 |
| WO | 2005/070289 | A1 | 8/2005 |
| WO | 2009/129402 | A1 | 10/2009 |
| WO | 2010/126825 | A1 | 11/2010 |
| WO | 2012/021507 | A2 | 2/2012 |
| WO | 2012/061438 | A2 | 5/2012 |
| WO | 2012/061440 | A2 | 5/2012 |
| WO | 2012/078079 | A2 | 6/2012 |
| WO | 2012/086910 | A1 | 6/2012 |
| WO | 2013/052789 | A1 | 4/2013 |
| WO | 2013/109762 | A1 | 7/2013 |
| WO | 2013/109777 | A1 | 7/2013 |

(56) References Cited

FOREIGN PATENT DOCUMENTS

| | | |
|---|---|---|
| WO | 2013/109916 A1 | 7/2013 |
| WO | 2013/169870 A1 | 11/2013 |
| WO | 2013/173838 A2 | 11/2013 |
| WO | 2014/200730 A1 | 12/2014 |
| WO | 2014/207294 A1 | 12/2014 |
| WO | 2015/027133 A1 | 2/2015 |
| WO | 2015/179592 A1 | 11/2015 |
| WO | 2015/198488 A1 | 12/2015 |
| WO | 2016/022203 A1 | 2/2016 |
| WO | 2016/036472 A1 | 3/2016 |
| WO | 2016/036582 A2 | 3/2016 |
| WO | 2017/037242 A1 | 3/2017 |
| WO | 2018/213066 A1 | 11/2018 |
| WO | 2018/222313 A1 | 12/2018 |
| WO | 2019/017508 A1 | 1/2019 |
| WO | 2019/024603 A1 | 2/2019 |
| WO | 2019/183422 A1 | 9/2019 |
| WO | 2019/217249 A2 | 11/2019 |
| WO | 2019/231982 A1 | 12/2019 |

OTHER PUBLICATIONS

Non-Final Office Action received for U.S. Appl. No. 16/994,352, dated Jul. 30, 2021, 11 pages.
Notice of Allowance received for Japanese Patent Application No. 2020-000492, dated Jul. 16, 2021, 4 pages (1 page of English Translation and 3 pages of Official Copy).
Final Office Action received for U.S. Appl. No. 17/031,859, dated Apr. 16, 2021, 14 pages.
Final Office Action received for U.S. Appl. No. 17/031,874, dated Apr. 16, 2021, 17 pages.
Notice of Allowance received for Japanese Patent Application No. 2019-162293, dated Apr. 9, 2021, 4 pages (1 page of English Translation and 3 pages of Official Copy).
Notice of Allowance received for U.S. Appl. No. 16/138,809, dated Apr. 16, 2021, 11 pages.
Office Action received for Danish Patent Application No. PA202170113, dated Apr. 15, 2021, 2 pages.
Advisory Action received for U.S. Appl. No. 14/732,773, dated Aug. 23, 2019, 6 pages.
Advisory Action received for U.S. Appl. No. 14/732,773, dated Nov. 9, 2018, 6 pages.
Advisory Action received for U.S. Appl. No. 14/839,922, dated Mar. 24, 2017, 4 pages.
Advisory Action received for U.S. Appl. No. 16/144,849, dated Aug. 12, 2019, 5 pages.
Advisory Action received for U.S. Appl. No. 16/144,864, dated Jul. 29, 2019, 6 pages.
Apple, "iPhone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Applicant-Initiated Interview Summary received for U.S. Appl. No. 15/600,243, dated Nov. 1, 2019, 6 pages.
Applicant-Initiated Interview Summary received for U.S. Appl. No. 15/608,848, dated Nov. 1, 2019, 3 pages.
Applicant-Initiated Interview Summary received for U.S. Appl. No. 15/627,069, dated Nov. 4, 2019, 6 pages.
Applicant-Initiated Interview Summary received for U.S. Appl. No. 15/705,849, dated Feb. 14, 2020, 3 pages.
Applicant-Initiated Interview Summary received for U.S. Appl. No. 16/144,849, dated Jan. 21, 2020, 6 pages.
Certificate of Examination received for Australian Patent Application No. 2018100158, dated Oct. 23, 2018, 2 pages.
Certificate of Examination received for Australian Patent Application No. 2018101855, dated Aug. 6, 2019, 2 pages.
Cho, H.S., "Satisfactory Innovative Smart-watch (fitbit force) . . . review after seven days of use, such as the amount of sleep and movement (improving sleep is the object of X-Blue", Online Available at: <https://x-blueuv.blogspot.com/2013/12/fitbit-force.html>, Dec. 3, 2013, 8 pages.
CNET, "Google Fit's automatic activity tracking is getting smarter on Android Wear", Available online at: https://www.youtube.com/watch?v=IttzlCid_d8, May 18, 2016, 1 page.
Codrington Simon, "Intuitive Scrolling Interfaces with CSS Scroll Snap Points", Online Available at: https://www.sitepoint.com/intuitive-scrolling-interfaces-with-css-scroll-snap-points/, Dec. 8, 2015, 14 pages.
Corrected Notice of Allowance received for U.S. Appl. No. 14/732,773, dated Feb. 10, 2020, 3 pages.
Corrected Notice of Allowance received for U.S. Appl. No. 15/183,663, dated Feb. 25, 2019, 3 pages.
Corrected Notice of Allowance received for U.S. Appl. No. 15/183,663, dated Mar. 27, 2019, 2 pages.
Corrected Notice of Allowance received for U.S. Appl. No. 15/600,243, dated Feb. 5, 2020, 3 pages.
Corrected Notice of Allowance received for U.S. Appl. No. 15/600,243, dated Mar. 13, 2020, 3 pages.
Corrected Notice of Allowance received for U.S. Appl. No. 15/600,243, dated Mar. 31, 2020, 5 pages.
DC Rainmaker, "Garmin Fenix3 New Auto Climb Functionality", Available online at: https://www.youtube.com/watch?v=iuavOSNpVRc, Feb. 19, 2015, 1 page.
Decision to Grant received for Danish Patent Application No. PA201870379, dated Jul. 5, 2019, 2 pages.
Decision to Refuse received for European Patent Application No. 13811085.3, dated Sep. 11, 2018, 21 pages.
Decision to Refuse received for European Patent Application No. 15771747.1, dated Aug. 10, 2018, 22 pages.
"DwProgressBarv2: Stepping and Events", davidwalsh.name/dwprogressbar-2-stepping-events-mootools-progress-bar, retrieved from the Wayback Machine, Aug. 31, 2008, 4 pages.
Evergreen et al., "Bar Chart", Better Evaluation, Available Online at: https://www.betterevaluation.org/en/evaluation-options/BarChart, Oct. 31, 2014, 8 pages.
Extended European Search Report received for European Patent Application No. 16837432.0, dated Mar. 11, 2019, 10 pages.
Extended European Search Report received for European Patent Application No. 18154145.9, dated Mar. 2, 2018, 8 pages.
Final Office Action received for U.S. Appl. No. 12/205,847, dated Apr. 25, 2012, 42 pages.
Final Office Action received for U.S. Appl. No. 14/732,773, dated Jul. 13, 2018, 48 pages.
Final Office Action received for U.S. Appl. No. 14/732,773, dated Jun. 21, 2019, 32 pages.
Final Office Action received for U.S. Appl. No. 14/839,922, dated Dec. 14, 2016, 22 pages.
Final Office Action received for U.S. Appl. No. 15/608,848, dated Jun. 26, 2019, 27 pages.
Final Office Action received for U.S. Appl. No. 15/627,069, dated Mar. 2, 2020, 22 pages.
Final Office Action received for U.S. Appl. No. 15/925,652, dated Aug. 1, 2019, 30 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
"Fitbit App", Available online at Khttp://web.archive.org/web/20180114083150/https://www.fitbit.com/au/app>, Jan. 14, 2018, 8 pages.
Garmin, "Fenix 5x Owner's Manual", Online Available at: https://web.archive.org/web/20180127170640/https://static.garmin.com/pumac/fenix5x_OM_EN.pdf, Jan. 27, 2018, 42 pages.
"Graphs and Charts", Online available at: <https://www.teachervision.com/lesson-planning/graph-chart-teacher-resources, retrieved on Dec. 12, 2018, 4 pages.
Intention to Grant received for Danish Patent Application No. PA201570668, dated Mar. 27, 2017, 2 pages.
Intention to Grant received for Danish Patent Application No. PA201870379, dated May 2, 2019, 2 pages.
International Preliminary Report on Patentability received for PCT Patent Application No. PCT/US2013/073195, dated Jun. 16, 2016, 10 pages.

(56) References Cited

OTHER PUBLICATIONS

International Preliminary Report on Patentability received for PCT Patent Application No. PCT/US2015/047282, dated Mar. 16, 2017, 26 pages.
International Preliminary Report on Patentability received for PCT Patent Application No. PCT/US2016/037686, dated Mar. 1, 2018, 12 pages.
International Preliminary Report on Patentability received for PCT Patent Application No. PCT/US2017/035554, dated Dec. 20, 2018, 39 pages.
International Preliminary Report on Patentability received for PCT Patent Application No. PCT/US2018/031662, dated Nov. 28, 2019, 12 pages.
International Search Report and Written Opinion received for PCT Patent Application No. PCT/US2015/047282, dated May 9, 2016, 33 pages.
International Search Report and Written Opinion received for PCT Patent Application No. PCT/US2016/037686, dated Sep. 9, 2016, 19 pages.
International Search Report and Written Opinion received for PCT Patent Application No. PCT/US2017/035554, dated Sep. 22, 2017, 42 pages.
International Search Report and Written Opinion received for PCT Patent Application No. PCT/US2018/031662, dated Sep. 27, 2018, 17 pages.
International Search Report and Written Opinion received for PCT Patent Application No. PCT/US2019/024570, dated Aug. 8, 2019, 18 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Pay Addition Fees and Partial International Search Report received for PCT Patent Application No. PCT/US2018/031662, dated Jul. 16, 2018, 13 pages.
Invitation to Pay Additional Fees received for PCT Patent Application No. PCT/US2015/047282, dated Dec. 22, 2015, 7 pages.
Invitation to Pay Additional Fees received for PCT Patent Application No. PCT/US2017/035554, dated Jul. 20, 2017, 2 pages.
Jenbsjourney, "Wondering About a Fitbit?", Available at: https://jenbsjourney.blogspot.kr/2013/08/wondering-about-fitbit.html, Aug. 6, 2013, 12 pages.
Minutes of Oral Proceedings received for European Patent Application No. 13811085.3, dated Sep. 11, 2018, 3 pages.
Minutes of Oral Proceedings received for European Patent Application No. 15771747.1, dated Aug. 10, 2018, 11 pages.
"Mugs", Online Available at: https://web.archive.org/web/20151029034349/http://le-mugs.com/, Oct. 29, 2015, 14 pages.
"Multi-Set Bar Chart", The Data Visualization Catalogue, Available Online at: https://datavizcatalogue.com/methods/multiset_barchart.html, Feb. 8, 2014, 3 pages.
"My CalStep", http://www.surprisesoftware.com/mycalstep/, Retrieved from the Wayback Machine, May 9, 2007, 2 pages.
Non-Final Office Action received for U.S. Appl. No. 15/608,848, dated Nov. 2, 2018, 21 pages.
Non-Final Office Action received for U.S. Appl. No. 12/205,847, dated Oct. 3, 2011, 59 pages.
Non-Final Office Action received for U.S. Appl. No. 14/732,773, dated Feb. 8, 2019, 32 pages.
Non-Final Office Action received for U.S. Appl. No. 14/732,773, dated Jan. 19, 2018, 45 pages.
Non-Final Office Action received for U.S. Appl. No. 14/839,916, dated Feb. 4, 2016, 19 pages.
Non-Final Office Action received for U.S. Appl. No. 14/839,916, dated May 1, 2017, 18 pages.
Non-Final Office Action received for U.S. Appl. No. 14/839,922, dated Aug. 17, 2016, 25 pages.
Non-Final Office Action received for U.S. Appl. No. 14/839,922, dated Feb. 25, 2016, 20 pages.
Non-Final Office Action received for U.S. Appl. No. 15/183,663, dated Jul. 9, 2018, 13 pages.
Non-Final Office Action received for U.S. Appl. No. 15/600,243, dated Jun. 27, 2019, 17 pages.
Non-Final Office Action received for U.S. Appl. No. 15/608,848, dated Feb. 6, 2020, 12 pages.
Non-Final Office Action received for U.S. Appl. No. 15/627,069, dated Jun. 21, 2019, 22 pages.
Non-Final Office Action received for U.S. Appl. No. 15/705,849, dated Nov. 12, 2019, 15 pages.
Non-Final Office Action received for U.S. Appl. No. 15/925,652, dated Apr. 5, 2019, 28 pages.
Non-Final Office Action received for U.S. Appl. No. 16/138,809, dated Feb. 28, 2020, 22 pages.
Non-Final Office Action received for U.S. Appl. No. 16/144,735, dated Feb. 19, 2020, 10 pages.
Non-Final Office Action received for U.S. Appl. No. 16/144,753, dated Mar. 5, 2020, 9 pages.
Non-Final Office Action received for U.S. Appl. No. 16/144,849, dated Dec. 31, 2018, 28 pages.
Non-Final Office Action received for U.S. Appl. No. 16/144,849, dated Sep. 17, 2019, 9 pages.
Non-Final Office Action received for U.S. Appl. No. 16/144,864, dated Dec. 18, 2018, 19 pages.
Non-Final Office Action received for U.S. Appl. No. 16/144,864, dated Jan. 31, 2020, 29 pages.
Notice of Acceptance received for Australian Patent Application No. 2015312215, dated Oct. 9, 2017, 3 pages.
Notice of Acceptance received for Australian Patent Application No. 2019201583, dated Jul. 15, 2019, 3 pages.
Notice of Allowance received for Chinese Patent Application No. 201580037927.5, dated Oct. 17, 2019, 3 pages.
Notice of Allowance received for Chinese Patent Application No. 201810105846.X, dated Feb. 18, 2020, 2 pages.
Notice of Allowance received for Danish Patent Application No. PA201570666, dated Sep. 15, 2016, 1 page.
Notice of Allowance received for Danish Patent Application No. PA201570668, dated Oct. 30, 2017, 2 pages.
Notice of Allowance received for Japanese Patent Application No. 2016-535045, dated Mar. 2, 2018, 4 pages.
Notice of Allowance received for Japanese Patent Application No. 2016-557650, dated Apr. 9, 2019, 4 pages.
Notice of Allowance received for Japanese Patent Application No. 2018-068846, dated Dec. 9, 2019, 4 pages.
Notice of Allowance received for Korean Patent Application No. 10-2016-7014577, dated May 30, 2019, 5 pages.
Notice of Allowance received for Korean Patent Application No. 10-2016-7033638, dated May 31, 2017, 5 pages.
Notice of Allowance received for Taiwanese Patent Application No. 104128685, dated May 3, 2017, 3 pages.
Notice of Allowance received for U.S. Appl. No. 12/205,847, dated Aug. 20, 2012, 13 pages.
Notice of Allowance received for U.S. Appl. No. 14/732,773, dated Dec. 18, 2019, 21 pages.
Notice of Allowance received for U.S. Appl. No. 14/839,916, dated Aug. 31, 2016, 11 pages.
Notice of Allowance received for U.S. Appl. No. 14/839,916, dated Jan. 10, 2018, 19 pages.
Notice of Allowance received for U.S. Appl. No. 14/839,922, dated Jan. 26, 2018, 2 pages.
Notice of Allowance received for U.S. Appl. No. 14/839,922, dated Jul. 6, 2017, 8 pages.
Notice of Allowance received for U.S. Appl. No. 14/839,922, dated Nov. 2, 2017, 8 pages.
Notice of Allowance received for U.S. Appl. No. 15/183,663, dated Jan. 17, 2019, 6 pages.
Notice of Allowance received for U.S. Appl. No. 15/600,243, dated Dec. 12, 2019, 7 pages.
Notice of Allowance received for U.S. Appl. No. 15/616,480, dated Jan. 3, 2019, 8 pages.
Notice of Allowance received for U.S. Appl. No. 16/144,671, dated Feb. 10, 2020, 17 pages.

(56) References Cited

OTHER PUBLICATIONS

Notice of Allowance received for U.S. Appl. No. 16/144,849, dated Mar. 6, 2020, 9 pages.
Office Action received for Australian Patent Application No. 2015312215, dated Oct. 13, 2016, 3 pages.
Office Action received for Australian Patent Application No. 2017100667, dated Aug. 3, 2017, 9 pages.
Office Action received for Australian Patent Application No. 2018100158, dated Apr. 23, 2018, 5 pages.
Office Action received for Australian Patent Application No. 2018101855, dated Feb. 22, 2019, 4 pages.
Office Action received for Australian Patent Application No. 2018200428, dated Mar. 7, 2018, 4 pages.
Office Action received for Australian Patent Application No. 2018200428, dated Nov. 15, 2018, 4 pages.
Office Action received for Australian Patent Application No. 2019100495, dated Mar. 6, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Chinese Patent Application No. 201380081349.6, dated Feb. 26, 2019, 12 pages.
Office Action received for Chinese Patent Application No. 201380081349.6, dated Jan. 16, 2020, 11 pages.
Office Action received for Chinese Patent Application No. 201380081349.6, dated Jul. 15, 2019, 10 pages.
Office Action received for Chinese Patent Application No. 201580037927.5, dated Apr. 22, 2019, 9 pages.
Office Action received for Chinese Patent Application No. 201580037927.5, dated Jul. 20, 2018, 21 pages.
Office Action received for Chinese Patent Application No. 201680047983.1, dated Mar. 18, 2019, 18 pages.
Office Action received for Chinese Patent Application No. 201680047983.1, dated Nov. 28, 2019, 9 pages.
Office Action received for Chinese Patent Application No. 201810105846.X, dated Aug. 27, 2019, 12 pages.
Office Action received for Chinese Patent Application No. 201810105846.X, dated Feb. 25, 2019, 10 pages.
Office Action received for Chinese Patent Application No. 201810105846.X, dated Nov. 28, 2019, 9 pages.
Office Action received for Danish Patent Application No. PA201570666, dated Feb. 2, 2016, 9 pages.
Office Action received for Danish Patent Application No. PA201570666, dated Jun. 27, 2016, 4 pages.
Office Action received for Danish Patent Application No. PA201570668, dated Apr. 8, 2016, 8 pages.
Office Action received for Danish Patent Application No. PA201570668, dated Sep. 9, 2016, 3 pages.
Office Action received for Danish Patent Application No. PA201670656, dated Jun. 14, 2017, 3 pages.
Office Action Received for Danish Patent Application No. PA201670656, dated May 2, 2019, 4 pages.
Office Action received for Danish Patent Application No. PA201670656, dated May 30, 2018, 5 pages.
Office Action received for Danish Patent Application No. PA201670656, dated Nov. 3, 2016, 8 pages.
Office Action received for Danish Patent Application No. PA201770191, dated Jan. 25, 2018, 3 pages.
Office Action received for Danish Patent Application No. PA201770191, dated Nov. 21, 2018, 4 pages.
Office Action received for Danish Patent Application No. PA201770191, dated Oct. 25, 2019, 4 pages.
Office Action received for Danish Patent Application No. PA201770423, dated Jun. 12, 2018, 7 pages.
Office Action received for Danish Patent Application No. PA201770423, dated Mar. 29, 2019, 6 pages.
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for European Patent Application No. 13811085.3, dated Apr. 20, 2018, 15 pages.
Office Action received for European Patent Application No. 15771747.1, dated Oct. 31, 2017, 7 pages.
Office Action received for European Patent Application No. 16837432.0, dated Jan. 10, 2020, 7 pages.
Office Action received for European Patent Application No. 17810749.6, dated Aug. 20, 2019, 9 pages.
Office Action received for European Patent Application No. 18154145.9, dated Apr. 3, 2018, 6 pages.
Office Action received for European Patent Application No. 19721883.7, dated Jan. 10, 2020, 4 pages.
Office Action received for German Patent Application No. 112015002326.7, dated Feb. 20, 2019, 7 pages.
Office Action received for Japanese Patent Application No. 2016-535045, dated May 12, 2017, 10 pages.
Office Action received for Japanese Patent Application No. 2016-557650, dated Apr. 13, 2018, 9 pages.
Office Action received for Japanese Patent Application No. 2016-557650, dated Aug. 10, 2017, 10 pages.
Office Action received for Japanese Patent Application No. 2016-557650, dated Nov. 9, 2018, 6 pages.
Office Action received for Japanese Patent Application No. 2018-014096, dated Jan. 6, 2020, 17 pages.
Office Action received for Japanese Patent Application No. 2018-014096, dated Jun. 29, 2018, 20 pages.
Office Action received for Japanese Patent Application No. 2018-014096, dated May 8, 2019, 14 pages.
Office Action received for Japanese Patent Application No. 2018-014096, dated Nov. 6, 2018, 15 pages.
Office Action received for Japanese Patent Application No. 2018-068846, dated Jan. 8, 2019, 6 pages.
Office Action received for Japanese Patent Application No. 2019-162293, dated Jan. 31, 2020, 8 pages.
Office Action received for Korean Patent Application No. 10-2016-7014577, dated Dec. 26, 2017, 14 pages.
Office Action received for Korean Patent Application No. 10-2016-7014577, dated Oct. 31, 2018, 11 pages.
Office Action received for Korean Patent Application No. 10-2016-7033638, dated Jan. 31, 2017, 6 pages.
Office Action received for Korean Patent Application No. 10-2019-7025538, dated Feb. 17, 2020, 12 pages.
Office Action received for Korean Patent Application No. 10-2019-7025781, dated Nov. 26, 2019, 10 pages.
Office Action received for Taiwanese Patent Application No. 104128685, dated Jan. 4, 2017, 40 pages.
Partial Supplementary European Search Report received for European Patent Application No. 17810749.6, dated Apr. 25, 2019, 8 pages.
Razykdreviews, "In Depth Review of Apple Watch Activity and Workout App", available at <URL: https://www.youtube.com/watch?v=GkKl3qlK0ow>, Category: X Claims: 1-5 Category: L Reason: Internet citation/video, May 11, 2015, 1 page.
Rizknows, "Garmin Connect Mobile App—Review #2", https://www.youtube.com/watch?v=7my3wMpeRbE, Category: X Claims: 1-5 Category: L Reason: Internet citation/video, Oct. 22, 2015, 1 page.
Rizknows, "Tom Tom Multisport Cardio Review", Online available at: https://www.youtube.com/watch?v=WoVCzLrSN9A, Sep. 4, 2015, 1 page.
Search Report and Opinion received for Danish Patent Application No. PA201770191, dated Jun. 30, 2017, 9 pages.

(56) References Cited

OTHER PUBLICATIONS

Search Report and Opinion received for Danish Patent Application No. PA201770423, dated Oct. 4, 2017, 10 pages.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Smith, "Garmin Fenix 5 Activity/Smart Watch Review", Online Available at: https://www.youtube.com/watch?v=6PkQxXQxpoU, Sep. 2, 2017, 1 page.
Sportstechguides, "Garmin Fenix 5: How to Add Power Data Fields", Online Available at: https://www.youtube.com/watch?v=ZkPptnnXEiQ, Apr. 29, 2017, 2 pages.
Sportstechguides, "Garmin Fenix 5: How To Set Up Run Alerts", Online Available at: https://www.youtube.com/watch?v=gSMwv8vlhB4, May 13, 2017, 2 pages.
Summons to Attend Oral Proceedings received for European Patent Application No. 13811085.3, dated Jan. 26, 2018, 14 pages.
Summons to Attend Oral Proceedings received for European Patent Application No. 15771747.1, dated May 25, 2018, 17 pages.
Supplemental Notice of Allowance received for U.S. Appl. No. 15/616,480, dated Mar. 28, 2019, 2 pages.
Supplementary European Search Report received for European Patent Application No. 17810749.6, dated Aug. 6, 2019, 6 pages.
"Suunto Spartan Trainer Wrist HR 1.12", Online Available at:- https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Available at https://www.youtube.com/watch?v=aixfoCnSOOU, Mar. 19, 2018, 2 pages.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
Tomtom, "TomTom Runner & Multi-Sport Reference Guide", Online available at: https://web.archive.org/web/20150908075934/http://download.tomtom.com/open/manuals/Runner_Multi-Sport/refman/TomTom-Runner-Multi-Sport-RG-en-GB.pdf, Sep. 8, 2015, 44 pages.
"Utilization of Galaxy S4—S Health", ChatOn and Samsung Hub, Available at http://seeit.kr/1263, Jun. 12, 2013, 25 pages.
"Visual Pace Alarm app", Available Online at: https://apps.garmin.com/en-US/apps/3940f3a2-4847-4078-a911-d77422966c82, Oct. 19, 2016, 1 page.
Wesley, "Apple Watch Series 1", Online available at: http://tool-box.info/blog/archives/1737-unknown.html, May 28, 2015, 5 pages.
Youtube, "Apple Watch Series 3", Online available at: https://www.youtube.com/watch?v=iBPr9gEfkK8, Nov. 21, 2017, 15 pages.
Zlelik, "Garmin Fenix 5 Open Water Swimming Activity Demo", Online Available at: https://www.youtube.com/watch?v=iSVhdvw2dcs, Jun. 9, 2017, 1 page.
Non-Final Office Action received for U.S. Appl. No. 17/192,161, dated May 13, 2021, 28 pages.
Notice of Allowance received for Chinese Patent Application No. 201680047983.1, dated Apr. 28, 2021, 3 pages (1 page of English Translation and 2 pages of Official Copy).
Notice of Allowance received for U.S. Appl. No. 16/377,892, dated May 24, 2021, 9 pages.
Summons to Oral Proceedings received for European Patent Application No. 15771747.1, dated Apr. 29, 2021, 8 pages.
Bagala et al., "Evaluation of Accelerometer-Based Fall Detection Algorithms on Real-World Falls", PloS ONE, vol. 7, No. 5, May 16, 2012, 9 pages.
Office Action received for European Patent Application No. 20182116.2, dated Nov. 6, 2020, 9 pages.
Office Action received for Korean Patent Application No. 10-2019-7025781, dated Oct. 30, 2020, 10 pages (4 pages of English Translation and 6 pages of Official Copy).
Applicant-Initiated Interview Summary received for U.S. Appl. No. 16/377,892, dated Oct. 13, 2020, 5 pages.

Applicant-Initiated Interview Summary received for U.S. Appl. No. 16/378,136, dated Oct. 13, 2020, 4 pages.
Non-Final Office Action received for U.S. Appl. No. 16/894,309, dated Oct. 15, 2020, 24 pages.
Notice of Allowance received for U.S. Appl. No. 16/144,864, dated Sep. 29, 2020, 2 pages.
Notice of Allowance received for U.S. Appl. No. 16/556,023, dated Oct. 15, 2020, 8 pages.
Result of Consultation received for European Patent Application No. 19721883.7, dated Oct. 7, 2020, 3 pages.
Applicant-Initiated Interview Summary received for U.S. Appl. No. 16/820,383, dated Mar. 11, 2021, 2 pages.
Notice of Acceptance received for Australian Patent Application No. 2019250251, dated Feb. 18, 2021, 3 pages.
Notice of Allowance received for U.S. Appl. No. 15/925,652, dated Mar. 9, 2021, 9 pages.
Notice of Allowance received for U.S. Appl. No. 16/144,864, dated Mar. 12, 2021, 2 pages.
Office Action received for Chinese Patent Application No. 202010606407.4, dated Jan. 27, 2021, 16 pages (7 pages of English Translation and 9 pages of Official Copy).
Office Action received for Japanese Patent Appiication No. 2019-563407, dated Feb. 5, 2021, 5 pages (2 pages of English Translation and 3 pages of Official Copy).
Applicant-Initiated Interview Summary received for U.S. Appl. No. 16/894,309, dated Jun. 25, 2021, 4 pages.
Applicant-Initiated Interview Summary received for U.S. Appl. No. 17/031,859, dated Jun. 30, 2021, 4 pages.
Applicant-Initiated Interview Summary received for U.S. Appl. No. 17/031,874, dated Jun. 30, 2021, 4 pages.
Applicant-Initiated Interview Summary received for U.S. Appl. No. 17/192,161, dated Jun. 29, 2021, 4 pages.
Decision to Grant received for Danish Patent Application No. PA201670656, dated Jun. 21, 2021, 2 pages.
Decision to Grant received for German Patent Application No. 112015002326.7, dated Jun. 15, 2021, 10 pages (1 page of English Translation and 9 pages of Official Copy).
European Search Report received for European Patent Application No. 21165295.3, dated Jun. 18, 2021, 4 pages.
Notice of Allowance received for U.S. Appl. No. 15/627,069, dated Jun. 17, 2021, 14 pages.
Office Action received for Chinese Patent Application No. 202010606407.4, dated Jun. 2, 2021, 12 pages (5 pages of English Translation and 7 pages of Official Copy).
Office Action received for European Patent Application No. 19721883.7, dated Jun. 15, 2021, 9 pages.
Office Action received for European Patent Application No. 21165295.3, dated Jul. 1, 2021, 10 pages.
Non-Final Office Action received for U.S. Appl. No. 17/031,874, dated Dec. 28, 2020, 14 pages.
Result of Consultation received for European Patent Application No. 17810749.6, dated Dec. 15, 2020, 3 pages.
Non-Final Office Action received for U.S. Appl. No. 15/608,848, dated Feb. 12, 2021, 14 pages.
Notice of Allowance received for U.S. Appl. No. 16/144,753, dated Feb. 10, 2021, 8 pages.
Notice of Allowance received for U.S. Appl. No. 16/144,864, dated Feb. 9, 2021, 13 pages.
Supplemental Notice of Allowance received for U.S. Appl. No. 15/925,652, dated Feb. 17, 2021, 3 pages.
CBS This Morning, "This smart mirror puts a personal trainer in your reflection", Available at: https://www.youtube.com/watch?v=nSmTTZcpVGg, Oct. 13, 2018, 4 pages.
Notice of Allowance received for U.S. Appl. No. 16/377,892, dated Sep. 9, 2021, 9 pages.
Notice of Allowance received for U.S. Appl. No. 16/378,136, dated Sep. 22, 2021, 7 pages.
Office Action received for Australian Patent Application No. 2020239743, dated Sep. 3, 2021, 4 pages.
Office Action received for Japanese Patent Application No. 2019-044107, dated Jul. 30, 2021, 9 pages (5 pages of English Translation and 4 pages of Official Copy).

(56) References Cited

OTHER PUBLICATIONS

Office Action received for Korean Patent Application No. 10-2021-7026284, dated Aug. 31, 2021, 10 pages (4 pages of English Translation and 6 pages of Official Copy).
Applicant Initiated Interview Summary received for U.S. Appl. No. 15/608,848, dated Oct. 26, 2020, 3 pages.
Applicant-Initiated Interview Summary received for U.S. Appl. No. 15/925,652, dated Nov. 3, 2020, 4 pages.
Applicant-Initiated Interview Summary received for U.S. Appl. No. 16/144,753, dated Nov. 4, 2020, 3 pages.
European Search Report received for European Patent Application No. 20182116.2, dated Oct. 21, 2020, 4 pages.
Final Office Action received for U.S. Appl. No. 15/627,069, dated Oct. 20, 2020, 25 pages.
Notice of Allowance received for U.S. Appl. No. 15/705,849, dated Oct. 16, 2020, 14 pages.
Notice of Allowance received for U.S. Appl. No. 16/144,735, dated Oct. 28, 2020, 13 pages.
Office Action received for Japanese Patent Application No. 2020-104679, dated Sep. 18, 2020, 13 pages (7 pages of English Translation and 6 pages of Official Copy).
Applicant-Initiated Interview Summary received for U.S. Appl. No. 16/138,809, dated Dec. 16, 2020, 7 pages.
Board Decision received for Chinese Patent Application No. 201380081349.6, dated Nov. 23, 2020, 2 pages (1 page of English Translation and 1 page of Official Copy).
Non-Final Office Action received for U.S. Appl. No. 16/820,383, dated Dec. 14, 2020, 11 pages.
Non-Final Office Action received for U.S. Appl. No. 17/031,859, dated Dec. 15, 2020, 13 pages.
Notice of Allowance received for U.S. Appl. No. 16/144,753, dated Dec. 4, 2020, 22 pages.
Advisory Action received for U.S. Appl. No. 16/377,892, dated Apr. 9, 2021, 4 pages.
Advisory Action received for U.S. Appl. No. 16/378,136, dated Apr. 12, 2021, 4 pages.
Applicant Initiated Interview Summary received for U.S. Appl. No. 15/608,848, dated Apr. 13, 2021, 4 pages.
Notice of Acceptance received for Australian Patent Application No. 2021200787, dated Mar. 19, 2021, 3 pages.
Office Action received for Japanese Patent Application No. 2018-184532, dated Mar. 1, 2021, 11 pages (6 pages of English Translation and 5 pages of Official Copy).
Communication of the Board of Appeal received for European Patent Application No. 15771747.1, dated Aug. 25, 2021, 9 pages.
Notice of Allowance received for Japanese Patent Application No. 2019-563407, dated Aug. 20, 2021, 4 pages (1 page of English Translation and 3 pages of Official Copy).
Notice of Allowance received for Korean Patent Application No. 10-2020-7026035, dated Aug. 23, 2021, 4 pages (2 page of English Translation and 2 pages of Official Copy).
Office Action received for Australian Patent Application No. 2020239748, dated Sep. 1, 2021, 4 pages.
Office Action received for European Patent Application No. 21168916.1, dated Aug. 23, 2021, 8 pages.
Applicant Initiated Interview Summary received for U.S. Appl. No. 16/894,309, dated Jan. 26, 2021, 3 pages.
Adeniyi Samuel, "How to connect a second PS4 controller to a PlayStation 4 console", Online available on:- https://www.youtube.com/watch?v=mOZX_SrNISE, May 28, 2017, 2 pages.
Allison Conor, "Working out with Fiit's wearable-powered boutique fitness classes", Online available at: - <https://www.wareable.com/wearable-tech/fiit-fitness-classes-review-3849>, May 14, 2018, 8 pages.
Applicant-Initiated Interview Summary received for U.S. Appl. No. 15/627,069, dated Jan. 22, 2021, 4 pages.
Decision to Refuse received for European Patent Application No. 17810749.6, dated Jan. 29, 2021, 24 pages.
Extended European Search Report received for European Patent Application No. 20203526.7, dated Jan. 29, 2021, 13 pages.

Final Office Action received for U.S. Appl. No. 16/377,892, dated Jan. 28, 2021, 11 pages.
Final Office Action received for U.S. Appl. No. 16/378,136, dated Jan. 28, 2021, 9 pages.
Hamilton Jim, "Peloton Tips", Online available on: - <https://www.youtube.com/watch?app=desktop&v=OneXtB0kaD4>, Oct. 22, 2015, 3 pages.
Intention to Grant received for Danish Patent Application No. PA201670656, dated Jan. 18, 2021, 2 pages.
Minutes of the Oral Proceedings received for European Patent Application No. 17810749.6, dated Jan. 26, 2021, 8 pages.
Notice of Allowance received for Chinese Patent Application No. 201710439448.7, dated Jan. 26, 2021, 2 pages (1 page of English Translation and 1 page of Official Copy).
Office Action received for European Patent Application No. 16837432.0, dated Jan. 27, 2021, 7 pages.
Office Action received for Japanese Patent Application No. 2020-000492, dated Dec. 11, 2020, 6 pages (3 pages English Translation and 3 pages of Official Copy).
Office Action received for Korean Patent Application No. 10-2019-7033834, dated Jan. 22, 2021, 13 pages (6 pages of English Translation and 7 pages of Official Copy).
Result of Consultation received for European Patent Application No. 17810749.6, dated Jan. 18, 2021, 3 pages.
Result of Consultation received for European Patent Application No. 17810749.6, dated Jan. 21, 2021, 18 pages.
Supplemental Notice of Allowance received for U.S. Appl. No. 15/925,652, dated Jan. 26, 2021, 3 pages.
Supplemental Notice of Allowance received for U.S. Appl. No. 16/556,023, dated Feb. 3, 2021, 2 pages.
Vicky's Blog, "Howto Log in to PS4 Automatically with Particular User?", Online available on: - https://www.youtube.com/watch?v=kqdlzXAvOkY, May 30, 2018, 3 pages.
Yoyodavid, "Howto Use Multiple Accounts on the PlayStation 4", Online available at: -https://www.youtube.com/watch?v=5V21obRMeKE, Jan. 9, 2014, 3 pages.
Final Office Action received for U.S. Appl. No. 16/144,753, dated Sep. 22, 2020, 9 pages.
International Search Report and written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Danish Patent Application No. PA201970532, dated May 29, 2020, 3 pages.
Office Action received for Japanese Patent Application No. 2018-014096, dated Aug. 28, 2020, 4 pages (2 pages of English Translation and 2 pages of Official Copy).
Search Report and Opinion received for Danish Patent Application No. PA201970532, dated Nov. 8, 2019, 9 pages.
Summons to Attend Oral Proceedings received for European Patent Application No. 18154145.9, dated Sep. 17, 2020, 11 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
Applicant-Initiated Interview Summary received for U.S. Appl. No. 17/192,161, dated Sep. 29, 2021, 3 pages.
Corrected Notice of Allowance received for U.S. Appl. No. 16/820,383, dated Oct. 5, 2021, 2 pages.
Final Office Action received for U.S. Appl. No. 17/030,318, dated Sep. 30, 2021, 28 pages.

(56) References Cited

OTHER PUBLICATIONS

International Search Report and Written Opinion received for PCT Patent Application No. PCT/US2021/017736, dated Sep. 2, 2021,25 pages.
Non-Final Office Action received for U.S. Appl. No. 16/418,786, dated Oct. 4, 2021, 10 pages.
Office Action received for Danish Patent Application No. PA202070613, dated Sep. 30, 2021, 4 pages.
Office Action received for Danish Patent Application No. PA202070614, dated Sep. 28, 2021, 4 pages,.
Applicant Initiated Interview Summary received for U.S. Appl. No. 17/030,318, dated Jul. 30, 2021, 4 pages.
Applicant Initiated Interview Summary received for U.S. Appl. No. 17/030,321, dated Jul. 30, 2021, 2 pages.
Corrected Notice of Allowance received for U.S. Appl. No. 16/377,892, dated Aug. 11, 2021, 3 pages.
Corrected Notice of Allowance received for U.S. Appl. No. 16/378,136, dated Aug. 11, 2021, 2 pages.
Corrected Notice of Allowance received for U.S. Appl. No. 16/820,383, dated Aug. 13, 2021, 2 pages.
Corrected Notice of Allowance received for U.S. Appl. No. 16/820,383, dated Aug. 19, 2021, 2 pages.
Final Office Action received for U.S. Appl. No. 17/030,321, dated Apr. 2, 2021, 28 pages.
Final Office Action received for U.S. Appl. No. 17/192,161, dated Aug. 16, 2021, 22 pages.
Gym Book—Strength Training Planner, Logger and Analyzer, GymBookApp, Available Online at: https://web.archive.org/web/20160401104508/https://gymbookapp.com/, Apr. 1, 2016, 10 pages.
Invitation to Pay Additional Fees received for PCT Patent Application No. PCT/US2021/017736, dated Jun. 15, 2021, 14 pages.
Non-Final Office Action received for U.S. Appl. No. 17/030,318, dated Apr. 2, 2021, 28 pages.
Non-Final Office Action received for U.S. Appl. No. 17/030,318, dated Dec. 3, 2020, 22 pages.
Non-Final Office Action received for U.S. Appl. No. 17/030,321, dated Dec. 15, 2020, 25 pages.
Notice of Acceptance received for Australian Patent Application No. 2020256383, dated Aug. 3, 2021, 3 pages.
Notice of Allowance received for U.S. Appl. No. 15/608,848, dated Aug. 25, 2021, 9 pages.
Office Action received for Australian Patent Application No. 2020239743, dated Mar. 25, 2021, 8 pages.
Office Action received for Australian Patent Application No. 2020239748, dated Apr. 21, 2021, 6 pages.
Office Action received for Australian Patent Application No. 2020239752, dated Jun. 4, 2021, 8 pages.
Office Action received for Chinese Patent Application No. 201780034203.4, dated Jul. 14, 2021, 12 pages (5 pages of English Translation and 7 pages of Official Copy).
Search Report and Opinion received for Danish Patent Application No. PA202070612, dated Jun. 7, 2021, 9 pages.
Search Report and Opinion received for Danish Patent Application No. PA202070613, dated Jan. 22, 2021, 9 pages.
Search Report and Opinion received for Danish Patent Application No. PA202070615, dated Jan. 22, 2021, 9 pages.
Search Report and Opinion received for Danish Patent Application No. PA202070616, dated Feb. 3, 2021, 8 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2020/035199, dated Oct. 30, 2020, 20 pages.
Invitation to Pay Additional Fees received for PCT Patent Application No. PCT/US2020/035199, dated Sep. 8, 2020, 12 pages.
Notice of Allowance received for U.S. Appl. No. 15/925,652, dated Nov. 20, 2020, 9 pages.

Office Action received for Chinese Patent Application No. 201710439448.7, dated Oct. 10, 2020, 19 pages (8 pages of English Translation and 11 pages of Official Copy).
Result of Consultation received for European Patent Application No. 18154145.9, dated Nov. 30, 2020, 17 pages.
Corrected Notice of Allowance received for U.S. Appl. No. 16/378,136, dated Jun. 11, 2021, 2 pages.
Notice of Allowance received for U.S. Appl. No. 16/378,136, dated Jun. 3, 2021, 7 pages.
Office Action received for Australian Patent Application No. 2020256383, dated Jun. 4, 2021, 3 pages.
Office Action received for European Patent Application No. 20182116.2, dated May 25, 2021, 9 pages.
Office Action received for Japanese Patent Application No. 2020-115940, dated May 7, 2021, 3 pages (1 page of English Translation and 2 pages of Official Copy).
European Search Report received for European Patent Application No. 21168916.1, dated Jul. 14, 2021, 5 pages.
Notice of Allowance received for Korean Patent Application No. 10-2019-7025781, dated Jun. 29, 2021, 5 pages (2 pages of English Translation and 3 pages of Official Copy).
Notice of Allowance received for Korean Patent Application No. 10-2019-7033834, dated Jul. 3, 2021, 4 pages (2 page of English Translation and 2 pages of Official Copy).
Notice of Allowance received for U.S. Appl. No. 16/138,809, dated Jul. 20, 2021, 6 pages.
Notice of Allowance received for U.S. Appl. No. 16/820,383, dated Jul. 21, 2021, 11 pages.
Office Action received for Chinese Patent Application No. 201380081349.6, dated Jun. 2, 2021, 17 pages (8 pages of English Translation and 9 pages of Official Copy).
Office Action received for Chinese Patent Application No. 201910858933.7, dated Jun. 29, 2021, 8 pages (3 pages of English Translation and 5 pages of Official Copy).
Supplemental Notice of Allowance received for U.S. Appl. No. 15/627,069, dated Jul. 12, 2021, 2 pages.
Final Office Action received for U.S. Appl. No. 17/192,161, dated Oct. 18, 2021, 22 pages.
Non-Final Office Action received for U.S. Appl. No. 17/030,321, dated Oct. 18, 2021, 28 pages.
Notice of Allowance received for Japanese Patent Application No. 2020-115940, dated Oct. 22, 2021, 4 pages (1 page of English Translation and 3 pages of Official Copy).
Notice of Allowance received for U.S. Appl. No. 15/608,848, dated Oct. 29, 2021, 7 pages.
Office Action received for Australian Patent Application No. 2020239752, dated Oct. 25, 2021, 5 pages.
Office Action received for Chinese Patent Application No. 201780034203.4, dated Sep. 24, 2021, 7 pages (3 pages of English Translation and 4 pages of Official Copy).
Office Action received for Danish Patent Application No. PA202070815, dated Oct. 18, 2021, 2 pages.
Office Action received for Korean Patent Application No. 10-2021-7031939, dated Oct. 19, 2021, 11 pages (5 pages of English Translation and 6 pages of Official Copy).
Applicant-Initiated Interview Summary received for U.S. Appl. No. 17/031,859, dated Feb. 26, 2021, 4 pages.
Applicant-Initiated Interview Summary received for U.S. Appl. No. 17/031,874, dated Feb. 26, 2021, 4 pages.
Decision to Refuse received for European Patent Application No. 18154145.9, dated Feb. 17, 2021, 20 pages.
Final Office Action received for U.S. Appl. No. 16/894,309, dated Feb. 24, 2021, 30 pages.
Minutes of the Oral Proceedings received for European Patent Application No. 18154145.9, dated Feb. 12, 2021, 8 pages.
Notice of Acceptance received for Australian Patent Application No. 2017277971, dated Feb. 17, 2021, 3 pages.
Office Action received for Chinese Patent Application No. 201380081349.6, dated Jan. 5, 2021, 16 pages (7 pages of English Translation and 9 pages of Official Copy).
Office Action received for Chinese Patent Application No. 201680047983.1, dated Feb. 1, 2021, 6 pages (3 pages of English Translation and 3 pages of Official Copy).

(56) References Cited

OTHER PUBLICATIONS

Office Action received for Korean Patent Application No. 10-2020-7026035, dated Feb. 19, 2021, 13 pages (6 pages of English Translation and 7 pages of Official Copy).
Final Office Action received for U.S. Appl. No. 16/418,786, dated Jan. 13, 2021, 14 pages.
Notice of Acceptance received for Australian Patent Application No. 2018268972, dated Dec. 18, 2020, 3 pages.
Notice of Allowance received for Japanese Patent Application No. 2018-014096, dated Jan. 5, 2021, 3 pages (1 page of English Translation and 2 pages of Official Copy).
Notice of Allowance received for Japanese Patent Application No. 2020-104679, dated Jan. 4, 2021, 4 pages (1 page of English Translation and 3 pages of Official Copy).
Notice of Allowance received for U.S. Appl. No. 16/556,023, dated Jan. 13, 2021, 8 pages.
Search Report and Opinion received for Danish Patent Application No. PA202070614, dated Jan. 14, 2021, 9 pages.
Supplemental Notice of Allowance received for U.S. Appl. No. 15/925,652, dated Jan. 6, 2021, 2 pages.
Advisory Action received for U.S. Appl. No. 16/144,864, dated Jul. 6, 2020, 6 pages.
Applicant-Initiated Interview Summary received for U.S. Appl. No. 15/608,848, dated May 12, 2020, 5 pages.
Applicant-Initiated Interview Summary received for U.S. Appl. No. 15/627,069, dated Jul. 20, 2020, 5 pages.
Applicant-Initiated Interview Summary received for U.S. Appl. No. 15/705,849, dated Jun. 29, 2020, 3 pages.
Applicant-Initiated Interview Summary received for U.S. Appl. No. 16/138,809, dated Jun. 9, 2020, 4 pages.
Applicant-Initiated Interview Summary received for U.S. Appl. No. 16/144,735, dated Jun. 18, 2020, 3 pages.
Applicant-Initiated Interview Summary received for U.S. Appl. No. 16/144,753, dated Jun. 18, 2020, 3 pages.
Applicant-Initiated Interview Summary received for U.S. Appl. No. 16/144,864, dated Apr. 29, 2020, 4 pages.
Applicant-Initiated Interview Summary received for U.S. Appl. No. 16/144,864, dated Jun. 22, 2020, 3 pages.
Corrected Notice of Allowance received for U.S. Appl. No. 14/732,773, dated Mar. 24, 2020, 3 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Final Office Action received for U.S. Appl. No. 15/608,848, dated Aug. 21, 2020, 15 pages.
Final Office Action received for U.S. Appl. No. 15/705,849, dated May 1, 2020, 17 pages.
Final Office Action received for U.S. Appl. No. 16/138,809, dated Aug. 27, 2020, 24 pages.
Final Office Action received for U.S. Appl. No. 16/144,735, dated May 4, 2020, 12 pages.
Final Office Action received for U.S. Appl. No. 16/144,864, dated May 28, 2020, 29 pages.
Non-Final Office Action received for U.S. Appl. No. 15/627,069, dated May 26, 2020, 25 pages.
Non-Final Office Action received for U.S. Appl. No. 15/925,652, dated Aug. 7, 2020, 39 pages.
Non-Final Office Action received for U.S. Appl. No. 16/377,892, dated May 21, 2020, 9 pages.
Non-Final Office Action received for U.S. Appl. No. 16/378,136, dated Jun. 2, 2020, 8 pages.
Non-Final Office Action received for U.S. Appl. No. 16/418,786, dated Apr. 24, 2020, 16 pages.
Notice of Acceptance received for Australian Patent Application No. 2019222943, dated May 5, 2020, 3 pages.
Notice of Acceptance received for Australian Patent Application No. 2020204153, dated Jul. 6, 2020, 3 pages.
Notice of Allowance received for U.S. Appl. No. 15/705,849, dated Jul. 28, 2020, 10 pages.
Notice of Allowance received for U.S. Appl. No. 16/144,735, dated Jul. 21, 2020, 13 pages.
Notice of Allowance received for U.S. Appl. No. 16/144,849, dated Apr. 17, 2020, 2 pages.
Notice of Allowance received for U.S. Appl. No. 16/144,864, dated Jul. 28, 2020, 27 pages.
Office Action received for Australian Patent Application No. 2017277971, dated Aug. 12, 2020, 3 pages.
Office Action received for Australian Patent Application No. 2017277971, dated Jun. 3, 2020, 3 pages.
Office Action received for Australian Patent Application No. 2018268972, dated Jul. 9, 2020, 4 pages.
Office Action received for Australian Patent Application No. 2019100495, dated Mar. 16, 2020, 3 pages.
Office Action received for Australian Patent Application No. 2019250251, dated Aug. 6, 2020, 3 pages.
Office Action received for Chinese Patent Application No. 201380081349.6, dated Jul. 15, 2020, 9 pages (4 pages of English Translation and 5 pages of Official Copy).
Office Action received for Chinese Patent Application No. 201680047983.1, dated Jul. 1, 2020, 6 pages (3 pages of English Translation and 3 pages of Official Copy).
Office Action received for Chinese Patent Application No. 201710439448.7, dated Mar. 27, 2020, 13 pages (7 pages of English Translation and 6 pages of Official Copy).
Office Action received for Chinese Patent Application No. 201910858933.7, dated Aug. 18, 2020, 14 pages (7 pages of English Translation and 7 pages of Official Copy).
Office Action received for Danish Patent Application No. PA201670656, dated Jul. 1, 2020, 4 pages.
Office Action received for European Patent Application No. 19721883.7, dated May 28, 2020, 11 pages.
Office Action received for Japanese Patent Application No. 2019-044107, dated May 29, 2020, 6 pages (3 pages of English Translation and 3 pages of Official Copy).
Office Action received for Japanese Patent Application No. 2019-162293, dated Jul. 27, 2020, 9 pages (5 pages of English Translation and 4 pages of Official Copy).
Office Action received for Korean Patent Application No. 10-2019-7025538, dated Aug. 15, 2020, 8 pages (4 pages of English Translation and 4 pages of Official Copy).
Result of Consultation received for European Patent Application No. 18154145.9, dated Sep. 4, 2020, 3 pages.
Summons to Attend Oral Proceedings received for European Patent Application No. 17810749.6, dated Aug. 12, 2020, 11 pages.
Supplemental Notice of Allowance received for U.S. Appl. No. 16/144,849, dated Mar. 31, 2020, 2 pages.
Applicant-Initiated Interview Summary received for U.S. Appl. No. 16/377,892, dated Mar. 26, 2021, 2 pages.
Applicant-Initiated Interview Summary received for U.S. Appl. No. 16/378,136, dated Mar. 26, 2021, 2 pages.
Applicant-Initiated Interview Summary received for U.S. Appl. No. 16/418,786, dated Mar. 30, 2021, 4 pages.
Decision on Appeal received for Korean Patent Application No. 10-2019-7025538, dated Feb. 24, 2021, 20 pages (4 pages of English Translation and 16 pages of Official Copy).
Non-Final Office Action received for U.S. Appl. No. 16/888,629, dated Mar. 31, 2021, 14 pages.
Notice of Allowance received for Korean Patent Application No. 10-2019-7025538, dated Mar. 10, 2021, 5 pages (2 pages of English Translation and 3 pages of Official Copy).
Notice of Allowance received for U.S. Appl. No. 16/144,864, dated Mar. 30, 2021, 2 pages.
Notice of Allowance received for U.S. Appl. No. 16/820,383, dated Mar. 31, 2021, 11 pages.
Office Action received for European Patent Application No. 18727543.3, dated Mar. 26, 2021, 7 pages.
Search Report and Opinion received for Danish Patent Application No. PA202070815, dated Mar. 16, 2021, 8 pages.
Applicant Initiated Interview Summary received for U.S. Appl. No. 16/994,352, dated Nov. 2, 2021, 4 pages.
Notice of Allowance received for U.S. Appl. No. 16/888,629, dated Nov. 9, 2021, 11 pages.

(56) References Cited

OTHER PUBLICATIONS

Notice of Allowance received for U.S. Appl. No. 16/894,309, dated Nov. 5, 2021, 12 pages.
Office Action received for European Patent Application No. 20721342.2, dated Nov. 4, 2021, 9 pages.
Corrected Notice of Allowance received for U.S. Appl. No. 17/157,728, dated Apr. 4, 2022, 3 pages.
Non-Final Office Action received for U.S. Appl. No. 17/031,543, dated Apr. 1, 2022, 9 pages.
Non-Final Office Action received for U.S. Appl. No. 17/381,570, dated Apr. 1, 2022, 29 pages.
Notice of Acceptance received for Australian Patent Application No. 2021201130, dated Mar. 28, 2022, 3 pages.
Notice of Allowance received for Japanese Patent Application No. 2020-160054, dated Apr. 4, 2022, 4 pages (1 page of English Translation and 3 pages of Official Copy).
Notice of Allowance received for Korean Patent Application No. 10-2021-7031939, dated Apr. 5, 2022, 5 pages (1 page of English Translation and 4 pages of Official Copy).
Notice of Allowance received for U.S. Appl. No. 17/030,321, dated Apr. 1, 2022, 8 pages.
Office Action received for Australian Patent Application No. 2021203636, dated Mar. 23, 2022, 3 pages.
Supplemental Notice of Allowance received for U.S. Appl. No. 16/894,309, dated Apr. 8, 2022, 3 pages.
Supplemental Notice of Allowance received for U.S. Appl. No. 17/030,318, dated Apr. 4, 2022, 2 pages.
International Preliminary Report on Patentability received for PCT Patent Application No. PCT/US2020/025997, dated Nov. 18, 2021, 10 pages.
Non-Final Office Action received for U.S. Appl. No. 17/157,728, dated Nov. 26, 2021, 18 pages.
Office Action received for Danish Patent Application No. PA202070615, dated Nov. 16, 2021, 4 pages.
Office Action received for European Patent Application No. 20203526.7, dated Nov. 23, 2021, 9 pages.
Corrected Notice of Allowance received for U.S. Appl. No. 17/192,161, dated Mar. 23, 2022, 2 pages.
Non-Final Office Action received for U.S. Appl. No. 16/418,786, dated Mar. 28, 2022, 14 pages.
Notice of Allowance received for Australian Patent Application No. 2020239748, dated Mar. 7, 2022, 3 pages.
Notice of Allowance received for U.S. Appl. No. 17/197,628, dated Mar. 23, 2022, 35 pages.
Supplemental Notice of Allowance received for U.S. Appl. No. 17/030,318, dated Mar. 16, 2022, 2 pages.
Corrected Notice of Allowance received for U.S. Appl. No. 16/888,629, dated Jan. 21, 2022, 2 pages.
Corrected Notice of Allowance received for U.S. Appl. No. 17/030,318, dated Jan. 24, 2022, 2 pages.
Non-Final Office Action received for U.S. Appl. No. 17/031,874, dated Jan. 24, 2022, 18 pages.
Notice of Acceptance received for Australian Patent Application No. 2020239743, dated Jan. 13, 2022, 3 pages.
Notice of Allowance received for Chinese Patent Application No. 201780034203.4, dated Jan. 17, 2022, 2 pages (1 page of English Translation and 1 page of Official Copy).
Notice of Allowance received for Chinese Patent Application No. 202010606407.4, dated Jan. 24, 2022, 2 pages (1 page of English Translation and 1 page of Official Copy).
Notice of Allowance received for Japanese Patent Application No. 2018-184532, dated Jan. 17, 2022, 4 pages (1 page of English Translation and 3 pages of Official Copy).
Office Action received for Japanese Patent Application No. 2020-160054, dated Jan. 21, 2022, 8 pages (4 pages of English Translation and 4 pages of Official Copy).
Supplemental Notice of Allowance received for U.S. Appl. No. 16/894,309, dated Jan. 25, 2022, 2 pages.
Applicant-Initiated Interview Summary received for U.S. Appl. No. 17/031,854, dated Feb. 25, 2022, 5 pages.
Applicant-Initiated Interview Summary received for U.S. Appl. No. 17/031,859, dated Feb. 25, 2022, 4 pages.
Applicant-Initiated Interview Summary received for U.S. Appl. No. 17/031,874, dated Feb. 25, 2022, 4 pages.
Notice of Allowance received for U.S. Appl. No. 16/894,309, dated Feb. 25, 2022, 9 pages.
Notice of Allowance received for U.S. Appl. No. 16/994,352, dated Mar. 2, 2022, 14 pages.
Notice of Allowance received for U.S. Appl. No. 17/157,728, dated Feb. 24, 2022, 7 pages.
Office Action received for Australian Patent Application No. 2020239748, dated Feb. 11, 2022, 2 pages.
Office Action received for Chinese Patent Application No. 201910858933.7, dated Dec. 30, 2021, 9 pages (4 pages of English Translation and 5 pages of Official Copy).
Office Action received for Chinese Patent Application No. 201911401161.0, dated Jan. 24, 2022, 6 pages (3 pages of English Translation and 3 pages of Official Copy).
Supplemental Notice of Allowance received for U.S. Appl. No. 17/030,318, dated Feb. 22, 2022, 2 pages.
Applicant-Initiated Interview Summary received for U.S. Appl. No. 17/157,728, dated Feb. 3, 2022, 5 pages.
Intention to Grant received for Danish Patent Application No. PA202070615, dated Jan. 27, 2022, 2 pages.
Notice of Acceptance received for Australian Patent Application No. 2020239752, dated Jan. 31, 2022, 3 pages.
Notice of Allowance received for U.S. Appl. No. 17/192,161, dated Feb. 16, 2022, 8 pages.
Office Action received for Australian Patent Application No. 2021201130, dated Jan. 27, 2022, 2 pages.
Office Action received for Danish Patent Application No. PA202070616, dated Jan. 27, 2022, 2 pages.
Office Action received for Japanese Patent Application No. 2020-160053, dated Jan. 31, 2022, 8 pages (4 pages of English Translation and 4 pages of Official Copy).
Applicant-Initiated Interview Summary received for U.S. Appl. No. 17/192,161, dated Dec. 24, 2021, 4 pages.
Decision of Appeal received for European Patent Application No. 15771747.1, dated Dec. 14, 2021, 21 pages.
International Preliminary Report on Patentability received for PCT Patent Application No. PCT/US2020/035199, dated Dec. 16, 2021, 14 pages.
Non-Final Office Action received for U.S. Appl. No. 17/031,859, dated Dec. 24, 2021, 16 pages.
Notice of Allowance received for Chinese Patent Application No. 201380081349.6, dated Dec. 17, 2021, 2 pages (1 page of English Translation and 1 page of Official Copy).
Notice of Allowance received for Korean Patent Application No. 10-2021-7038005, dated Dec. 14, 2021, 4 pages (2 pages of English Translation and 2 pages of Official Copy).
Office Action received for Chinese Patent Application No. 202010606407.4, dated Nov. 18, 2021, 6 pages (3 pages of English Translation and 3 pages of Official Copy).
Office Action received for Chinese Patent Application No. 202110363565.6, dated Nov. 16, 2021, 16 pages (9 pages of English Translation and 7 pages of Official Copy).
Office Action received for Indian Patent Application No. 202014041571, dated Dec. 17, 2021, 5 pages.
Office Action received for Japanese Patent Application No. 2020-160052, dated Dec. 17, 2021, 10 pages (5 pages of English Translation and 5 pages of Official Copy).
Search Report and Opinion received for Danish Patent Application No. PA202170113, dated Nov. 30, 2021, 9 pages.
Summons to Attend Oral Proceedings received for European Patent Application No. 20182116.2, dated Dec. 21, 2021, 7 pages.
Supplemental Notice of Allowance received for U.S. Appl. No. 16/894,309, dated Dec. 24, 2021, 2 pages.
Final Office Action received for U.S. Appl. No. 16/994,352, dated Dec. 6, 2021, 14 pages.
Minutes of the Oral Proceedings received for European Patent Application No. 15771747.1, dated Dec. 1, 2021, 4 pages.
Notice of Allowance received for U.S. Appl. No. 16/418,786, dated Dec. 9, 2021, 9 pages.

(56) References Cited

OTHER PUBLICATIONS

Corrected Notice of Allowance received for U.S. Appl. No. 16/418,786, dated Jan. 5, 2022, 3 pages.
Non-Final Office Action received for U.S. Appl. No. 16/820,383, dated Jan. 10, 2022, 18 pages.
Non-Final Office Action received for U.S. Appl. No. 17/031,854, dated Dec. 27, 2021, 13 pages.
Notice of Allowance received for U.S. Appl. No. 17/030,318, dated Jan. 5, 2022, 8 pages.
Office Action received for Indian Patent Application No. 202014041563, dated Dec. 30, 2021, 6 pages.
Office Action received for Danish Patent Application No. PA 2020 70612, dated Mar. 1, 2022, 2 pages.
Summons to Attend Oral Proceedings received for European Patent Application No. 13811085.3, dated Mar. 3, 2022, 3 pages.
Applicant Initiated Interview Summary received for U.S. Appl. No. 17/381,570, dated Apr. 26, 2022, 5 pages.
Applicant-Initiated Interview Summary received for U.S. Appl. No. 17/031,543, dated Apr. 21, 2022, 2 pages.
Brief Communication Regarding Oral Proceedings received for European Patent Application No. 20182116.2, dated Apr. 13, 2022, 3 pages.
Corrected Notice of Allowance received for U.S. Appl. No. 17/157,728, dated Apr. 14, 2022, 6 pages.
Corrected Notice of Allowance received for U.S. Appl. No. 17/192,161, dated Apr. 22, 2022, 2 pages.
Corrected Notice of Allowance received for U.S. Appl. No. 17/197,628, dated Apr. 27, 2022, 3 pages.
Notice of Acceptance received for Australian Patent Application No. 2021203636, dated Apr. 14, 2022, 3 pages.
Office Action received for Chinese Patent Application No. 202110783860.7, dated Mar. 10, 2022, 15 pages (5 pages of English Translation and 10 pages of Official Copy).
Supplemental Notice of Allowance received for U.S. Appl. No. 17/030,321, dated Apr. 15, 2022, 2 pages.
Applicant-Initiated Interview Summary received for U.S. Appl. No. 16/418,786, dated May 9, 2022, 2 pages.
Applicant-Initiated Interview Summary received for U.S. Appl. No. 16/820,383, dated May 10, 2022, 2 pages.
Applicant-Initiated Interview Summary received for U.S. Appl. No. 17/516,537, dated Jul. 5, 2022, 4 pages.
Corrected Notice of Allowance received for U.S. Appl. No. 16/418,786, dated Jun. 23, 2022, 2 pages.
Corrected Notice of Allowance received for U.S. Appl. No. 17/031,543, dated Jun. 8, 2022, 3 pages.
Final Office Action received for U.S. Appl. No. 16/820,383, dated Jun. 22, 2022, 21 pages.
Final Office Action received for U.S. Appl. No. 17/031,854, dated Jun. 10, 2022, 15 pages.
Final Office Action received for U.S. Appl. No. 17/031,859, dated Jun. 10, 2022, 13 pages.
Final Office Action received for U.S. Appl. No. 17/031,874, dated Jun. 2, 2022, 19 pages.
Garmin Edge 520, Owner's Manual, online available at: https://www8.garmin.com/manuals/webhelp/edge520/EN-US/Edge_520_OM_EN-US.pdf, 2015, 24 pages.
Intention to Grant received for European Patent Application No. 20182116.2, dated Jun. 2, 2022, 8 pages.
Minutes of the Oral Proceedings received for European Patent Application No. 20182116.2, dated May 24, 2022, 7 pages.
Non-Final Office Action received for U.S. Appl. No. 17/030,318, dated Jun. 14, 2022, 9 pages.
Non-Final Office Action received for U.S. Appl. No. 17/030,337, dated Jun. 14, 2022, 13 pages.
Non-Final Office Action received for U.S. Appl. No. 17/030,340, dated Jun. 14, 2022, 15 pages.
Non-Final Office Action received for U.S. Appl. No. 17/516,537, dated May 5, 2022, 8 pages.
Notice of Allowance received for Japanese Patent Application No. 2020-160052, dated Jun. 3, 2022, 4 pages (1 page of English Translation and 3 pages of Official Copy).
Notice of Allowance received for Korean Patent Application No. 10-2022-7008569, dated May 19, 2022, 5 pages (2 pages of English Translation and 3 pages of Official Copy).
Notice of Allowance received for Korean Patent Application No. 10-2022-7017918, dated Jun. 13, 2022, 6 pages (2 pages of English Translation and 4 pages of Official Copy).
Notice of Allowance received for U.S. Appl. No. 16/418,786, dated Jun. 14, 2022, 9 pages.
Notice of Allowance received for U.S. Appl. No. 16/994,352, dated Jun. 3, 2022, 9 pages.
Notice of Allowance received for U.S. Appl. No. 17/031,543, dated May 11, 2022, 6 pages.
Notice of Allowance received for U.S. Appl. No. 17/192,161, dated May 27, 2022, 8 pages.
Notice of Allowance received for U.S. Appl. No. 17/197,628, dated Jun. 24, 2022, 8 pages.
Office Action received for Australian Patent Application No. 2021204422, dated May 31, 2022, 2 pages.
Office Action received for Chinese Patent Application No. 202110363565.6, dated May 7, 2022, 12 pages (7 pages of English Translation and 5 pages of Official Copy).
Office Action received for Danish Patent Application No. PA202070612, dated May 10, 2022, 2 pages.
Office Action received for Danish Patent Application No. PA202070613, dated May 10, 2022, 2 pages.
Office Action received for Danish Patent Application No. PA202070614, dated Apr. 28, 2022, 4 pages.
Office Action received for Danish Patent Application No. PA202070616, dated May 5, 2022, 3 pages.
Office Action received for Danish Patent Application No. PA202070815, dated Jun. 14, 2022, 3 pages.
Office Action received for Danish Patent Application No. PA202170113, dated May 3, 2022, 2 pages.
Office Action received for Korean Patent Application No. 10-2020-0123815, dated May 31, 2022, 10 pages (5 pages of English Translation and 5 pages of Official Copy).
Summons to Attend Oral Proceedings received for European Patent Application No. 20203526.7, dated Jun. 23, 2022, 9 pages.
Summons to Attend Oral Proceedings received for European Patent Application No. 20721342.2, dated May 20, 2022, 11 pages.
Supplemental Notice of Allowance received for U.S. Appl. No. 16/994,352, dated Jun. 20, 2022, 2 pages.
Supplemental Notice of Allowance received for U.S. Appl. No. 17/030,321, dated Jun. 10, 2022, 2 pages.
Supplemental Notice of Allowance received for U.S. Appl. No. 17/030,321, dated May 27, 2022, 2 pages.
Supplemental Notice of Allowance received for U.S. Appl. No. 17/192,161, dated Jun. 13, 2022, 2 pages.
Supplemental Notice of Allowance received for U.S. Appl. No. 17/192,161, dated May 13, 2022, 2 pages.

* cited by examiner

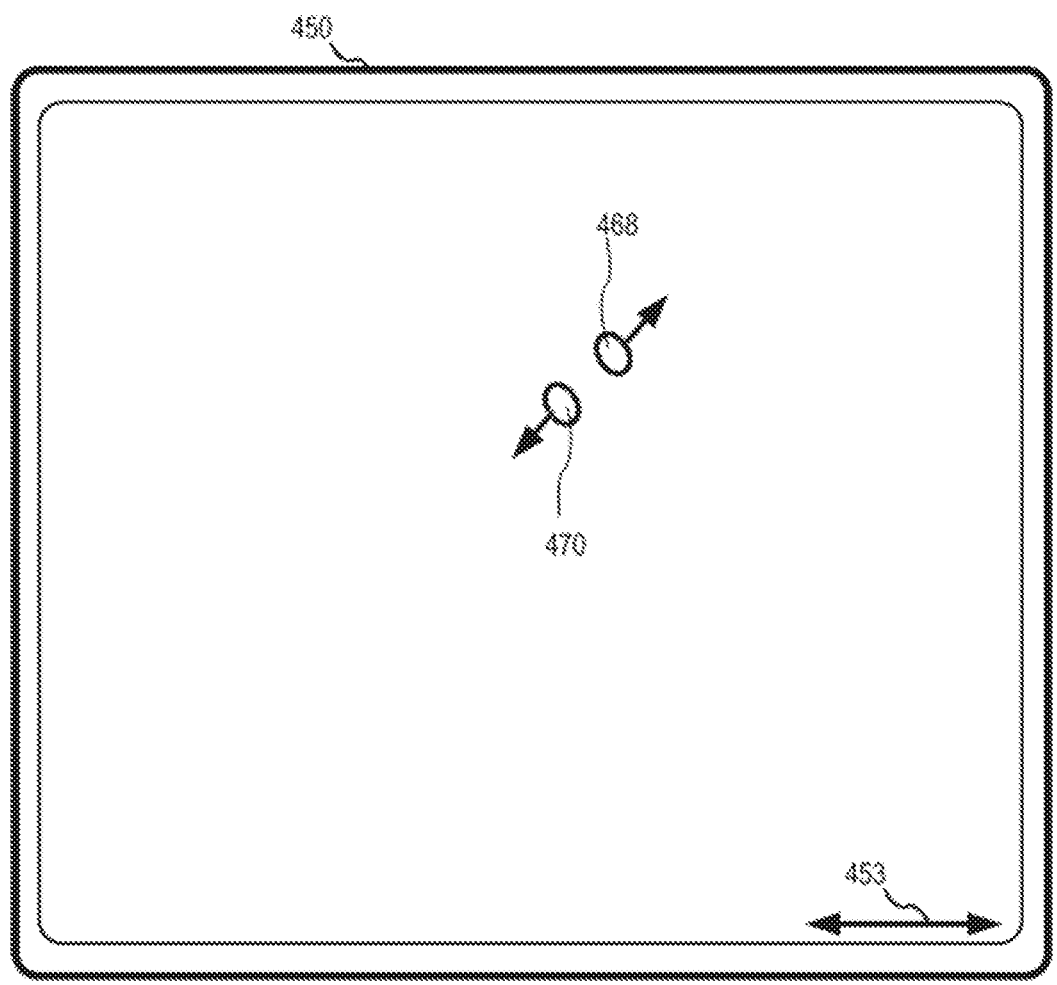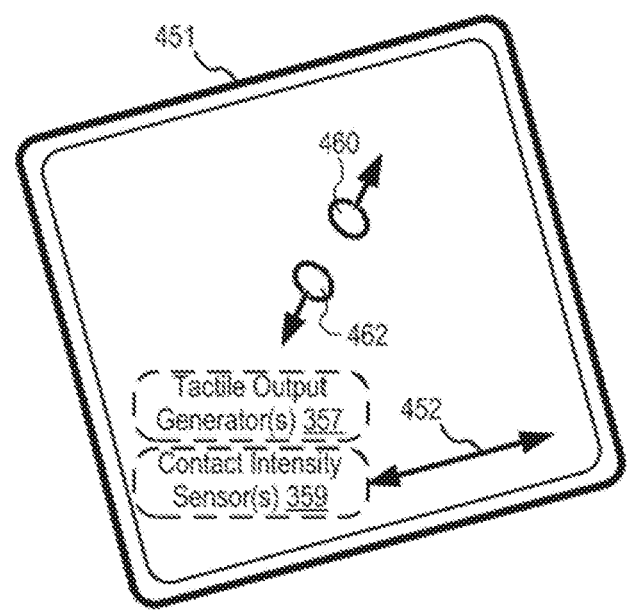
FIG. 4B

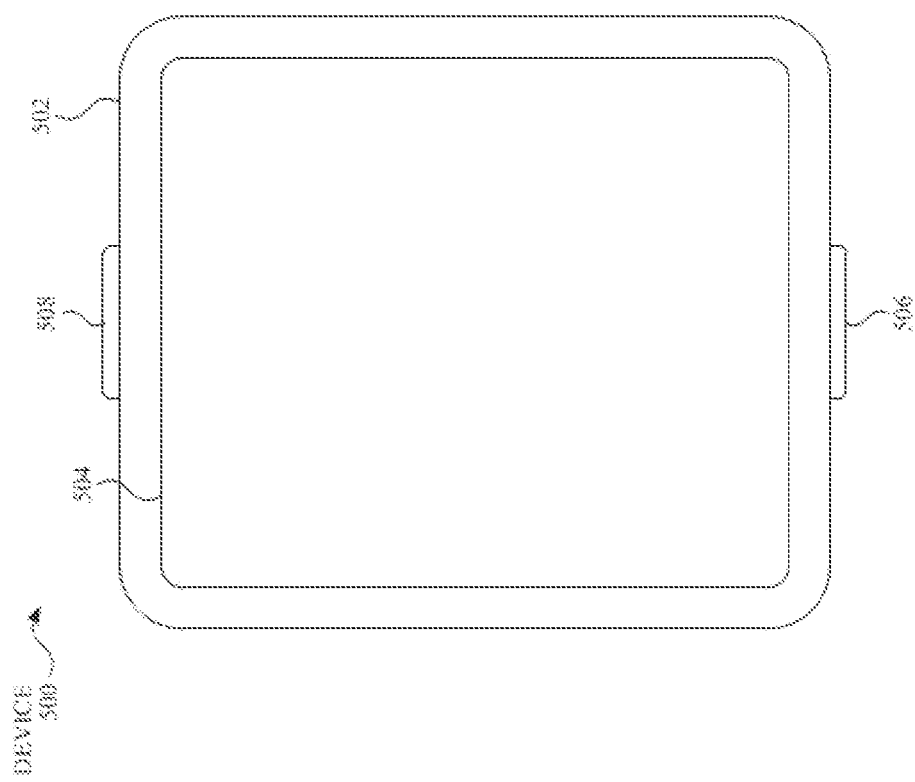

WORKOUT MONITOR INTERFACE

CROSS-REFERENCE TO RELATED APPLICATIONS

This application is a continuation of U.S. patent application Ser. No. 15/600,243, entitled "WORKOUT MONITOR INTERFACE," filed on May 19, 2017, which claims priority to U.S. Provisional Patent Application Ser. No. 62/398,440, entitled "WORKOUT MONITOR INTERFACE," filed on Sep. 22, 2016. The contents of each of which are hereby incorporated by reference in their entirety.

FIELD

The following disclosure relates generally to a computer user interfaces and, more specifically, to techniques and devices for presenting workout monitor interfaces.

BACKGROUND

Whether an individual is exercises for health or competition, the effectiveness of exercise can be improved with real-time feedback of performance and physiological attributes associated with the exercise. For example, data about an individual's heartrate can help the individual determine whether they are in the target heartrate zone for a desired level of activity or whether the individual is over or under exerting themselves. Additionally, performance during exercise can help motivate and track and individual's progress, which aids in reaching goals or even just maintaining a healthy level of exercise.

SUMMARY

Some techniques for presenting workout monitor interfaces using electronic devices, however, are generally cumbersome and inefficient. For example, some existing techniques use a complex and time-consuming user interface, which may include multiple key presses, keystrokes, or other user inputs. Existing techniques require more time than necessary, wasting user time and device energy. This latter consideration is particularly important in battery-operated devices.

Accordingly, the present technique provides electronic devices with faster, more efficient methods and interfaces for workout monitoring. Such methods and interfaces optionally complement or replace other methods for workout monitoring. Such methods and interfaces reduce the cognitive burden on a user and produce a more efficient human-machine interface. For battery-operated computing devices, such methods and interfaces conserve power and increase the time between battery charges.

The present disclosure relates to systems and processes for monitoring a workout and for generating improved interfaces for the same. One example user interface detects when a workout of a particular type is started and begins generating activity data related to workout metrics associated with the type of workout selected. Using determined current values for the workout metrics, the example user interface displays a pro-view ("professional" view) display that includes indicators for the workout metrics associated with the selected workout type. The pro-view display also includes a focus indicator that highlights a selected indicator representative of a focused workout metric. The focus indicator is movable among the indicators representative of the workout metrics based on user input. Upon detection of a gesture, the example user interface transitions to a simple-view display that includes an indicator representative of the focused workout metric. The simple-view display includes indicators for less than all of the workout metrics associated with the selected workout type. The example user interface receives input to change the focused workout metric in the simple-view display. The example user interface also receives a gesture to transition the simple-view display back to the pro-view display.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for workout monitoring, thereby increasing the effectiveness, efficiency, and user satisfaction with such devices. Such methods and interfaces may complement or replace other methods for monitoring workouts.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIGS. 4A and 4B illustrate an exemplary user interface for a menu of applications on a portable multifunction device in accordance with some examples.

FIG. 5A illustrates a portable multifunction device having a touch-sensitive display in accordance with some examples.

DESCRIPTION OF EMBODIMENTS

The following description sets forth exemplary methods, parameters and the like. It should be recognized, however, that such description is not intended as a limitation on the scope of the present disclosure but is instead provided as a description of exemplary embodiments.

There is a need for electronic devices that provide efficient methods and interfaces for workout monitoring. Such techniques can reduce the cognitive burden on a user who accesses workout information, thereby enhancing productivity. Further, such techniques can reduce processor and battery power otherwise wasted on redundant user inputs.

Figure 6:
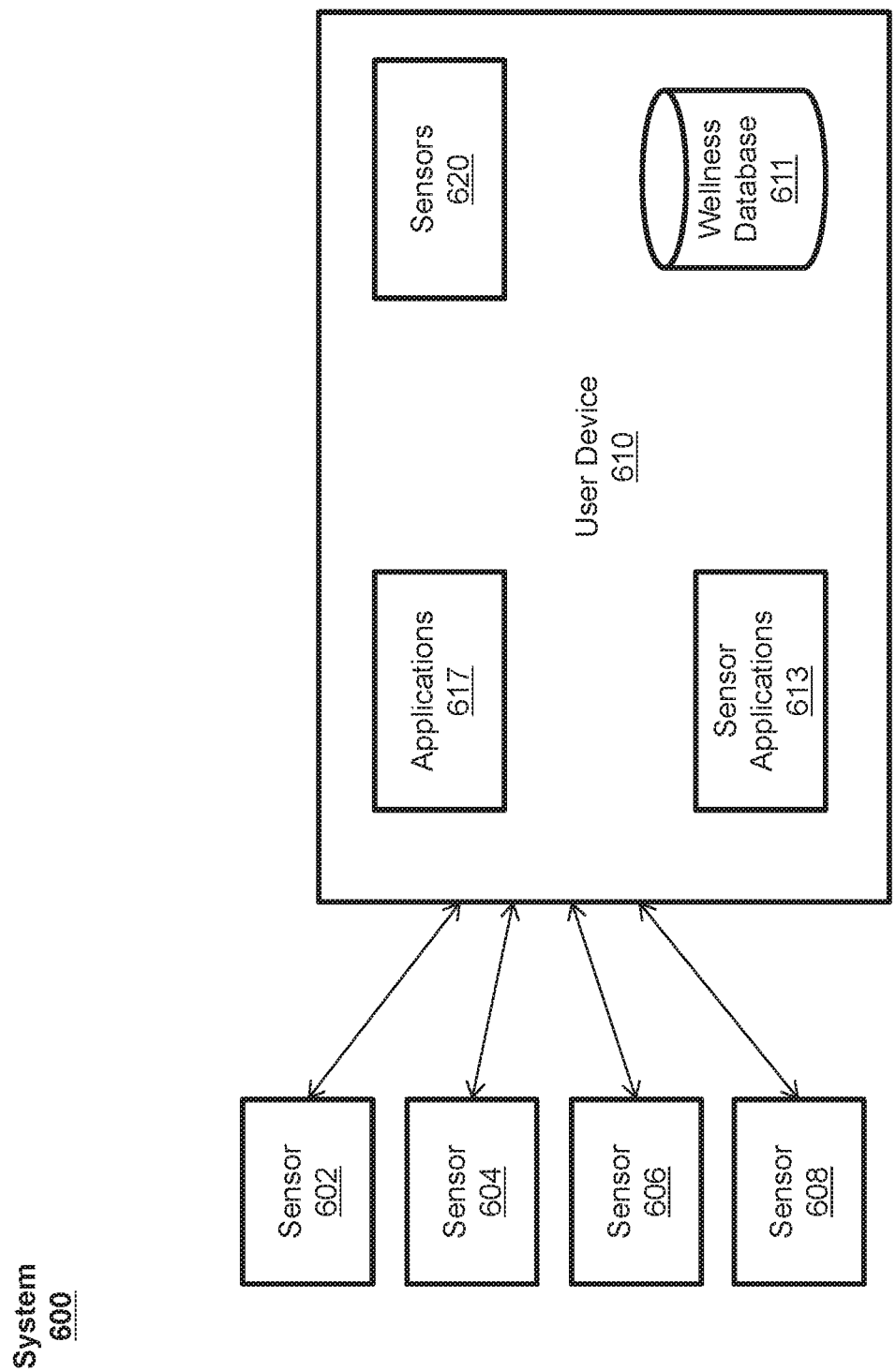
FIG. 6 illustrates a block diagram of an exemplary system for aggregating wellness data according to various examples.
Figure 7:
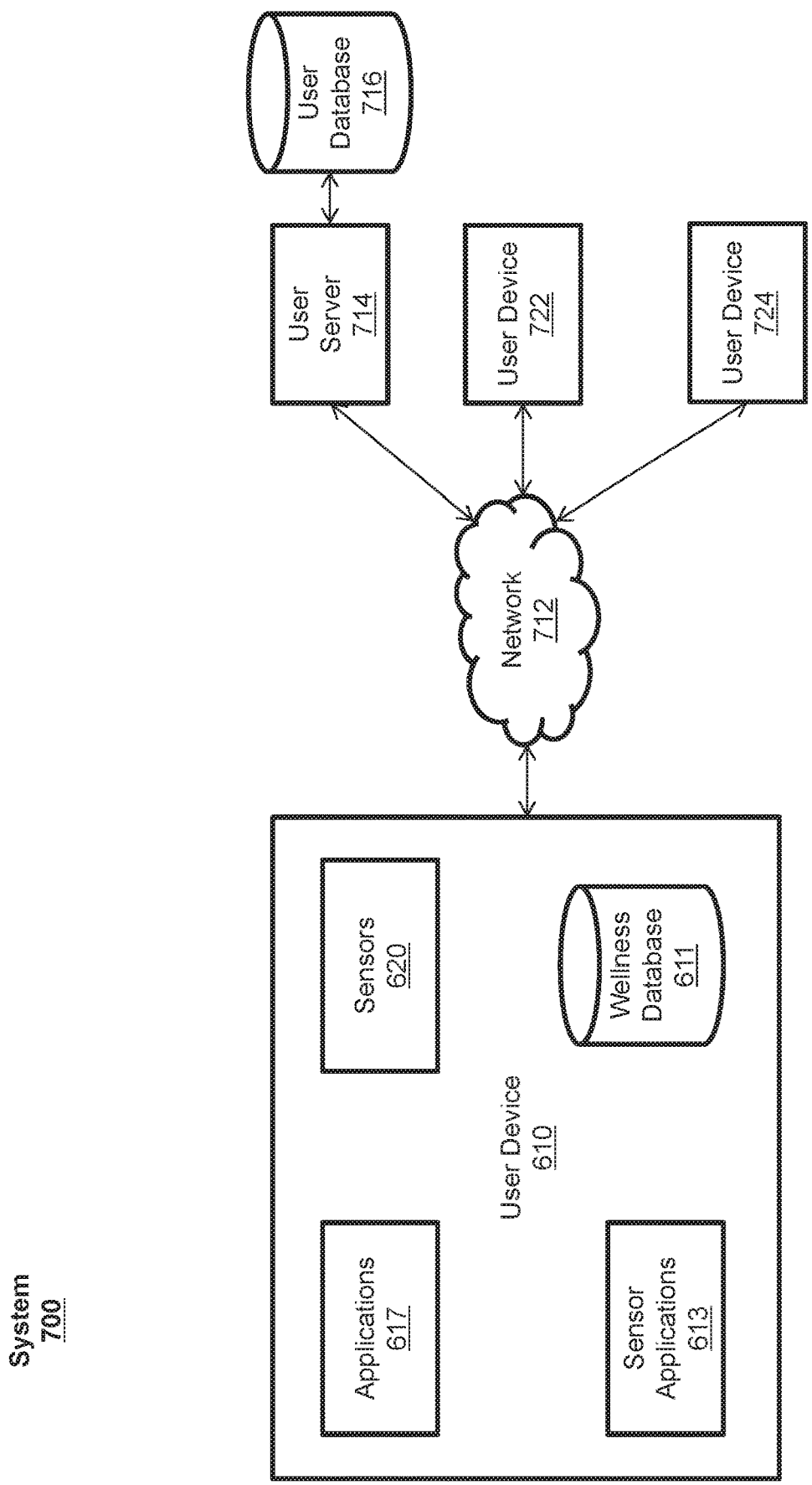
FIG. 7 illustrates a block diagram of another exemplary system for aggregating wellness data according to various examples.
Figure 24:
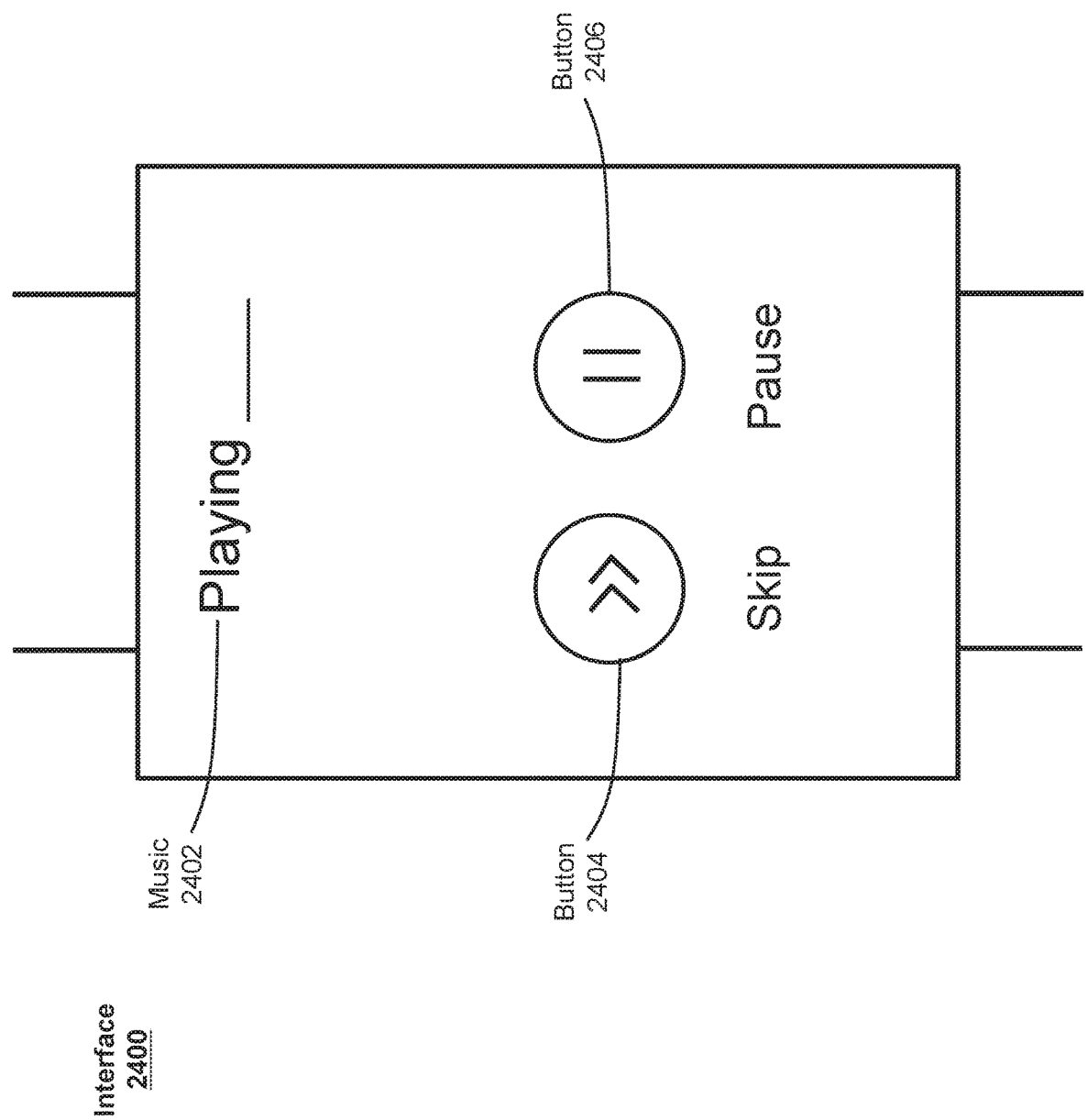
FIG. 24 illustrates exemplary music controls according to various examples.
Figure 25:
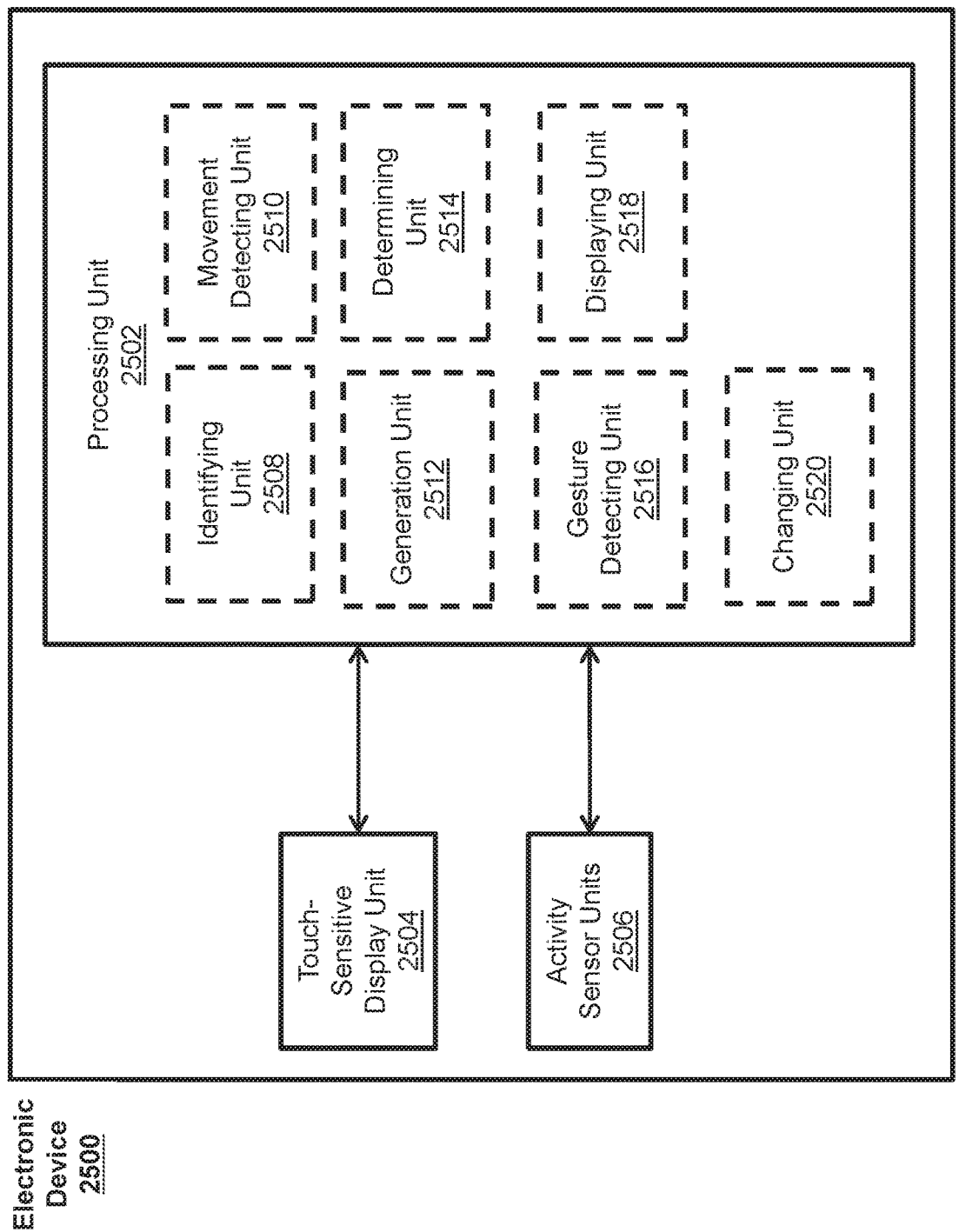
FIG. 25 illustrates functional block diagrams of electronic devices according to various examples.

FIGS. 1A-1B, 2, 3, and 5A-B illustrate exemplary devices for monitoring a user's workout. FIGS. 6 and 7 illustrate exemplary systems for monitoring a user's workout. FIGS. 8, 13-24 illustrate exemplary user interfaces associated with monitoring a user's workout. FIG. 9 is a flow diagram illustrating methods of monitoring a user's workout in accordance with some embodiments. The user interfaces in FIGS. 8, 13-24 are used to illustrate the processes described below, including the process in FIG. 9. FIG. 25 shows an exemplary functional block diagram of an electronic device 2500 configured in accordance with the principles of the various described embodiments.

Exemplary Devices

Although the following description uses terms first, second, etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

Below, FIGS. 1A-1B, 2, 3, 4A-4B, and 5A-5B provide a description of exemplary devices for performing the techniques for monitoring a workout. FIGS. 10-24 illustrate exemplary user interfaces for monitoring a workout. FIG. 9 is a flow diagram illustrating methods of managing event notifications in accordance with some embodiments. The user interfaces in FIGS. 10-24 are used to illustrate the processes described below, including the processes in FIG. 9.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
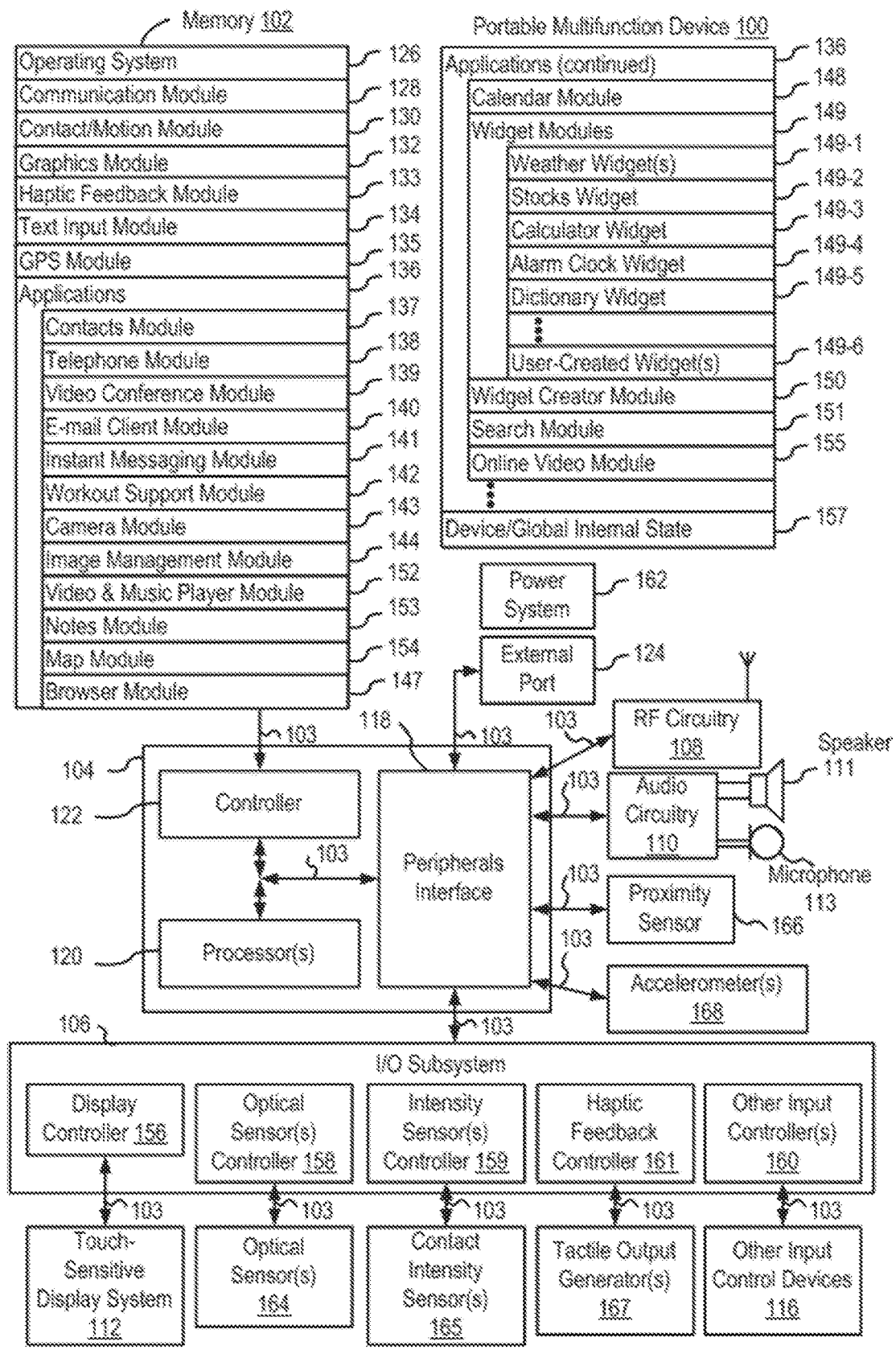
FIG. 1A is a block diagram illustrating a portable multifunction device with a touch-sensitive display in accordance with some examples.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes one or more computer-readable storage mediums. The computer-readable storage mediums are optionally non-transitory. The computer-readable storage mediums are optionally transitory. Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
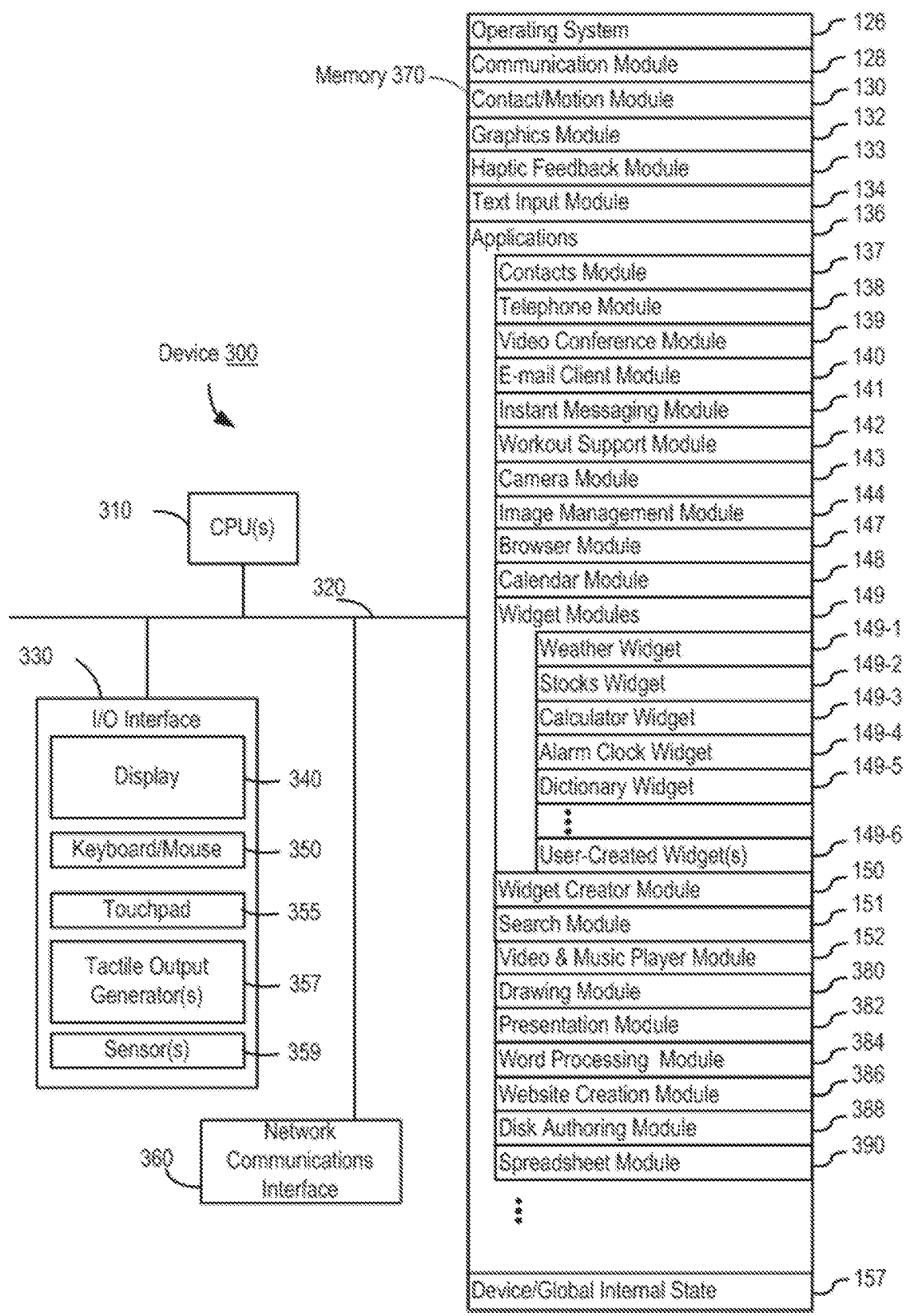
FIG. 3 is a block diagram of an exemplary multifunction device with a display and a touch-sensitive surface in accordance with some examples.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
Contacts module 137 (sometimes called an address book or contact list);
Telephone module 138;
Video conference module 139;
E-mail client module 140;
Instant messaging (IM) module 141;
Workout support module 142;
Camera module 143 for still and/or video images;
Image management module 144;
Video player module;
Music player module;
Browser module 147;
Calendar module 148;
Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
Widget creator module 150 for making user-created widgets 149-6;
Search module 151;
Video and music player module 152, which merges video player module and music player module;
Notes module 153;
Map module 154; and/or
Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
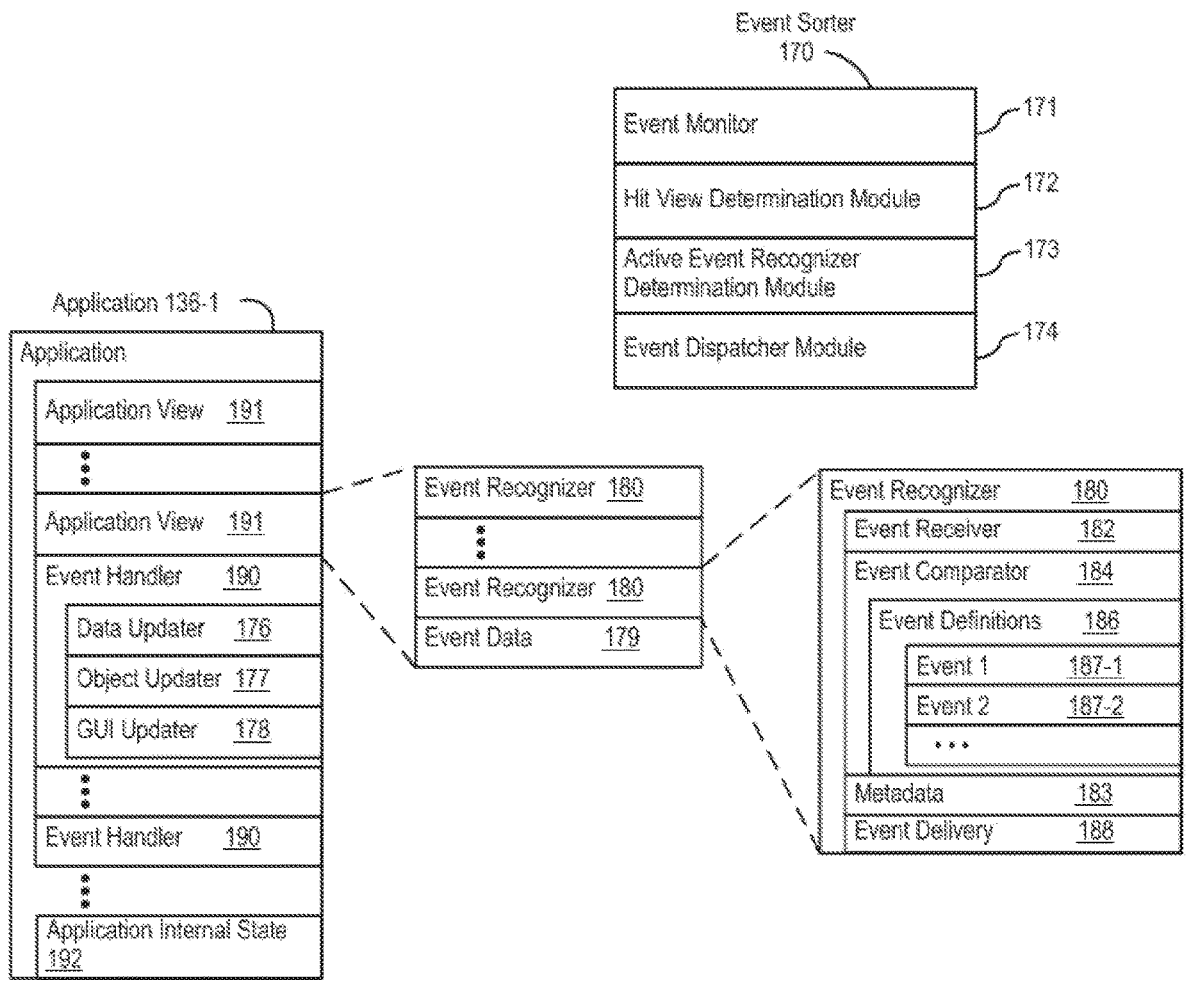
FIG. 1B is a block diagram illustrating exemplary components for event handling in accordance with some examples

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
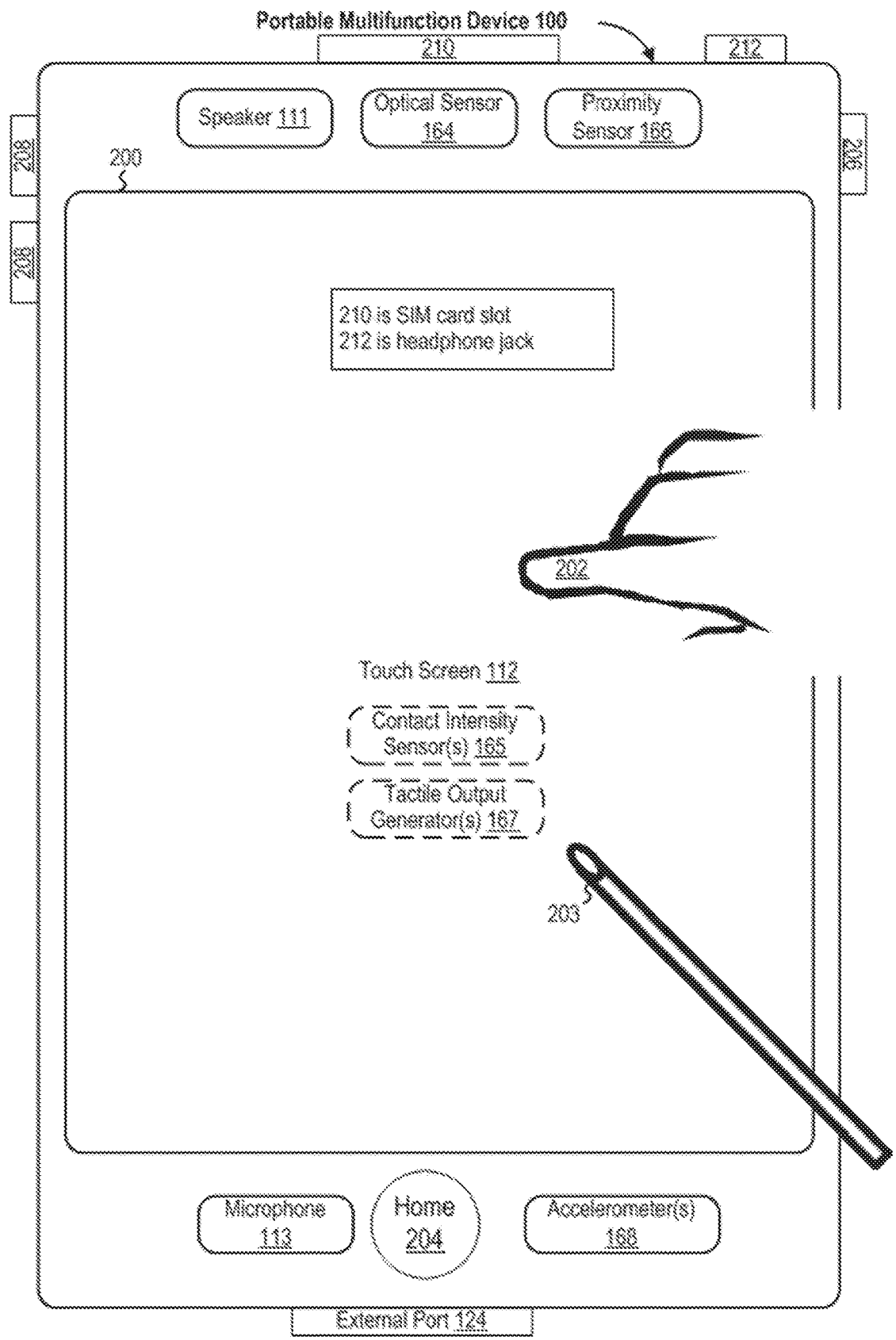
FIG. 2 illustrates a portable multifunction device having a touch-sensitive display in accordance with some examples

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
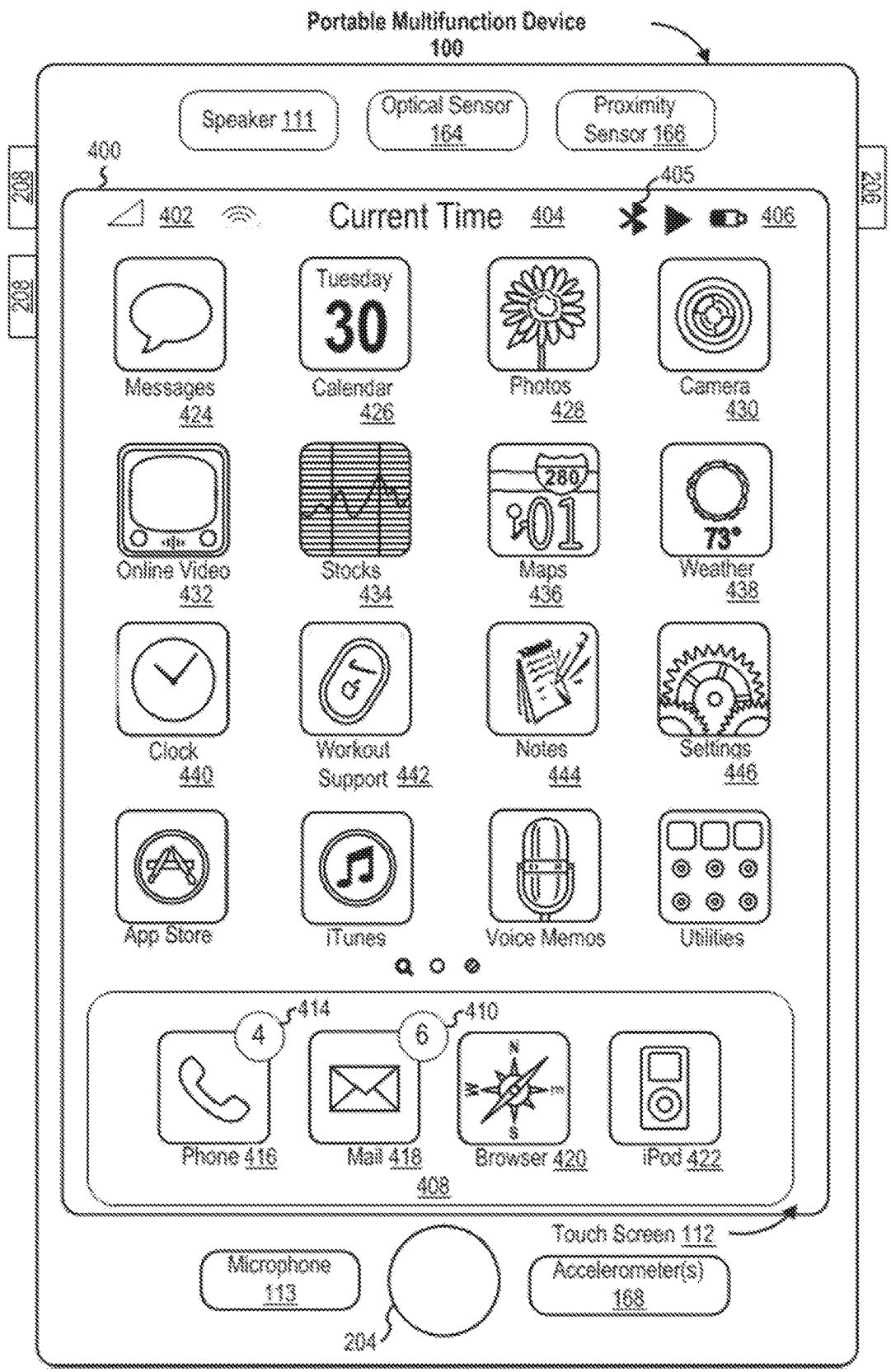

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
    Icon 416 for telephone module 138, labeled "Phone," which optionally includes an indicator 414 of the number of missed calls or voicemail messages;
    Icon 418 for e-mail client module 140, labeled "Mail," which optionally includes an indicator 410 of the number of unread e-mails;
    Icon 420 for browser module 147, labeled "Browser;" and
    Icon 422 for video and music player module 152, also referred to as iPod (trademark of Apple Inc.) module 152, labeled "iPod;" and
Icons for other applications, such as:
    Icon 424 for IM module 141, labeled "Messages;"
    Icon 426 for calendar module 148, labeled "Calendar;"
    Icon 428 for image management module 144, labeled "Photos;"
    Icon 430 for camera module 143, labeled "Camera;"
    Icon 432 for online video module 155, labeled "Online Video;"
    Icon 434 for stocks widget 149-2, labeled "Stocks;"

Icon 436 for map module 154, labeled "Maps;"
Icon 438 for weather widget 149-1, labeled "Weather;"
Icon 440 for alarm clock widget 149-4, labeled "Clock;"
Icon 442 for workout support module 142, labeled "Workout Support;"
Icon 444 for notes module 153, labeled "Notes;" and
Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
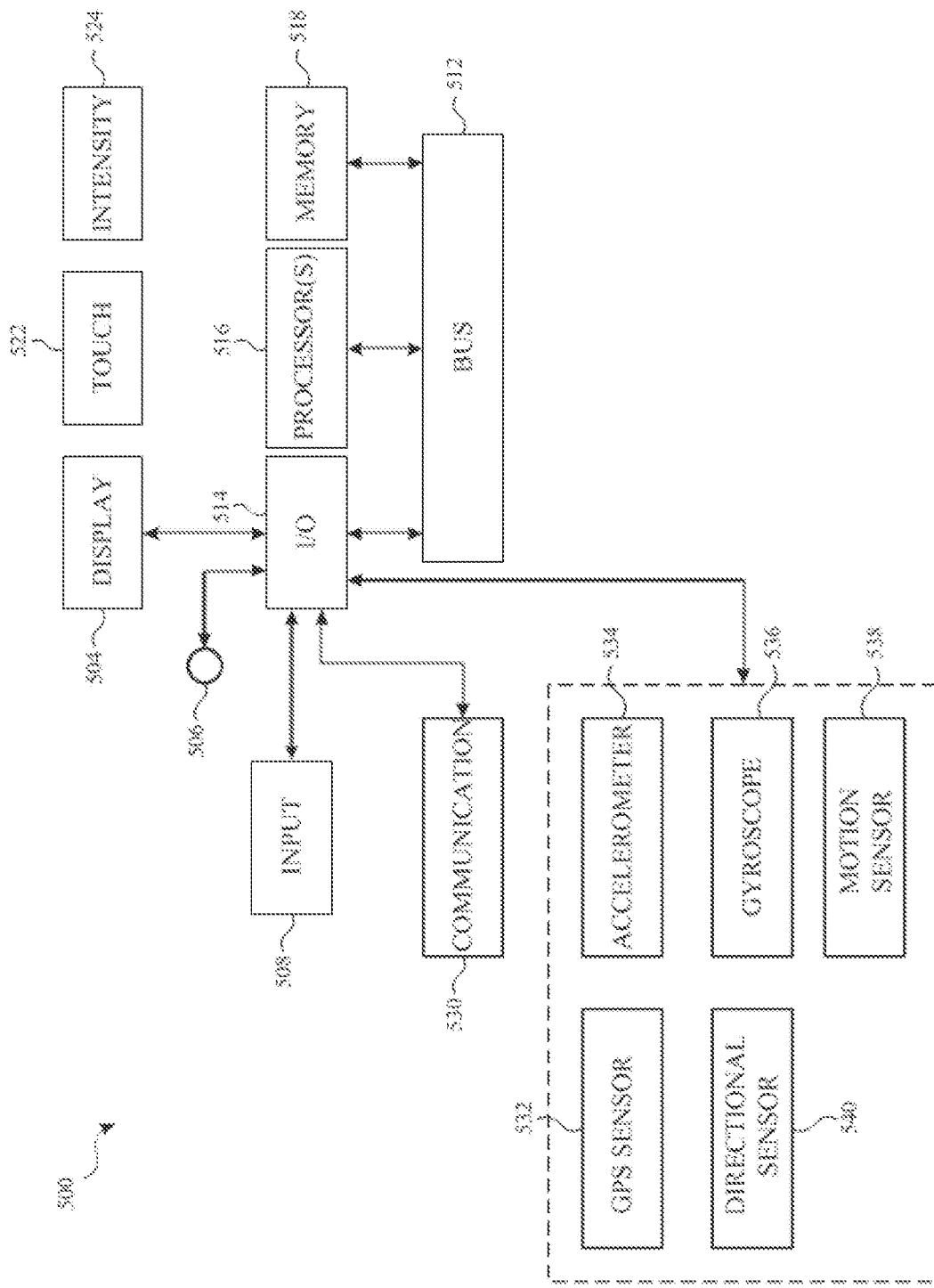
FIG. 5B is a block diagram illustrating a portable multifunction device with a touch-sensitive display in accordance with some examples.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can be a non-transitory computer-readable storage medium, for storing computer-executable instructions, which, when executed by one or more computer processors 516, for example, can cause the computer processors to perform the techniques described below, including process 900 (FIG. 9). The computer-executable instructions can also be stored and/or transported within any non-transitory computer-readable storage medium for use by or in connection with an instruction execution system, apparatus, or device, such as a computer-based system, processor-containing system, or other system that can fetch the instructions from the instruction execution system, apparatus, or device and execute the instructions. For purposes of this document, a "non-transitory computer-readable storage medium" can be any medium that can tangibly contain or store computer-executable instructions for use by or in connection with the instruction execution system, apparatus, or device. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A-B, 3, and 5A-B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UI") and associated processes that are implemented on an electronic device, such as portable multifunction device 100, device 300, or device 500.

Exemplary User Interfaces

Attention is now directed towards embodiments of user interfaces ("UI") and associated processes that are implemented on an electronic device, such as portable multifunction device 100, device 300, or device 500.

FIG. 6 illustrates an example system 600 for aggregating wellness and other types of data. Wellness data can include, but is not limited to, any type of data associated with a person's health, such as their physical activity data, workout data, weight, heart rate, blood pressure, blood glucose level, medication compliance, or the like. System 600 can be used to collect wellness data associated with a user, store the wellness data, present the wellness data to the user in useful ways, and selectively share the user's wellness data with other users or entities based on permissions set by the user. In addition, in some examples, system 600 can further be used to collect non-wellness data along with wellness data, correlate the non-wellness data with the wellness data, and display the non-wellness data with the wellness data.

System 600 can include one or more user devices 610, which can include any type of electronic device, such as a mobile phone, tablet computer, desktop computer, laptop computer, PDA, or the like. In some examples, user device 610 can include a device similar or identical to devices 100, 300, or 500, described above. User device 610 can include an operating system and a wellness database 611 (e.g., memory 102, 370, or 518) for securely storing wellness or non-wellness data along with associated metadata, such as the time the data was recorded, type of data, device used to record the data, user associated with the data, and the like. User device 610 can further include application programming interfaces (APIs) with access controls for storing data in the wellness database 611 and for accessing data stored in the wellness database 611.

User device 610 can be configured to receive wellness or non-wellness data from various sources and can store the received data in the wellness database 611. For example, user device 610 can be configured to receive wellness or non-wellness data from sensors 602, 604, 606, and 608. These sensors can include any type of sensor capable of obtaining wellness data, such as a biometric sensor, activity tracker, or the like. For example, sensors 602, 604, 606, and 608 can include, but are not limited to, a scale, blood pressure cuff, blood glucose monitor, electrocardiogram, step counter, gyroscope, accelerometer, SpO2 sensor, respiration sensor, posture sensor, stress sensor, photoplethysmogram, galvanic skin response sensor, temperature sensor, or the like. Sensors 602, 604, 606, and 608 can also include other types of sensors, such as audio sensors, ambient light sensors, electromagnetic sensors, touch sensors, capacitive sensors, and the like, for obtaining non-wellness data, such as situational data, temporal data, personal data, contact data, and the like data. In some examples, each sensor can be a separate device, while, in other examples, any combination of two or more of the sensors can be included within a single device. For example, the gyroscope, accelerometer, photoplethysmogram, galvanic skin response sensor, and temperature sensor can be included within a wearable electronic device, such as a smart watch, while the scale, blood pressure cuff, blood glucose monitor, SpO2 sensor, respiration sensor, posture sensor, stress sensor, and asthma inhaler can each be separate devices. While specific examples are provided, it should be appreciated that other sensors can be used and other combinations of sensors can be combined into a single device.

Sensors 602, 604, 606, and 608 can be used to measure wellness or non-wellness data continuously, intermittently, periodically, or at any other desired frequency or interval of time. For example, sensors 602, 604, 606, and 608 can be used to obtain a single measurement or multiple measurements over a length of time. Sensors 602, 604, 606, and 608 can be configured to measure wellness or non-wellness data at the same intervals of time, or can be configured to measure wellness or non-wellness data at different intervals of time. These intervals may be set by a user or may be a default setting for each sensor. Additionally, sensors 602, 604, 606, 608 can be used to measure wellness or non-wellness data at any time or location desired by the user. Moreover, sensors 602, 604, 606, and 608 can be used with or without the supervision of a healthcare provider. For example, a user can use sensors 602, 604, 606, and 608 to obtain sensor measurements at home without the supervision of a medical professional.

In some examples, user device 610 can include software sensor applications 613 (e.g., third party applications) associated with each of sensors 602, 604, 606, and 608 for interfacing with the sensors to allow user device 610 to receive the wellness or non-wellness data. In these examples, the applications 613 can use the device's APIs to store the wellness or non-wellness data in the wellness database 611 of user device 610. In some examples, device 610 can be a smart phone, tablet computer, or the like, and the software sensor applications 613 can include software applications downloadable onto device 610. It should be understood that "third party" can correspond to an entity different than the manufacturer of device 610 and/or the entity that created and/or maintains the operating system of device 610. In these instances, third party applications and their corresponding sensors can communicate and function within the operating system of device 610 according to a predefined device protocol associated with device 610.

The applications 613 can similarly use the device's APIs to access data stored in the wellness database 611. In other examples, user device 610 can be configured to share one or more communication formats with sensors 602, 604, 606, and 608 to allow user device 610 to receive and interpret the wellness or non-wellness data from the sensors. The received data can then be stored in the wellness database 611 of user device 610.

User device 610 can further receive wellness or non-wellness data from its own wellness or non-wellness data sensors 620 (e.g., sensors 168, 359, and 520), from a user interacting with user device 610, from another entity, such as a physician, or from other non-sensor sources. For example, using the device's APIs, wellness or non-wellness data can be received from applications 617 (third party or first party applications) on user device 610, such as a clock application, a calendaring application, a gaming application, an application from a healthcare provider, a messaging application, a physical activity application, a workout application, or the like. The wellness or non-wellness data from the applications 617 can originate from sensors 620, a user interacting with the applications, a remote database (e.g., database for a medical website), a healthcare provider institution (e.g., via the institution's application 617), or the like. In these examples, the usage of the application 617 (e.g., how long you play a video game application, when you play the video game, number of times interacting with a stock application, number of times interacting with a social networking application, length of time interacting with a social networking application, etc.), usage of user device 610 (e.g., length of time on the phone or number of text messages sent as determined from a phone payment application, time spent browsing the Internet as determined from the device's browser, etc.), time spent listening to music as determined from a music or streaming radio application, time spent using a remote application for controlling a television, amount of time or money spent on shopping websites, weather data from a weather application (e.g., to determine how weather affects a user's health), type of events occurring in the user's life as determined from a calendar (e.g., meetings, birthdays, holidays, etc.), interactions with certain people as determined from a contact list and/or calendar application and/or a messaging application and/or phone of user device 610, or the like, can be received by user device 610 and stored in the wellness database 611.

In some examples, default or user-selected settings can be provided to restrict the access that at least one application (e.g., at least one of applications 613 and 617) on user device 610 has to the wellness database 611 of user device 610 (for both storage and retrieval purposes) and to the sensor data generated by sensors 620 within user device 610 and/or sensor data generated by sensors 602, 604, 606, and 608. For example, an application for tracking a user's running sessions can be granted access to the data generated by the GPS sensor of user device 610, but can be prevented from accessing the user's blood pressure data stored in the wellness database 611. In some examples, an entity other than the owner of user device 610 can set the authorization settings for various applications on user device 610. For example, the manufacturer of user device 610 and/or the entity that created and/or maintains the operating system of user device 610 can evaluate the applications to determine if they should be given access to the user's wellness data and/or sensor data generated or received by user device 610. In some examples, these settings can be overridden by the user. User device 610 can further include a display for displaying the stored wellness data or non-wellness data.

FIG. 7 illustrates system 700 for sharing user wellness data. System 700 can include user server 714 communicatively coupled to user device 610 via network 712, which can include the Internet, an intranet, or any other wired or wireless public or private network. User device 610 can be configured to securely transmit the aggregated wellness and non-wellness data and associated metadata stored on the device to user server 714 for storage in user database 716. In some examples, the wellness or non-wellness data and associated metadata can be transmitted to user server 714 for storage in user database 716 in response to an explicit request for such a transfer by the user of device 610, while, in other examples, the wellness or non-wellness data can be synced with the data in user database 716 continuously, periodically, intermittently, or at any desired frequency. In yet other examples, the user's wellness or non-wellness data can be stored only on user device 610 and may not be stored in an external database.

In some examples, user server 714 and user database 716 can be configured to securely store a user's wellness or non-wellness data using a public/private key system that only allows the owner of the wellness or non-wellness data to decrypt the data. Additionally, the wellness or non-wellness data stored in user database 716 can be stored anonymously (e.g., without identifying and/or personal information about the user, such as a legal name, username, time and location data, or the like). In this way, other users, hackers, and the owner/operator of user database 716 cannot determine the identity of the user associated with the data stored in database 716. In some examples, a user can access their wellness or non-wellness data stored in user database 716 from a user device that is different than the one used to upload the wellness or non-wellness data to user server 714. In these instances, the user can be required to provide login credentials to access their wellness or non-wellness data. User server 714 can be configured to perform the authorization process to restrict access to the data within user database 716.

System 700 can further include any number of other user devices 722 and 724 coupled to network 712. In some examples, user devices 722 and 724 can be operated by the same user as user device 610. In these instances, the user can access their wellness or non-wellness data stored in user database 716 by providing user server 714 with the appropriate credentials. In some examples, wellness and non-wellness data can be synced between user database 716 and one or more of user device 610, 722, and 724. In other examples, the user of user devices 722 and 724 can be a person that is different than the user of user device 610. In these examples, the users of devices 722 and 724 cannot access the wellness or non-wellness data of the user of user device 610 without the authorization of the user of user device 610. If authorization is given, wellness or non-wellness data can be shared with the users of user devices 722 and 724.

In some examples, any of the above described sources of wellness or non-wellness data can be configured to measure, generate, or receive wellness or non-wellness data continuously, intermittently, periodically, or at any other desired frequency or interval of time. As such, the wellness or non-wellness data can similarly be stored or updated in wellness database 611 or user database 716 continuously, intermittently, periodically, or at any other desired frequency or interval of time. The frequencies and intervals of time used for measuring, generating, receiving, or storing wellness or non-wellness can be the same or they can be different. Additionally, these frequencies and intervals can be default values or they can be set by a user to provide the user with wellness or non-wellness data that has been updated within a desired length of time.

While not shown, it should be appreciated that many other user devices can be coupled to user server 714 through network 712 to collect and store wellness or non-wellness data for other users in a manner similar to that described above.

Workout Monitor

Figure 8:
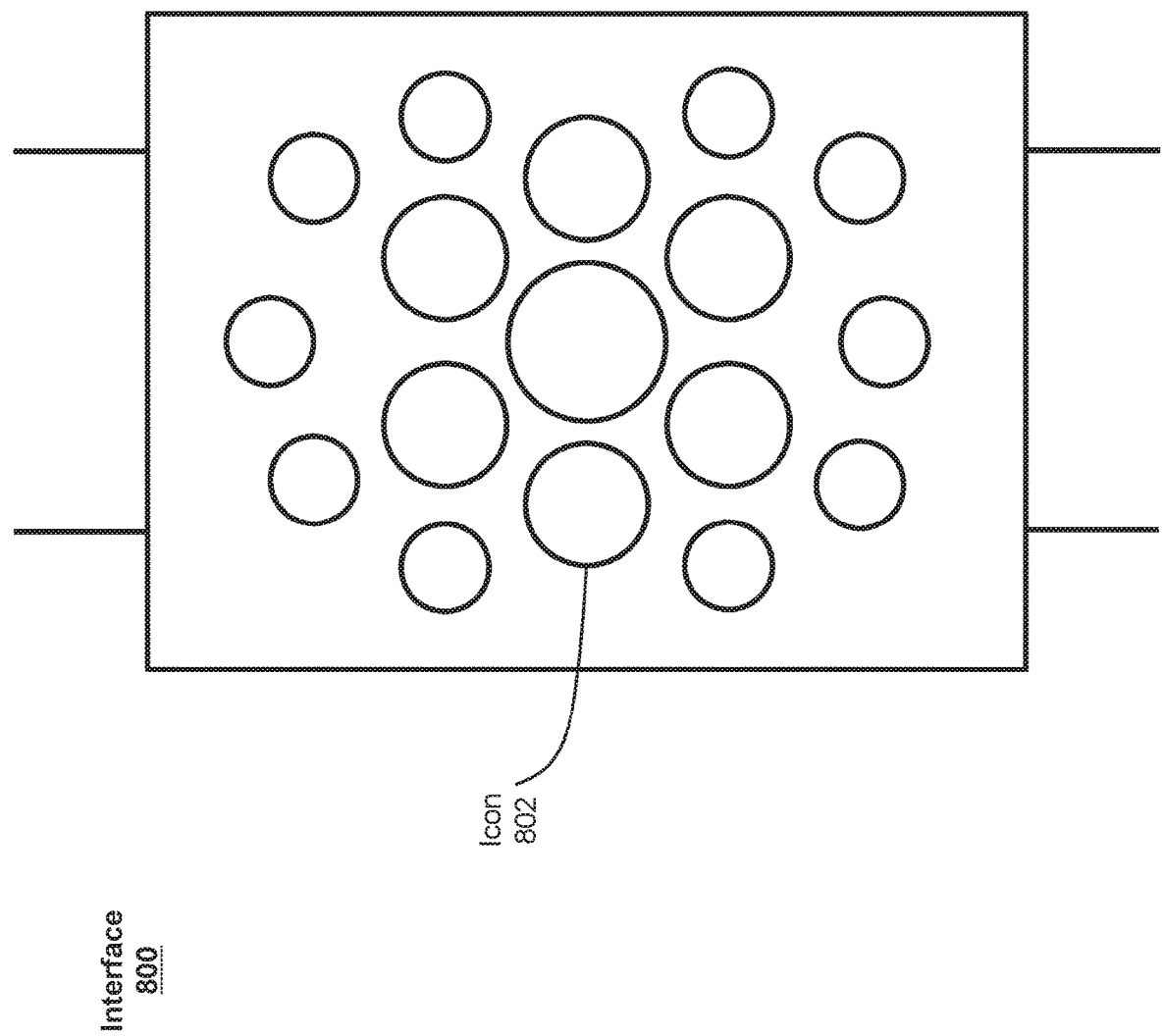
FIG. 8 illustrates an exemplary physical interface for displaying a menu of applications according to various examples.
Figure 9:
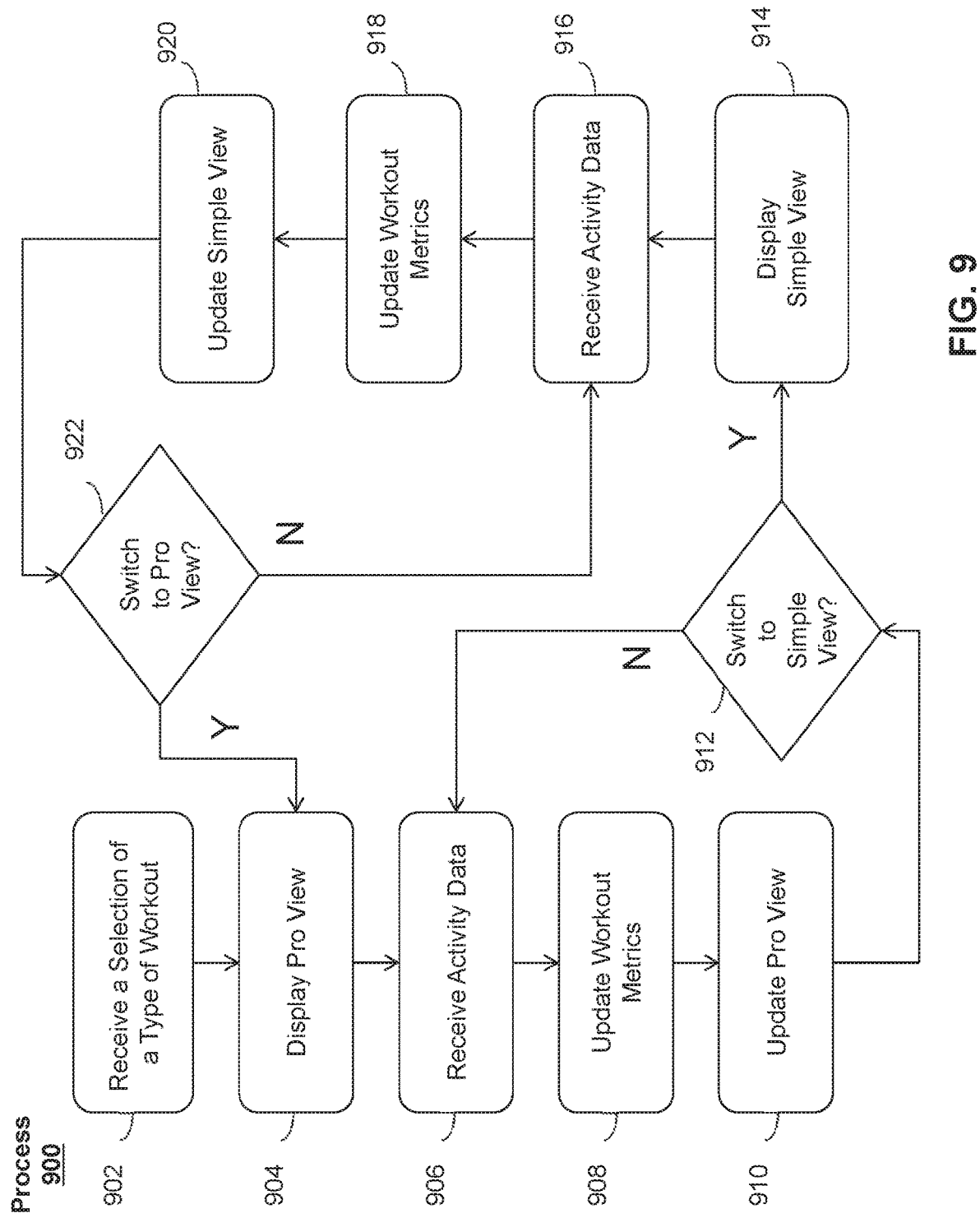
FIG. 9 illustrates a process for generating a workout interface for monitoring a user's workout according to various examples.

FIG. 8 illustrates an exemplary interface 800 for displaying a menu of applications on an electronic device, such as device 100, 300, 500, or 610. As shown, interface 800 includes multiple application icons 802 that, when selected by a user, causes the electronic device to open the associated application. For example, in response to a user selection of an application icon 802 corresponding to a workout application for monitoring a user's workout, the workout application can be opened and process 900, shown in FIG. 9, can be performed. Process 900 can be performed by device 100, 300, 500, or 610 to detect movement associated with the device during a workout, recognizing it as being associated with a physical activity performed by the user using the device, monitoring various metrics of the detected physical activity, determining metrics of the workout based on the monitored metrics of the detected physical activity, and displaying one or more of the metrics of the workout on a display of the device.

At block 902, one or more processors of the device can receive a selection of a type of workout. The selected type of workout can include any type of workout, such as running, walking, cycling, swimming, yoga, dancing, climbing, cross-training, rowing, or the like. In some examples, the one or more processors of the device can cause, on the display of the device, a display of a list of available types of workouts that a user can select. In these examples, the selection of the type of workout can be received by the one or more processors of the device in response to a user indicating a selection of one of the displayed available types of workouts (e.g., via mouse click, touch on a touch sensitive display, or the like).

Figure 10:
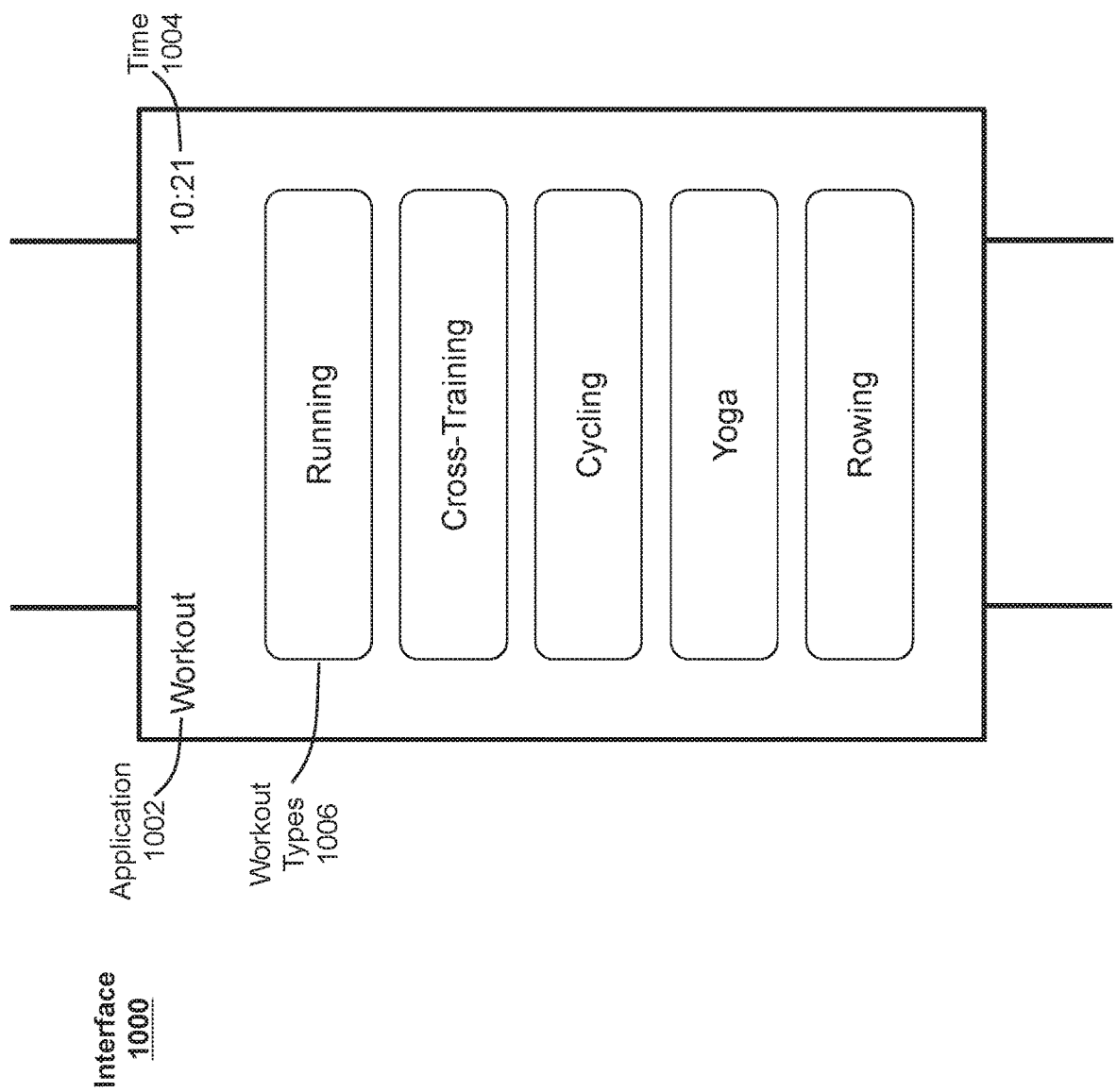
FIGS. 10-12 illustrate exemplary interfaces of a physical activity application according to various examples.

For example, FIG. 10 illustrates an example interface 1000 that can be displayed at block 902 of process 900. As shown, interface 1000 can include an application identifier 1002 indicating that the "Workout" application is being displayed, a time indicator 1004 indicating the current time, and a list of workout types 1006 that includes a list of selectable objects associated with available workouts that can be selected by a user. The types of workouts contained in the list of workout types 1006 can be ordered in any desired manner, such as alphabetically, by frequency of performance, by time since last performed, in a user-selected order, or combinations thereof. For example, the first selectable object can correspond to the workout that was most recently performed by the user ("Running"), and the remaining selectable objects can be ordered based on a frequency that the corresponding workouts have been performed. In some examples, the list of workout types 1006 can include more types of workouts than can be displayed at one time on the display of the device. In these examples, the device can display the other types of workouts in response to a user initiating a scroll operation (e.g., by making a swipe or touch and drag motion on the touch sensitive display). While FIG. 10 shows an example list of workout types 1006, it should be appreciated that the list of workout types 1006 can include any number and types of workouts.

The type of workout selected in block 902 may have multiple workout metrics associated with it. For example, if the workout type "Running" is selected, the workout metrics of elapsed time, distance, pace, and heart rate may be associated with the workout type. In another example, the "Running" workout type may be associated with the elapsed time, distance, pace, heart rate, and calories burned workout metrics. In another example, the cycling workout type may be associated with the elapsed time and distance workout metrics. While a few examples of workout metrics have been given, other workout metrics may also be possible, such as speed, rotations per minute (RPM), and laps.

Additionally, while there may be a default set of workout metrics associated with a given workout type, the set of workout metrics associated with a workout type may be user configurable via a user configuration interface. For example, using a touch-screen or other user input, a user can select workout metrics that are an associated with a given workout metric.

Figure 11:
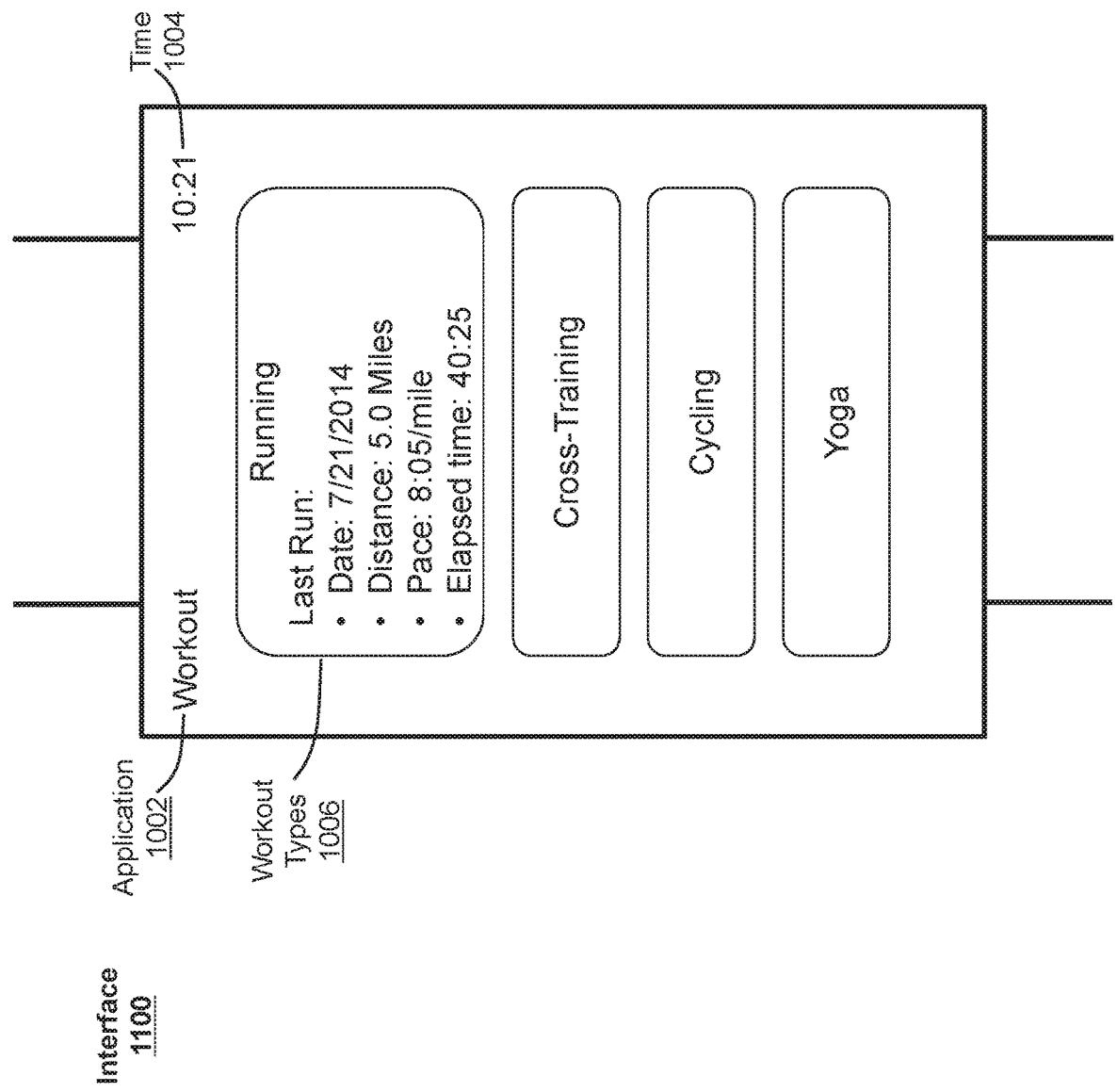

FIG. 11 illustrates another example interface 1100 that can be displayed at block 902 of process 900. Similar to interface 1000, interface 1100 can include an application identifier 1002, a time indicator 1004, and a list of workout types 1006. However, in interface 1100, one selectable object associated with a type of workout in the list of workout types 1006 can be larger than the selectable objects associated with other types of workouts and can include additional information about the workout type. This selectable object can correspond to the workout that was most recently performed by the user. For example, as shown in FIG. 11, the selectable object for the "Running" workout type can be twice as large as the other selectable objects and can include information associated with the most recent workout of that type. In particular, information about the date, distance, pace, and elapsed time of the most recent run is displayed on the selectable object for the "Running" type of workout. The selectable objects below the larger selectable object can be ordered based on a frequency that the corresponding workouts are performed. Alternatively, the objects may be ordered by recency, or a combination of recency and frequency. In some examples, an interface similar to interface 1000 can be displayed the first time that a user is using the workout application on the device, while an interface similar to interface 1100 can be displayed during any subsequent use of the application.

Optionally, in block 902, a later block of process 900, or in a block after block 902 that is not depicted in FIG. 9, a goal for the type of workout selected can be received. The goal can include an identification of a workout metric of the selected workout (e.g., a distance, a duration, a number of Calories burned, a pace, or the like) and a goal value for the workout metric. For example, for a running type of workout, the goal received at block 904 can include a distance workout metric and a value of 10 kilometers. Another example goal can include a duration workout metric and a value of 45 minutes, or a Calorie workout metric and a value of 110 Calories. In some examples, the one or more processors of the device can cause, on the display of the device, a display of an interface that allows the user to select a workout metric of the workout and to enter a desired value for that workout metric.

Figure 12:
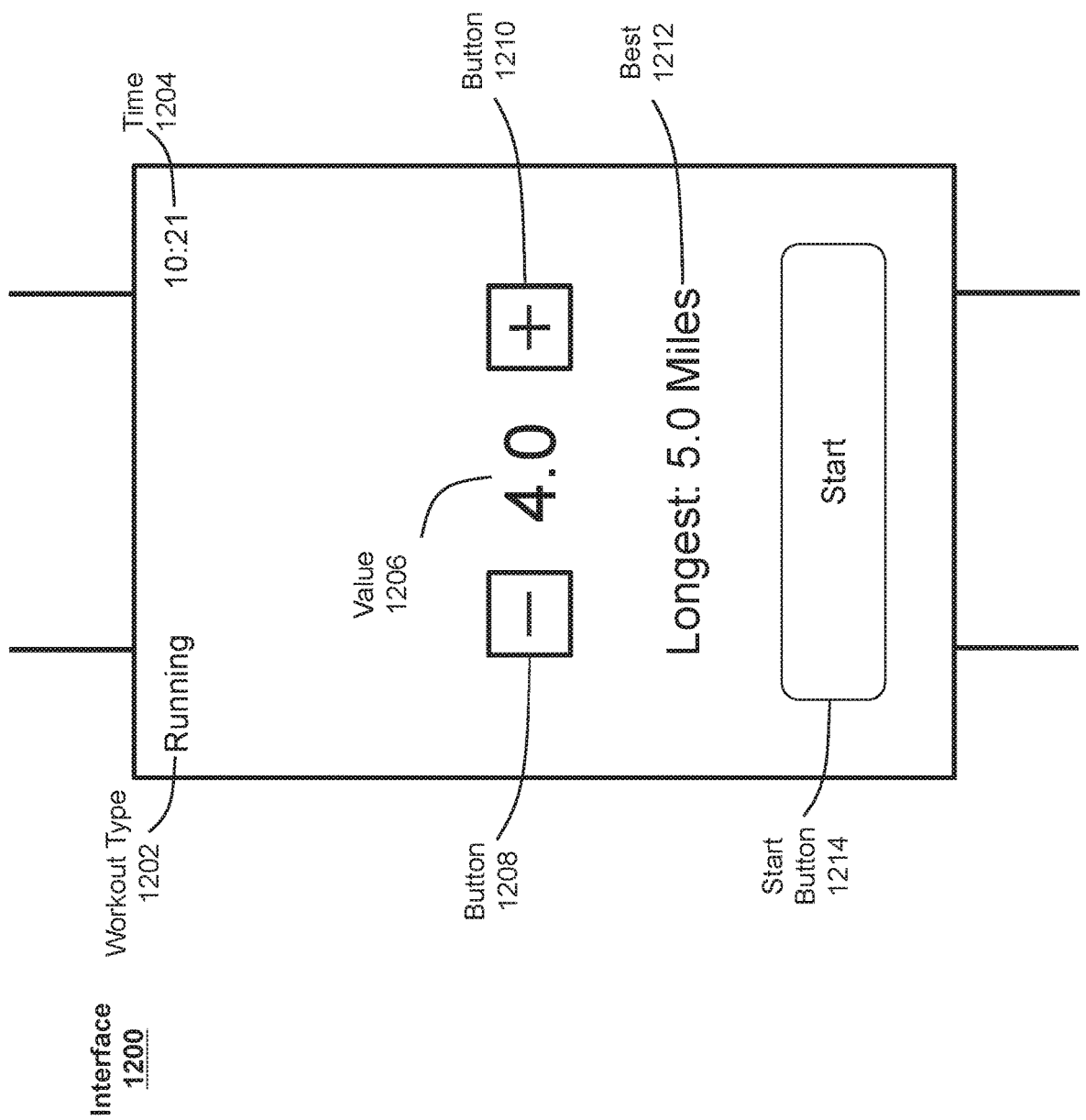

For example, FIG. 12 illustrates an example interface 1200 that can be displayed at block 904 of process 900 in response to receiving a selection of a "running" type of workout at block 902 (e.g., by a user selecting the "Running" option in either interface 1000 or 1100). As shown, interface 1200 can include a workout type identifier 1202 indicating that the "Running" type of workout was selected, a time indicator 1204 indicating the current time, a value 1206 for the workout metric of the workout, buttons 1208 and 1210 for adjusting the value 1206, a best value 1212 of the workout metric of the workout, and a start button 1214 for selecting the goal and beginning the workout. In this example, the distance workout metric of the workout is being selected and the value for that workout metric can be selected by adjusting value 1206 up or down using buttons 1210 or 1208, respectively. In other examples, the value for that attribute can be selected by moving (e.g., rotating) a rotatable input mechanism of the device. The initial value 1206 displayed in interface 1200 can be a default value (e.g., 0), a value used in a previous workout, an average value from two or more previous workouts, or any other desired value. Once the desired value 1206 is displayed, a user can select the start button 1214 to set the workout goal to be a distance goal having the value of value 1206. In some examples, best value 1212 can be selectable and can cause the goal of the workout to be the attribute and value of the displayed best value 1212. For example, in response to a selection of best value 1212 made by a user tapping on the touch-sensitive display at a location corresponding to best value 1212, the goal of the workout can be set to a distance goal of 5.0 miles. In other examples, best value 1212 can represent a value determined based on past performance of the user, the user's contacts, the user's friends, a predefined group of users, or the like. For example, best value 1212 can instead represent the longest distance run by the user over a predetermined length of time (e.g., the last week), an average distance run by the user, an average distance run by the user over a predetermined length of time (e.g., the last week), a longest distance run by the user's contacts/friends/running group, a longest distance run by the user's contacts/friends/running group over a predetermined length of time (e.g., the last week), an average distance run by the user's contacts/friends/running group, an average distance run by the user's contacts/friends/running group over a predetermined length of time (e.g., the last week), or the like. In some examples, the device can allow a user to select a different workout metric of the workout as the goal by displaying a different interface associated with a different workout metric of the workout in response to a request from the user. In some examples, the request can be made by a vertical or horizontal swipe gesture across the touch sensitive display of the device, a button press, a movement of a rotatable input mechanism of the device, a user contact having a characteristic intensity above an intensity threshold on a display of the device, or any other desired form of input.

In other examples, the device can select from other of interfaces similar to interface 1200 that allows for other types of goals to be set. For example, while example interfaces for selecting specific workout metrics for the "Running" type of workout have been provided in FIG. 12, it should be appreciated that interfaces for selecting any workout metric of any type of workout can be provided based on the types of workout metrics associated with the workout type selected at block 902. For example, if the type of workout selected at block 902 was "yoga," an interface for selecting a duration goal or a Calorie goal may be displayed, but an interface for selecting a distance goal may not be displayed.

In some examples, in response to a selection of start button 1214 in interface 1200, the device can optionally display a countdown before beginning the workout selected at block 902 using the selected goal.

Referring back to FIG. 9, at block 904, in response to a request to display workout metric data, a pro-view display of the workout metrics associated with the workout type selected in block 902 is made on the device. The request to display workout metric data may take the form of, for example, detection of activity associated with start button 1214 of FIG. 12. As another example, the request to display workout metric data could also take the form of the selection of workout type in block 902. As another example, the request to display workout metric data could be associated with detecting movement or some other information associated with sensors 620 of user device 610 (FIG. 6).

Figure 13:
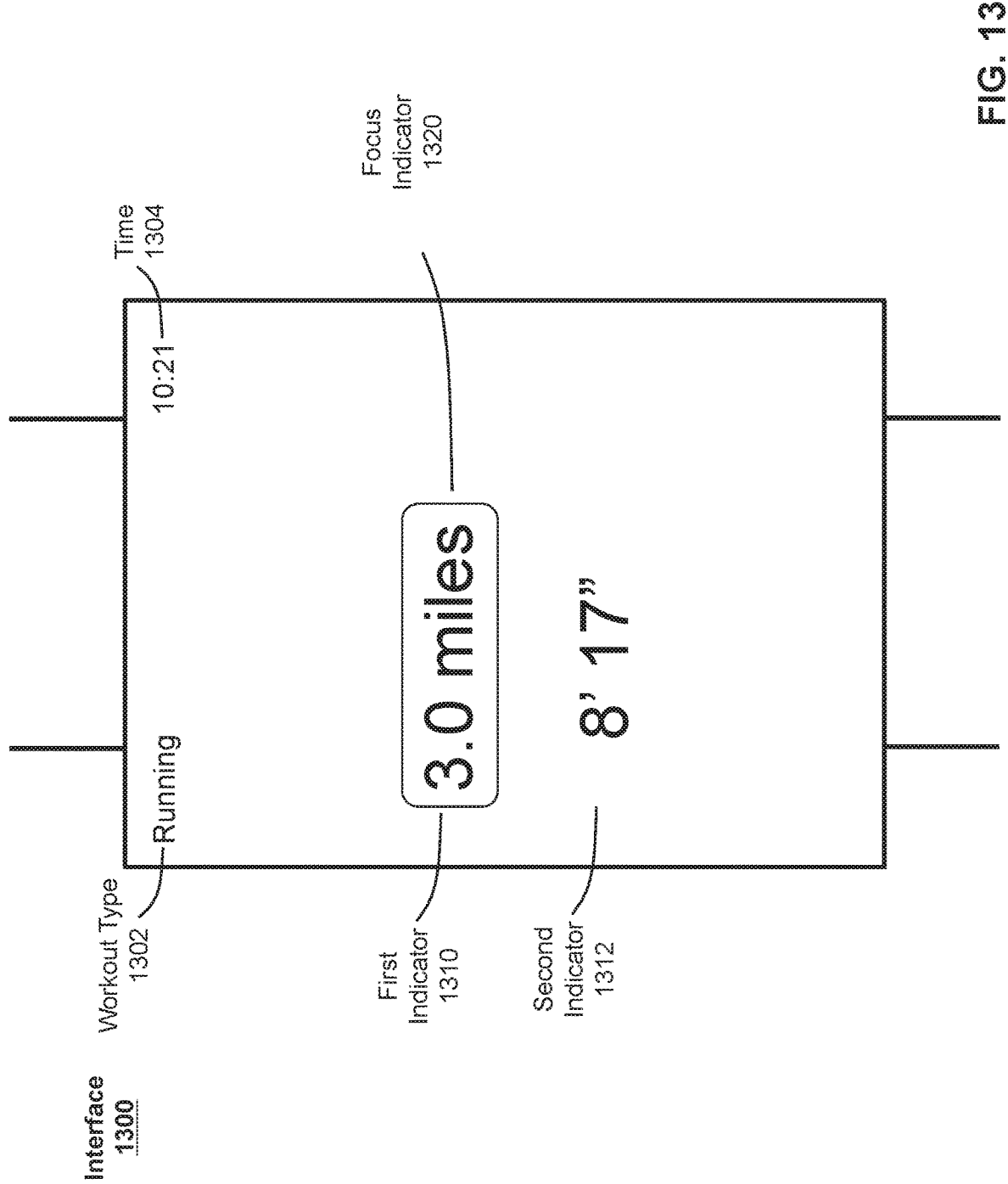
FIGS. 13, 14, 17, 18, and 21 illustrate exemplary interfaces of a pro-view display according to various examples.

The pro-view display includes an indicator representative of each of the plurality of workout metrics associated with the workout type selected in block 902. For example, FIG. 13 depicts interface 1300, which is an example of the pro-view displayed in block 904. FIG. 13 is the pro-view for the workout type "Running" and includes two associated workout metrics. Interface 1300 includes a first indicator 1310 representing a first workout metric, in this case a distance traveled metric, and a second indicator 1312 representing a second workout metric, in this case a pace workout metric. Interface 1300 may also include the selected workout type in the form of workout type 1302 and other information, such as time 1304.

Interface 1300 also includes a focus indicator 1320 that highlights a workout metric indicator that is currently selected as the focused workout metric. In interface 1300, first indicator 1310 represents the focused workout metric. The focus indicator 1320 may be a box or other shape around one of the workout metric indicators, but other methods of highlighting a workout metric indicator may also be used, such as a different coloring, a larger font size, a different background color, or blinking of the indicator. The focus indicator 1320 may be moved to other workout metrics indicators based on, for example, user input. Examples of user input include receiving a gesture on a touch-sensitive display or mechanical user input device, such as a rotatable crown or button. Focus indicator 1320 may aid in a user concentrating on a particular workout metric that is important to the user or for the particular workout type.

Figure 14:
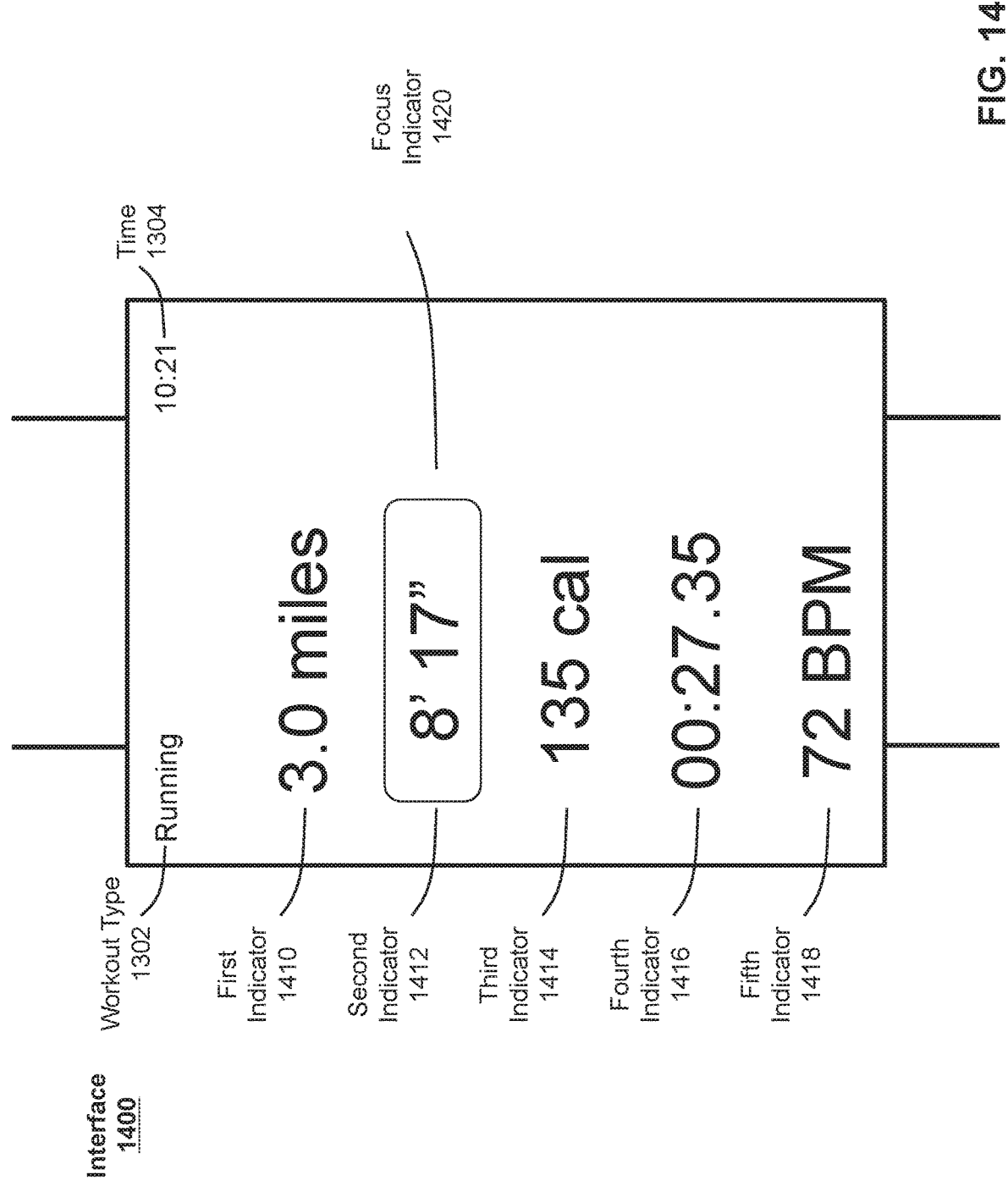

As explained above, the workout metrics associated with a given workout type may be configurable. FIG. 14 depicts interface 14 for the "Running" workout type but with a different set of workout metrics associated with the "Running" workout type as compared to interface 1300 of FIG. 13. Interface 1400 includes first indicator 1410 for the distance workout metric, second indicator 1412 for the pace workout metric, third indicator 1414 for the Calories workout metric, fourth indicator 1416 for the time elapsed workout metric, and fifth indicator 1418 for the heartrate workout metric. In interface 1400, focus indicator 1420 has been moved to represent that second indicator 1412 represents the focused workout metric. While two example interfaces having two and five workout metric indicators have been provided, other numbers of indicators may be included in the pro-view. For example, the pro-view may include exactly four indicators of workout metrics. Additionally, the different indicators for the workout metrics may use different colors to set apart the different indicators and make for a more pleasant viewing experience.

The ordering of the workout metric indicators in pro-view displays may be configurable. For example, the position of first indicator 1410 with respect to second indicator 1412 may be changed. In some cases, the position may be changed by, for example, dragging the first indicator to a new position while in a position configuration user interface.

Also at block 904, before or after displaying the pro-view, the workout may also be initiated. Initiating the workout can include activating one or more activity sensors (e.g., sensors 168, 359, and 520) and recording activity data provided by those one or more activity sensors. In some examples, the activity sensors activated at block 904 can be selected based on the type of workout selected at block 902. For example, a biometric sensor for measuring heart rate, GPS sensor for measuring position, and accelerometer for measuring motion to determine distance traveled can be activated if a running type of workout was selected at block 902. However, if a cycling type of workout was selected at block 902, a biometric sensor for measuring heart rate and a GPS sensor for measuring position may be activated at block 902, but an accelerometer may not be activated. This may be done because an accelerometer may not provide reliable information in determining distance traveled on a bike and can be left inactive to save power. Other combinations of activity sensors can selectively be activated for other types of workouts.

Referring back to FIG. 9, at block 906 one or more processors of the device can receive activity data that is representative of sensed physical activity of a user from an activity sensor. At block 908, the one or more processors can process the received activity data to update values of attributes of the workout stored on the device. For example, a timer can be used to update the duration of the workout based on a difference between a current value of the timer and a value of the timer when the workout was initiated at block 904. Additionally, an accelerometer, motion sensor, gyroscope, biometric sensor, and/or GPS sensor can be used to update a distance traveled during the workout and can additionally or alternatively be used to update a number of Calories burned during the workout (in combination with the user's age, gender, and weight). The timer can be used in combination with the accelerometer, motion sensor, and/or GPS sensor to update a pace of the user during the workout. Other activity sensors can similarly be used to determine and update values of other workout attributes.

At block 910, one or more processors of the device can update the pro-view display (e.g., those shown in FIGS. 13 and 14) to reflect the updated values of the workout metrics determined at block 908. For example, with reference to FIG. 14, the first indicator 1310 can be adjusted to reflect the total distance traveled, second indicator 1312 can be moved to reflect the updated pace value, and third indicator 1314 can be updated to reflect the updated value of Calories burned, fourth indicator 1416 can be updated to reflect the updated value of the time elapsed, and fifth indicator 1418 can be update to reflect the updated value of the heart rate.

Blocks 906, 908, and 910 can continue to be repeated to provide the user with up to date information associated with the workout metrics of the workout type via the pro-view display. In some examples where the workout application is running in the background of the device or while the display of the device is deactivated, block 910 can be omitted and blocks 906 and 908 can repeatedly be performed to monitor the user's workout and update the monitored workout metrics such that an accurate display of the metrics can later be provided to the user when the physical activity application is reopened or the display of the device is activated. In some examples, upon activating the display of the device, the workout interface previously displayed (e.g., one of the interfaces displayed in FIGS. 13 and 14) before deactivating the display can be displayed. This workout interface can be displayed while the device is in a locked state or can be displayed in response to unlocking the device.

In block 912, one or more processors of the device can cause the pro-view display to continue to be displayed. Alternatively, something may trigger a simple-view display to be displayed. For example, a gesture, such as a horizontal swipe, may be detected that causes a transition from the pro-view display to the simple-view display. Other user input could also cause the transition from the pro-view display to the simple-view display.

Figure 15:
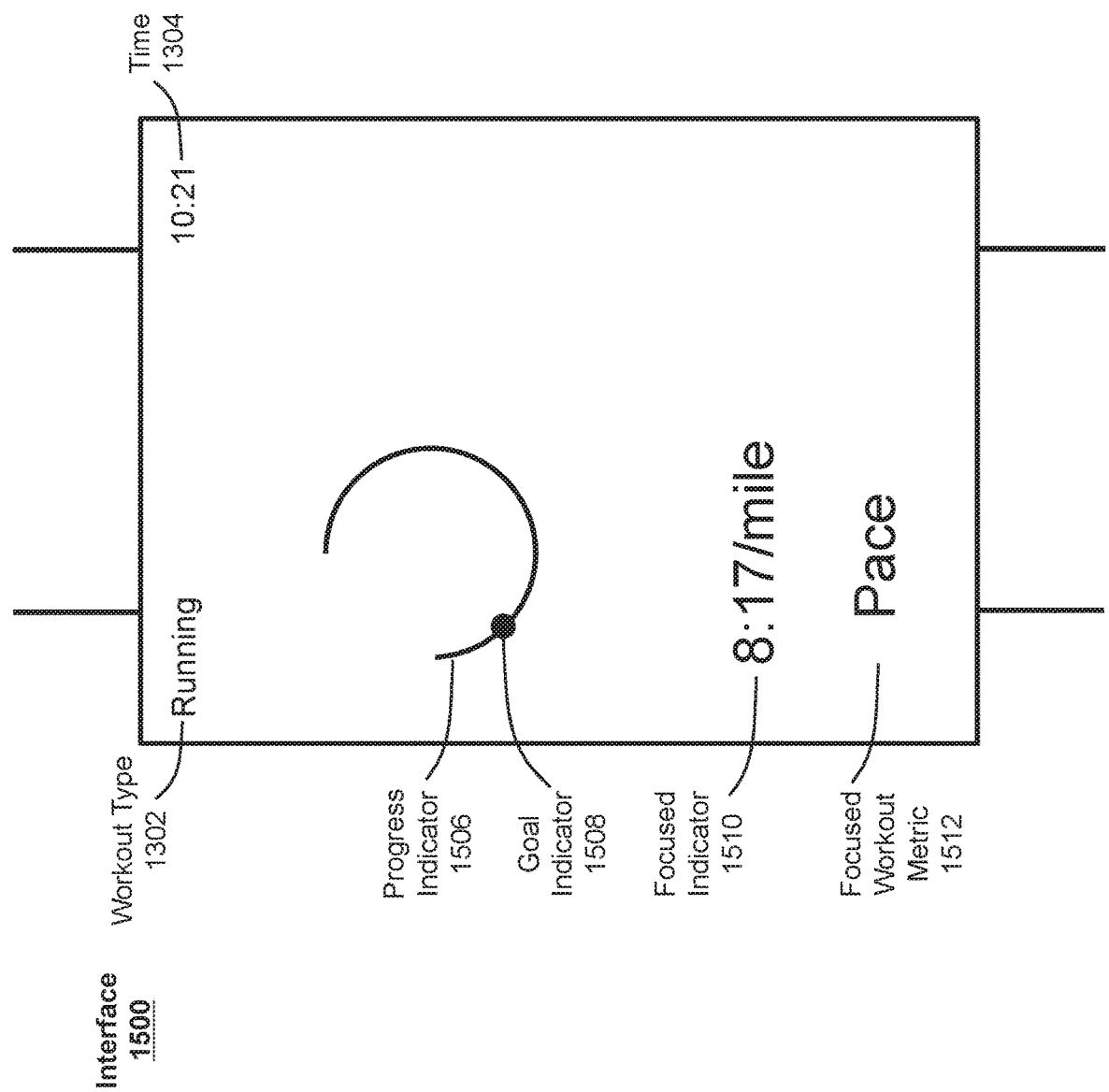
FIGS. 15, 16, 19, 20 illustrate exemplary interfaces of a simple-view display according to various examples.

In block 914, the simply-view display is displayed on the display of the device. The simple-view display includes an indicator for less than all of the workout metrics associated with the selected workout type of block 902. For example, FIG. 15 depicts interface 1500, which is an example of a simple view. Interface 1500 includes a focus indicator 1510 for the workout metric that was focused in the pro-view display. In the case of interface 1500, the pro-view display (i.e., interface 1400 of FIG. 14) was focusing the pace workout metric. Accordingly, focused workout metric 1512 is the pace workout metric and focused indicator 1510 represents a value of the pace. Interface 1500 does not include an indicator representative of the other workout metrics included in the pro-view display. For example, neither progress indicator 1506 nor goal indicator 1508 represent any of the workout metrics represented in the pro-view display. In other examples, however, progress indicator 1506 and goal indicator 1508 may be related to one of the workout metrics of the pro-view display.

Referring back to FIG. 9, at block 916 one or more processors of the device can receive activity data that is representative of sensed physical activity of a user from an activity sensor. At block 918, the one or more processors can process the received activity data to update values of workout metrics of the workout stored on the device. For example, a timer can be used to update the duration of the workout based on a difference between a current value of the timer and a value of the timer when the workout was initiated at block 904. Additionally, an accelerometer, motion sensor, gyroscope, biometric sensor, and/or GPS sensor can be used to update a distance traveled during the workout and can additionally or alternatively be used to update a number of Calories burned during the workout (in combination with the user's age, gender, and weight). The timer can be used in combination with the accelerometer, motion sensor, and/or GPS sensor to update a pace of the user during the workout. Other activity sensors can similarly be used to determine and update values of other workout attributes.

At block 920, one or more processors of the device can update the simple-view display (e.g., those shown in FIGS. 15, 16, 19 and 20) to reflect the updated values of the workout metrics determined at block 918. For example, with reference to FIG. 15, the focused indicator 1510 can be adjusted to reflect an updated value for the pace.

Blocks 916, 918, and 920 can continue to be repeated to provide the user with up to date information associated with the attributes of the workout via the workout interface. In some examples where the workout application is running in the background of the device or while the display of the device is deactivated, block 920 can be omitted and blocks 916 and 918 can repeatedly be performed to monitor the user's workout and update the monitored attributes such that an accurate display of the attributes can later be provided to the user when the physical activity application is reopened or the display of the device is activated. In some examples, upon activating the display of the device, the workout interface previously displayed (e.g., one of the interfaces displayed in FIGS. 15, 16, 19, and 20) before deactivating the display can be displayed. This workout interface can be displayed while the device is in a locked state or can be displayed in response to unlocking the device.

In block 922, one or more processors of the device can cause the simple-view display to continue to be displayed. Alternatively, something may trigger the pro-view to be displayed. For example, a gesture, such as a horizontal swipe, may be detected that causes a transition from the simple-view display to the pro-view display. Other user input could also cause the transition from the pro-view display to the simple-view display.

In the case of the simple-view display in FIG. 15, a transition back to the pro-view would cause the pro-view display of interface 1400 (FIG. 14) to be displayed. The focus of the pace workout metric, as shown by focused indicator 1510 and focused workout metric 1512, is carried over to the pro-view as indicated by focus indicator 1420 of interface 1400 (FIG. 14).

When simple-view is displayed, focused workout metric 1512 and its representative focused indicator 1510 may be changed. For example, by receiving a user input, such as a gesture on a touch-sensitive screen or other user input on a rotatable crown or button, focused workout metric may be changed to the distance workout metric, which is depicted in simple-view display in interface 1600 of FIG. 16. In interface 1600, focused workout metric 1612 is the distance workout metric and focused indicator 1610 represents a value for focused workout metric 1612.

Figure 16:
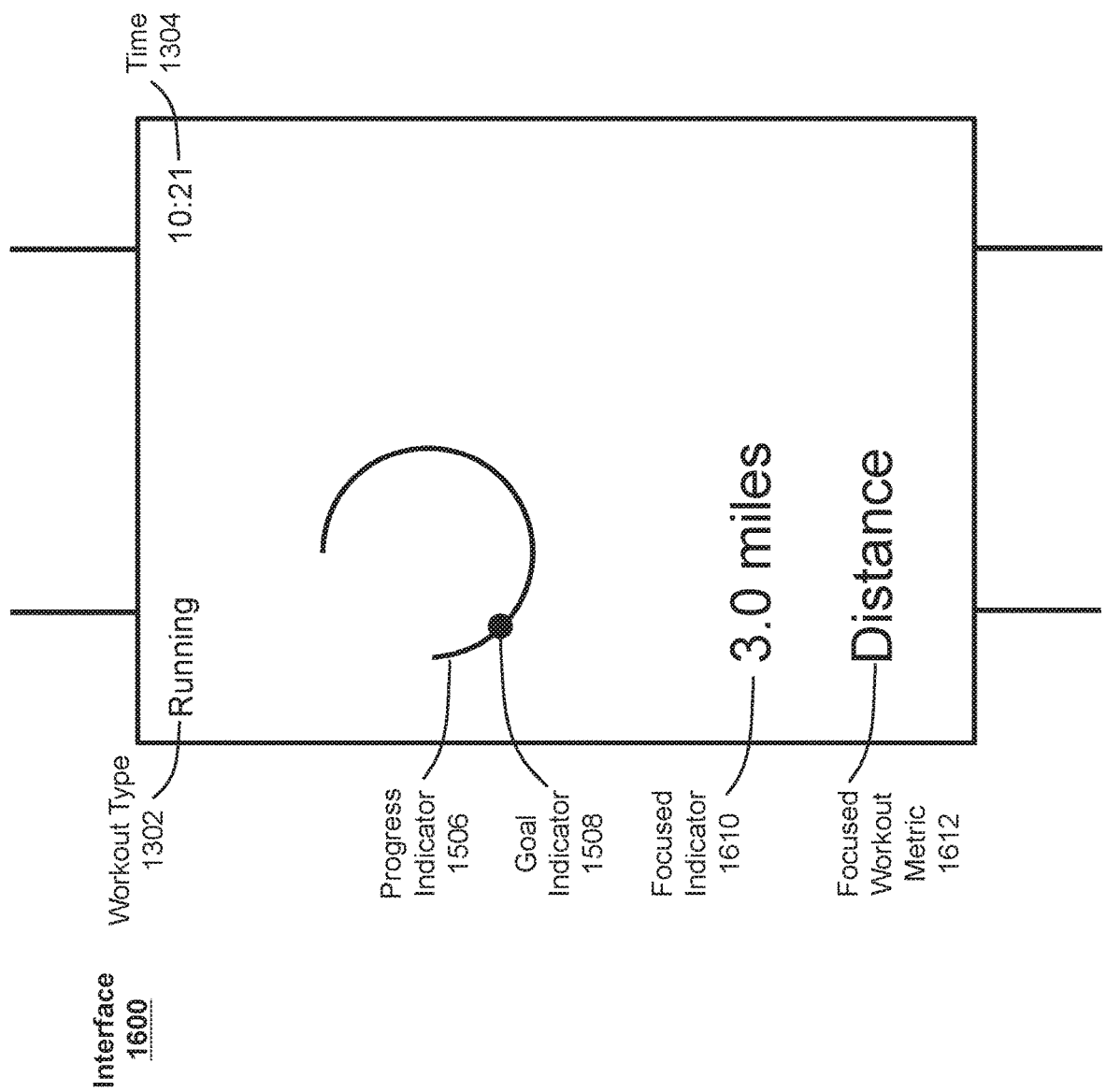

If the focused workout metric of the simple-view display changes, as is the case with the change from interface 1500 of FIG. 15 to interface 1600 of FIG. 16, the focused indicator will change with a transition back to the pro-view as described above with respect to block 922. For example, the result of a transition of the simple-view display of interface 1600 of FIG. 16 back to a pro-view display is represented in interface 1700 of FIG. 17, which shows a pro-view display with focus indicator 1720 now highlighting first indicator 1710 representing the distance workout metric.

The transition from the pro-view back to the simple view operates in a similar manner. For example, if the focus indicator changes from the first indicator (e.g., first indicator 1710 in interface 1700 of FIG. 17) to the fourth indicator (e.g., fourth indicator 1816 of interface 1800 of FIG. 18), then the result of a transition from the pro-view display to the simple-view display is shown in the simple-view display of interface 1900 of FIG. 19, which depicts focused workout metric 1912 being the elapsed time workout metric that is represented by focused indicator 1910.

Figure 17:
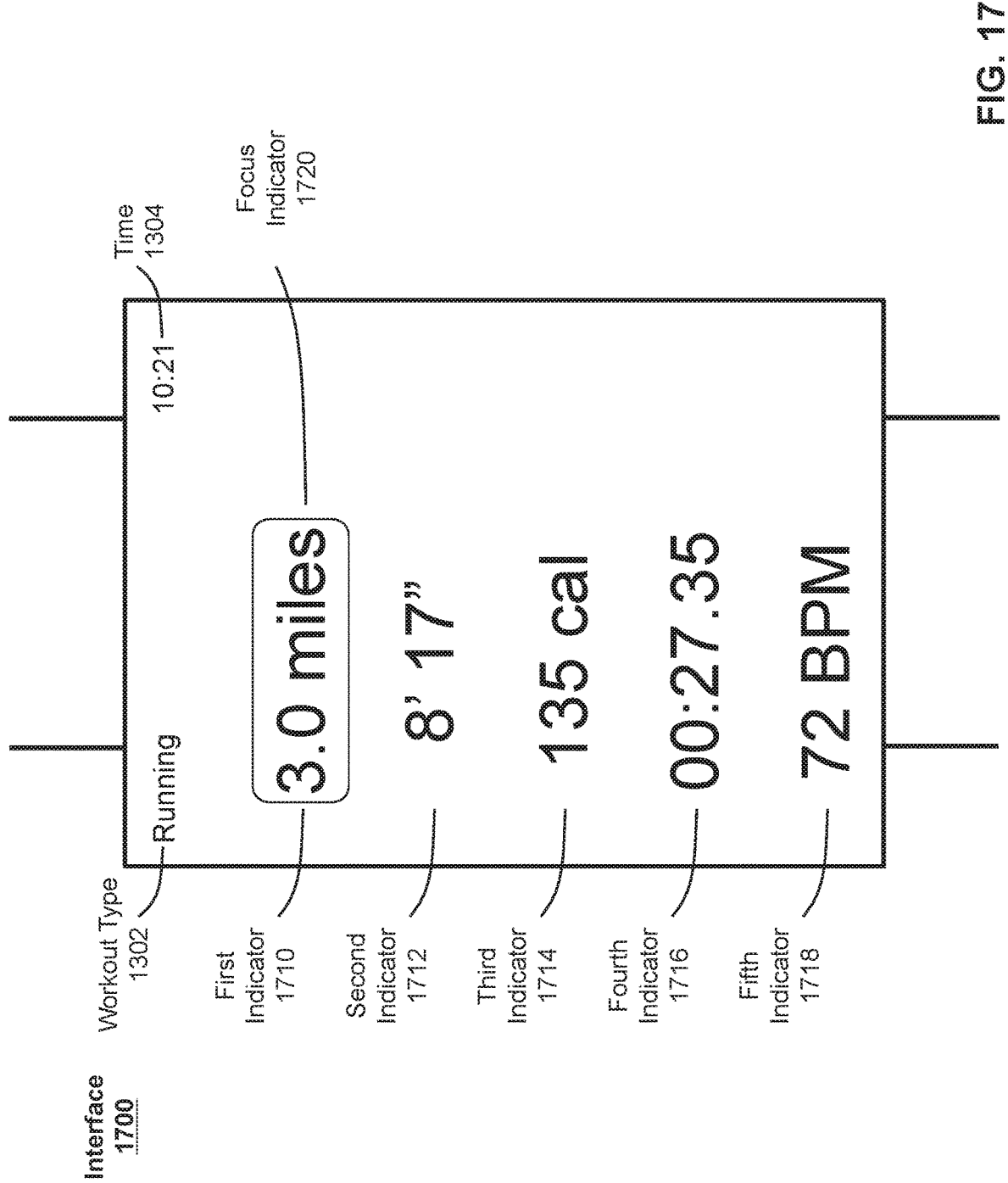
Figure 18:
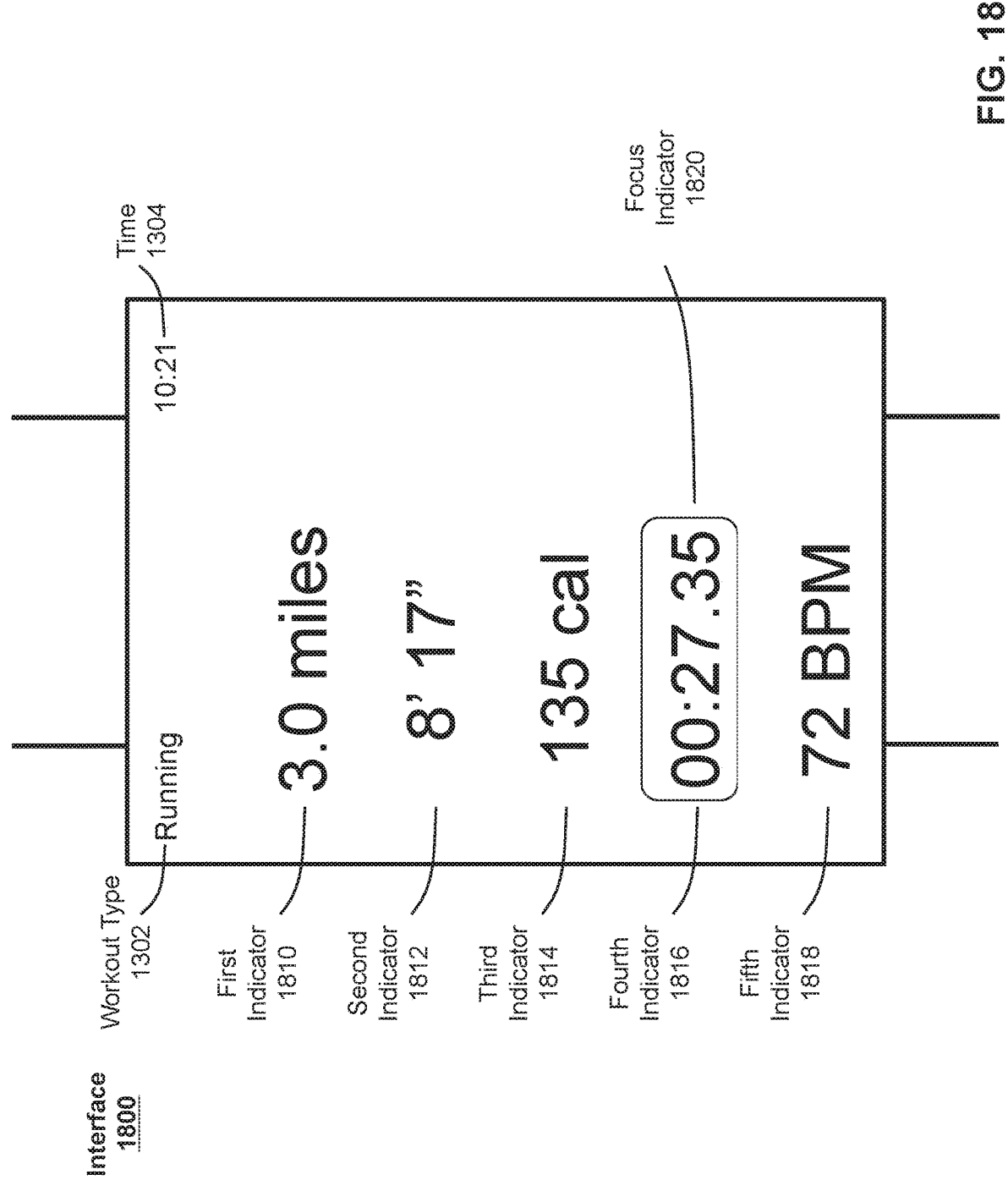
Figure 19:
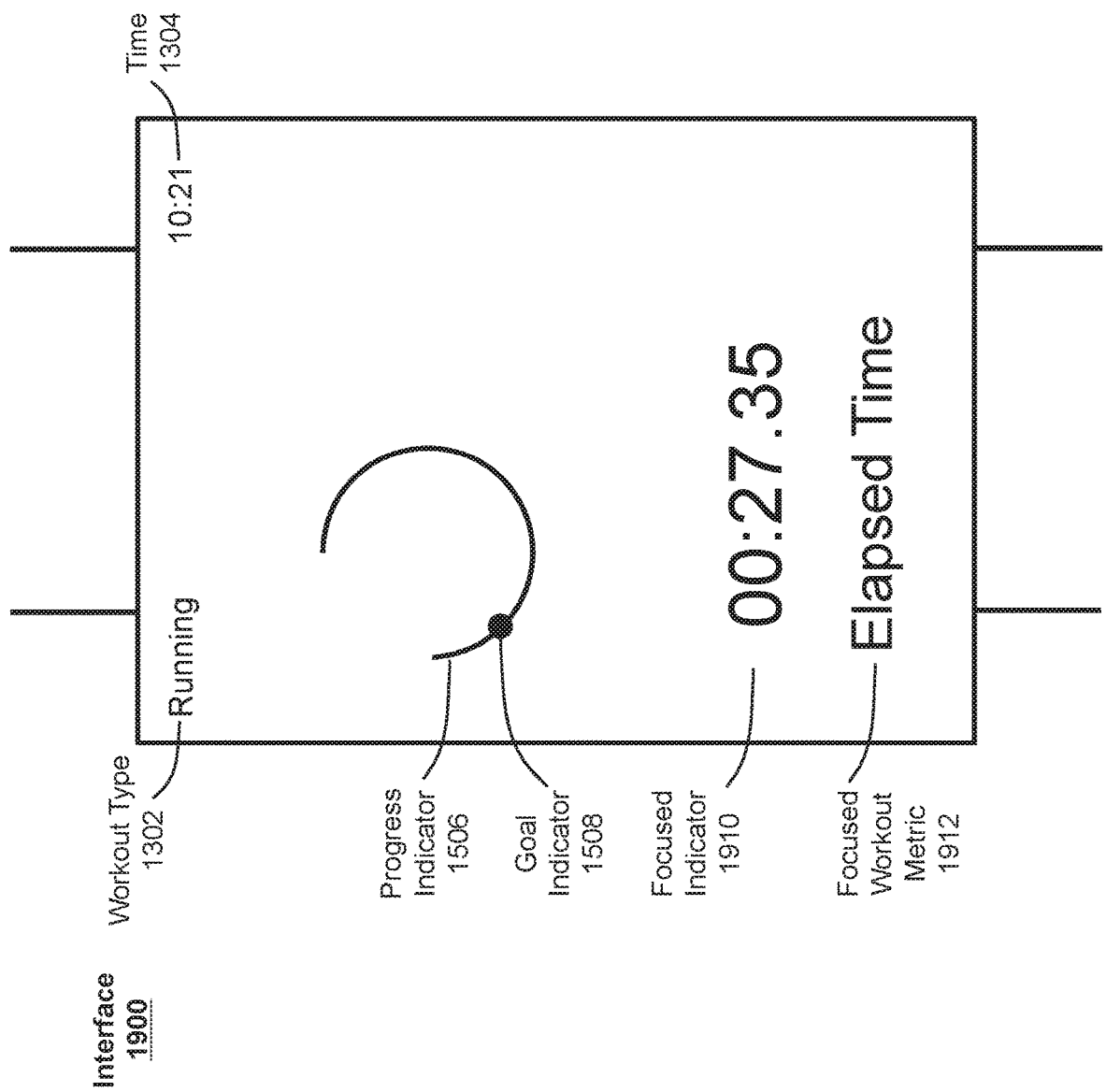
Figure 20:
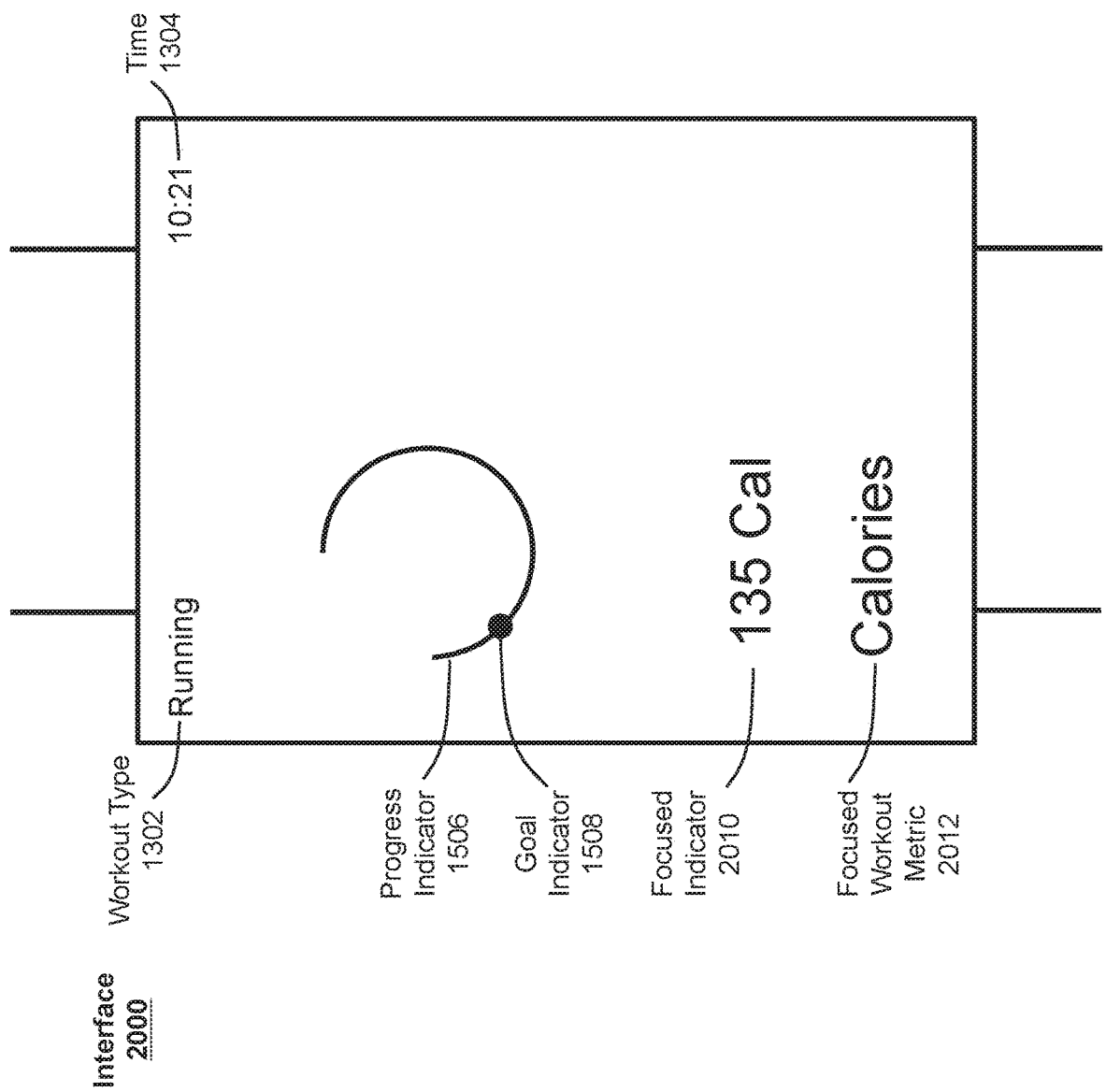
Figure 21:
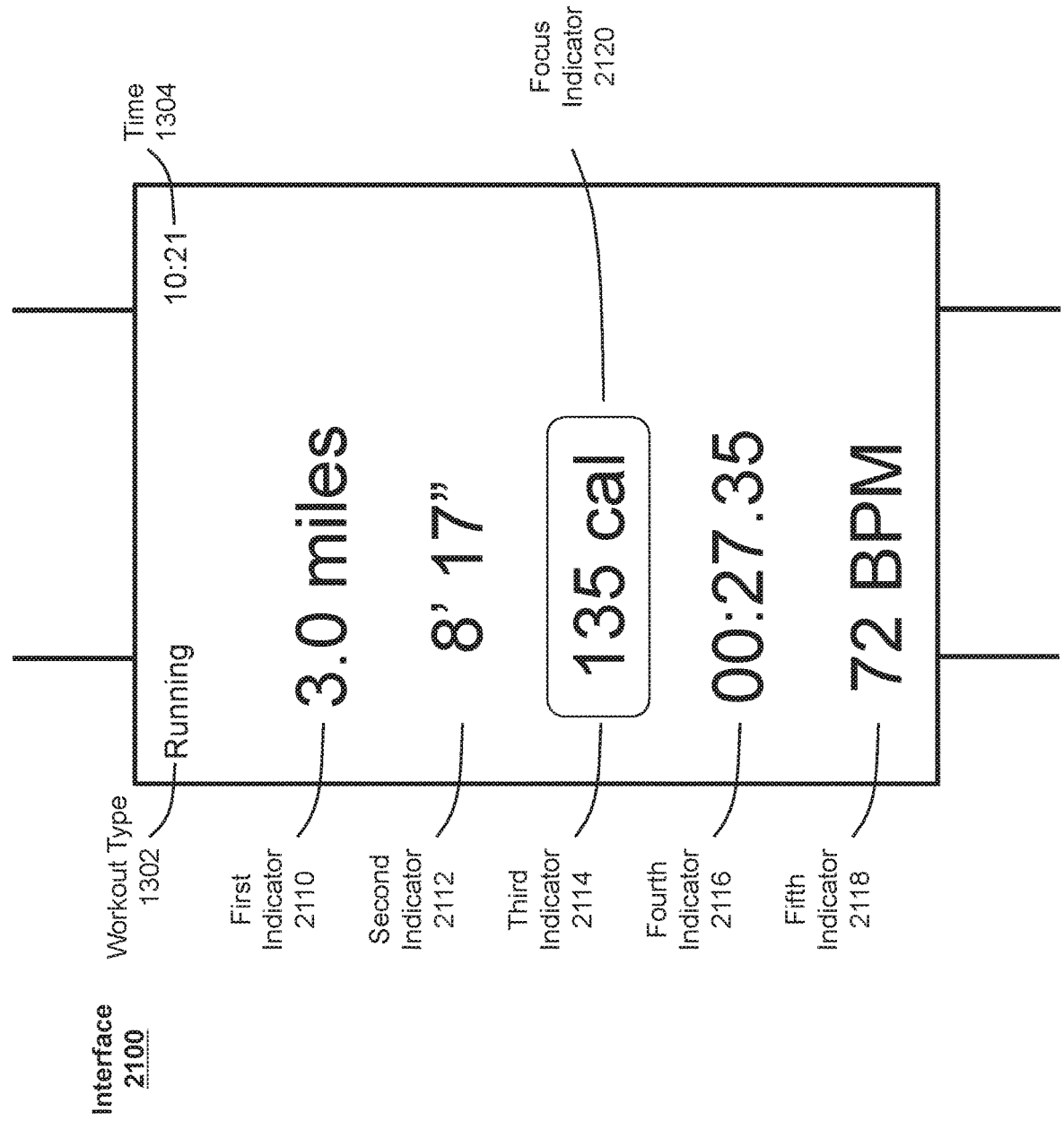

The simple-view display of interface 2000 of FIG. 20 depicts another change in the focused workout metric as compared to the simple-view display in interface 1700 of FIG. 17. Focus workout metric 2012 is now the Calories workout metric, which is represented by focused indicator 2010. The result of a transition back to the pro-view display is depicted by the pro-view display of interface 2100 of FIG. 21. In interface 2100, focus indicator 2120 is now on third indicator 2114, which represents the Calories workout metric.

The transitions between pro-views and simple-views may use animations. For example, the focused workout metric of the pro-view display may be animated to move into position in the simple-view display. Similar animations can also be used for the transitions between simple-views and pro-views.

Figure 22:
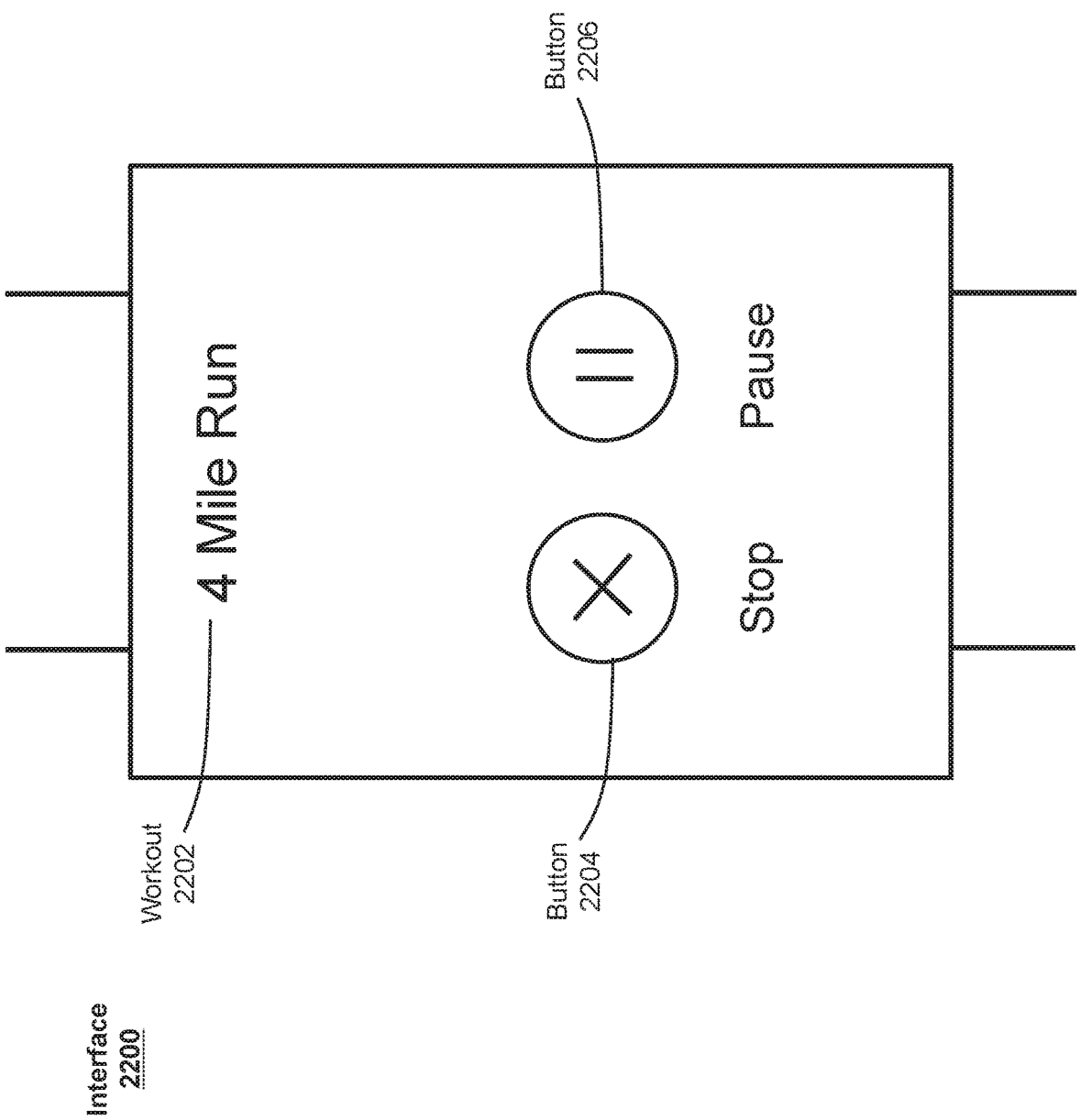
FIGS. 22-23 illustrate exemplary workout controls according to various examples.
Figure 23:
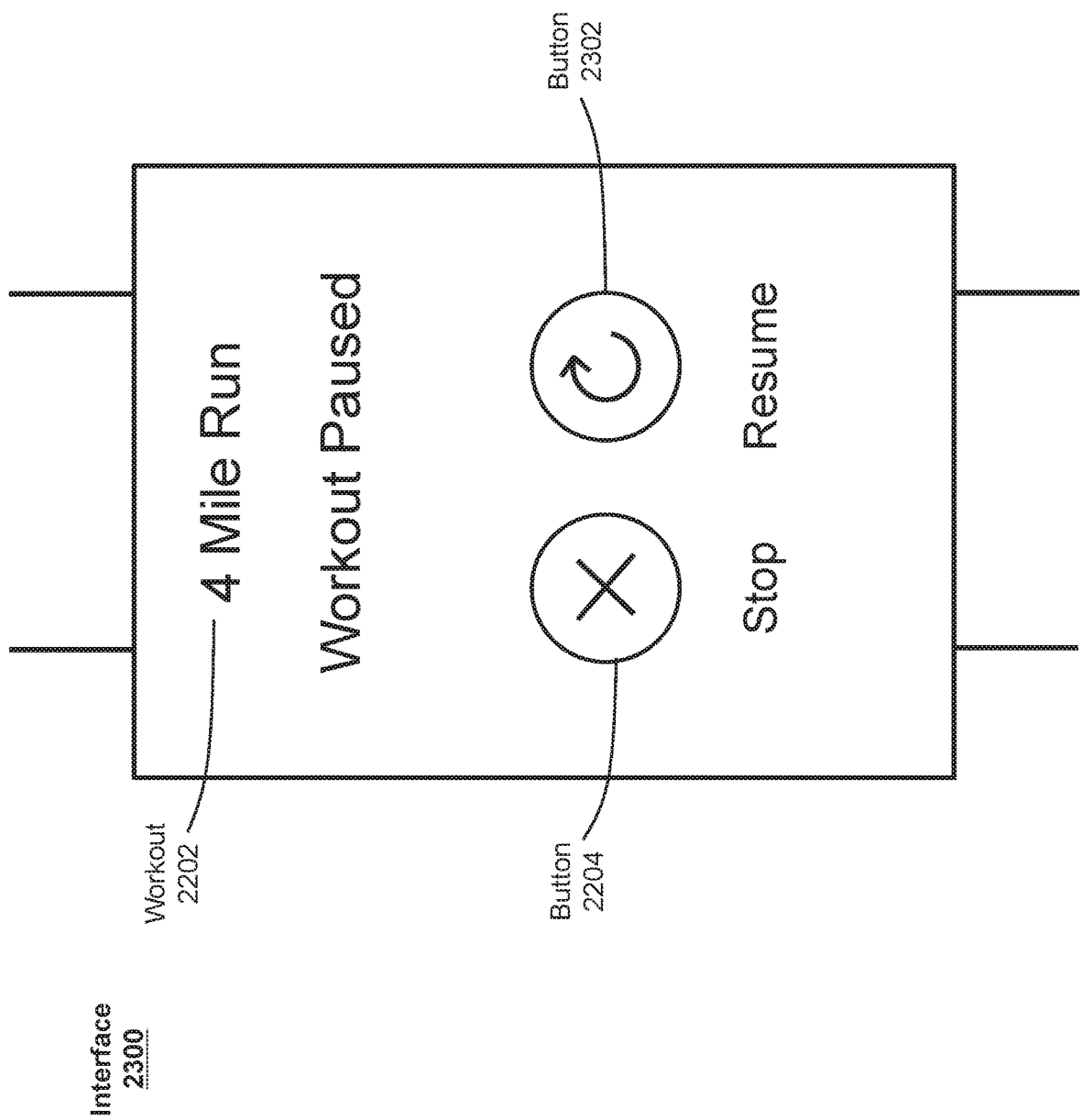

User input, such as gestures, can also be used to transition to other displays, such as a workout control or a music control. For example, FIG. 22 depicts interface 2200 for controlling workout 2202 having control buttons that include, stop button 2204 and pause button 2206. Activation of stop button 2204 ends the workout. Activation of pause button 2206, pauses the workout (for example, pauses the collection or recording of activity data) and displays a paused workout control, as depicted in interface 2300 of FIG. 23, which includes stop button 2204 and resume button 2302 that resumes the workout. FIG. 24 depicts an example music control in interface 2400 for controlling music 2402 with skip button 2404 for skipping the current music and pause button 2406 for pausing the music.

While process 900 (FIG. 9) is illustrated as starting with the pro-view, other embodiments of process 900 may start with the simple-view. In some cases, the initial view that is displayed may be user configurable or based on last view used during the last workout.

FIG. 25 shows a functional block diagram of an electronic device 25 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 25 can be combined or separated into sub-blocks to implement the principles of the various described examples. Therefore, the description herein optionally supports any possible combination or separation or further definition of the functional blocks described herein.

As shown in FIG. 25, electronic device 2500 can include a touch-sensitive display unit 2504 configured to display graphical objects and receive user gestures, activity sensor units 2506 configured to detect movement associated with the electronic device, and a processing unit 2502. In some examples, processing unit 2502 can include an identifying unit 2508, a movement detecting unit 2510, a generating unit 2512, a determining unit 2514, a gesture detecting unit 2516, and a displaying unit 2518.

Processing unit 2502 can be configured to detect (e.g., using identifying unit 2508) an identification of a type of workout to be performed. The type of workout is associated with a plurality of workout metrics, including a first workout metric and a second workout metric. Movement detecting unit 2510 can be configured to detect movement associated with an electronic device using activity sensor units 2506. Generation unit 2512 can be configured to generate activity data based on the detected movement from movement detecting unit 2510. Determining unit 2514 can be configured to determine a current value of the first workout metric and a current value of a second workout metric based on the activity data. Gesture detecting unit 2516 can be configured to detect a first user gesture corresponding to a request to display workout metric data. Displaying unit 2518 can be configured to, in response to gesture detecting unit 2516, cause, on the touch-sensitive display unit 2504 a first display. The first display can include a plurality of indicators representative of the plurality of workout metrics, including a first indicator representative of the first workout metric and a second indicator representative of the second workout metric. The first display also can include a focus indicator for one of the plurality of indicators, wherein the focus indicator indicates a focused workout metric. The gesture detecting unit 25 can be further configured to detect, while the first displaying is being displayed, a second user gesture corresponding to a request to transition between the first display and a second display. Displaying unit 2518 can be further configured to, in response to the second user gesture being detected while the first display is being displayed, cause, on the touch-sensitive display unit a first transition to the second display. The second display can include an indicator representative of the focused workout metric. Not all of the plurality of workout metrics is represented in the second display. Gesture detecting unit 2516 can be further configured to, while the second display is being displayed, detect a third user gesture corresponding to a request to transition between the second display and the first display. Displaying unit 2518 can be further configured to, in response to the third user gesture being detected while the second display is being displayed, cause, on the touch-sensitive display unit a second transition to the first display.

In some examples, the plurality workout metrics that are associated with the type of workout are configurable.

In some examples, the plurality of workout metrics includes a third workout metric and a fourth workout metric, and the plurality of indicators representative of the plurality of workout metrics further includes a third indicator representative of a third workout metric associated with the type of workout and a fourth indicator representative of a fourth workout metric associated with the type of workout. The plurality of workout metrics include at least four workout metrics selected from: a workout metric related to calories, a workout metric related to heart rate, a workout metric related to speed, a workout metric related to distance traveled, and a workout metric related to time. In some examples, the plurality of indicators in the first display includes only four indicators representative of workout metrics.

In some examples, the first indicator has a position relative to the second indicator in the first display. Gesture detecting unit 2516 can be further configured to detect a fourth user gesture corresponding to a request to change the position of the first indicator relative to the second indicator in the first display. Processing unit 2502 can be further configured to have optional changing unit 2520, which can be configured to, in response to the fourth user gesture being detected, change the position of the first indicator relative to the second indicator.

In some examples, the first indicator has a first color and the second indicator has a second color different than the first color. In some examples, the transition from the first display to the second display includes an animation. In some examples, gesture detecting unit 2516 can be further configured to detect a fifth user gesture corresponding to a request to transition from the first display or the second display to a third display. Displaying unit 2518 can be further configured to, in response to the fifth user gesture being detected while the first display or the second display is being displayed, cause on the touch-sensitive display unit the third display, including workout controls or music controls.

In some examples, gesture detecting unit 2516 can be configured to, while the first display is being displayed, detect a sixth user gesture corresponding to a request to move the focus indicator to a different indicator of the plurality of indicators on the first display. Displaying unit 2518 can be further configure to, in response to the sixth user gesture being detected, move the focus indicator to the different indicator on the first display.

In some examples, generation unit 2512 can be further configured to generate the activity data after gesture detecting unit 2516 detects the first user gesture corresponding to the request to display workout metrics.

As described above, one aspect of the present technology is the gathering and use of data available from various sources to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the appended claims.

What is claimed is:

1. An electronic device, comprising:
   a touch-sensitive display;
   one or more processors;
   memory; and
   one or more programs stored in the memory and configured to be executed by the one or more processors, the one or more programs including instructions for:
      while displaying a first user interface of a workout application, receiving a first user input to initiate a workout session;
      in response to detecting the first user input, displaying, on the touch-sensitive display, a second user interface of the workout application;
      while displaying the second user interface of the workout application, receiving a second user input; and
      in response to receiving the second user input:
         ceasing to display the second user interface of the workout application; and
         displaying, on the touch-sensitive display, a first user interface of a music application different from the workout application.

2. The electronic device of claim 1, wherein the second user input includes a swipe gesture.

3. The electronic device of claim 1, wherein the one or more programs further include instructions for:
   in response to receiving the second user input:
      displaying an animation during a transition between the second user interface of the workout application and the first user interface of the music application.

4. The electronic device of claim 1, wherein the second user input includes a swipe gesture in a first direction, and wherein the one or more programs further include instructions for:
   while displaying the first user interface of the music application, receiving a third user input, wherein the third user input includes a swipe gesture in a second direction opposite the first direction; and
   in response to receiving the third user input:

ceasing to display the first user interface of the music application; and displaying, on the touch-sensitive display, the second user interface of the workout application.

5. The electronic device of claim 1, wherein the second user interface of the workout application includes a plurality of indicators representative of a plurality of workout metrics, wherein the plurality of workout metrics includes calories, heart rate, speed, distance traveled, elapsed time, or any combination thereof.

6. The electronic device of claim 5, wherein the plurality of workout metrics is user configurable via a user configuration interface.

7. The electronic device of claim 5, wherein the one or more programs further include instructions for:

receiving activity data corresponding to detected movement of the electronic device; and updating at least one of the plurality of indicators representative of the plurality of workout metrics based on the activity data.

8. The electronic device of claim 1, wherein the first user interface of the music application includes a plurality of music control affordances, wherein each music control affordance, when selected via user input, is configured to control audio output via the electronic device.

9. The electronic device of claim 8, wherein the plurality of music control affordances includes a skip affordance or a pause affordance.

10. The electronic device of claim 1, wherein the first user interface of the music application includes an audio indicator corresponding to a current audio file configured to be output via the electronic device.

11. A non-transitory computer-readable storage medium storing one or more programs configured to be executed by one or more processors of an electronic device with a touch-sensitive display, the one or more programs including instructions for:

while displaying a first user interface of a workout application, receiving a first user input to initiate a workout session;

in response to detecting the first user input, displaying, on the touch-sensitive display, a second user interface of the workout application;

while displaying the second user interface of the workout application, receiving a second user input; and in response to receiving the second user input:

ceasing to display the second user interface of the workout application; and displaying, on the touch-sensitive display, a first user interface of a music application different from the workout application.

12. The non-transitory computer-readable storage medium of claim 11, wherein the second user input includes a swipe gesture.

13. The non-transitory computer-readable storage medium of claim 11, wherein the one or more programs further include instructions for:

in response to receiving the second user input:

displaying an animation during a transition between the second user interface of the workout application and the first user interface of the music application.

14. The non-transitory computer-readable storage medium of claim 11, wherein the second user input includes a swipe gesture in a first direction, and wherein the one or more programs further include instructions for:

while displaying the first user interface of the music application, receiving a third user input, wherein the third user input includes a swipe gesture in a second direction opposite the first direction; and in response to receiving the third user input:

ceasing to display the first user interface of the music application; and displaying, on the touch-sensitive display, the second user interface of the workout application.

15. The non-transitory computer-readable storage medium of claim 11, wherein the second user interface of the workout application includes a plurality of indicators representative of a plurality of workout metrics, wherein the plurality of workout metrics includes calories, heart rate, speed, distance traveled, elapsed time, or any combination thereof.

16. The non-transitory computer-readable storage medium of claim 15, wherein the plurality of workout metrics is user configurable via a user configuration interface.

17. The non-transitory computer-readable storage medium of claim 15, wherein the one or more programs further include instructions for:

receiving activity data corresponding to detected movement of the electronic device; and updating at least one of the plurality of indicators representative of the plurality of workout metrics based on the activity data.

18. The non-transitory computer-readable storage medium of claim 11, wherein the first user interface of the music application includes a plurality of music control affordances, wherein each music control affordance, when selected via user input, is configured to control audio output via the electronic device.

19. The non-transitory computer-readable storage medium of claim 18, wherein the plurality of music control affordances includes a skip affordance or a pause affordance.

20. The non-transitory computer-readable storage medium of claim 11, wherein the first user interface of the music application includes an audio indicator corresponding to a current audio file configured to be output via the electronic device.

21. A method, comprising:

at an electronic device including a touch-sensitive display:

while displaying a first user interface of a workout application, receiving a first user input to initiate a workout session;

in response to detecting the first user input, displaying, on the touch-sensitive display, a second user interface of the workout application;

while displaying the second user interface of the workout application, receiving a second user input; and in response to receiving the second user input:

ceasing to display the second user interface of the workout application; and displaying, on the touch-sensitive display, a first user interface of a music application different from the workout application.

22. The method of claim 21, wherein the second user input includes a swipe gesture.

23. The method of claim 21, the method further comprising:

in response to receiving the second user input:

displaying an animation during a transition between the second user interface of the workout application and the first user interface of the music application.

24. The method of claim 21, wherein the second user input includes a swipe gesture in a first direction, the method further comprising:
- while displaying the first user interface of the music application, receiving a third user input, wherein the third user input includes a swipe gesture in a second direction opposite the first direction; and
- in response to receiving the third user input:
  - ceasing to display the first user interface of the music application; and
  - displaying, on the touch-sensitive display, the second user interface of the workout application.

25. The method of claim 21, wherein the second user interface of the workout application includes a plurality of indicators representative of a plurality of workout metrics, wherein the plurality of workout metrics includes calories, heart rate, speed, distance traveled, elapsed time, or any combination thereof.

26. The method of claim 25, wherein the plurality of workout metrics is user configurable via a user configuration interface.

27. The method of claim 25, the method further comprising:
- receiving activity data corresponding to detected movement of the electronic device; and
- updating at least one of the plurality of indicators representative of the plurality of workout metrics based on the activity data.

28. The method of claim 21, wherein the first user interface of the music application includes a plurality of music control affordances, wherein each music control affordance, when selected via user input, is configured to control audio output via the electronic device.

29. The method of claim 28, wherein the plurality of music control affordances includes a skip affordance or a pause affordance.

30. The method of claim 21, wherein the first user interface of the music application includes an audio indicator corresponding to a current audio file configured to be output via the electronic device.

* * * * *